(12) United States Patent
Giobbi

(10) Patent No.: US 9,807,091 B2
(45) Date of Patent: *Oct. 31, 2017

(54) PROXIMITY-BASED SYSTEM FOR AUTOMATIC APPLICATION OR DATA ACCESS AND ITEM TRACKING

(71) Applicant: Proxense, LLC, Bend, OR (US)

(72) Inventor: John J. Giobbi, Bend, OR (US)

(73) Assignee: Proxense, LLC, Bend, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/207,313

(22) Filed: Jul. 11, 2016

(65) Prior Publication Data

US 2017/0041315 A1 Feb. 9, 2017

Related U.S. Application Data

(63) Continuation of application No. 13/048,740, filed on Mar. 15, 2011, now Pat. No. 9,418,205.
(Continued)

(51) Int. Cl.
| | |
|---|---|
| *H04L 29/06* | (2006.01) |
| *G06F 19/00* | (2011.01) |
| *G06F 21/32* | (2013.01) |
| *H04W 12/04* | (2009.01) |
| *H04W 12/06* | (2009.01) |

(52) U.S. Cl.
CPC ........ *H04L 63/0861* (2013.01); *G06F 19/322* (2013.01); *G06F 19/323* (2013.01); *G06F 21/32* (2013.01); *H04L 63/06* (2013.01); *H04L 63/0853* (2013.01); *H04W 12/04* (2013.01); *H04W 12/06* (2013.01); *G06F 2221/2111* (2013.01); *G06F 2221/2129* (2013.01)

(58) Field of Classification Search
CPC ..... G06F 19/322–19/323; G06F 21/32–21/35; G06F 21/6218; G06F 21/78; G06F 2221/2111–2221/2129; H04L 63/06; H04L 63/083; H04L 63/0853; H04L 63/0861; G06Q 20/382; G06Q 20/4014; G06Q 20/40145; G06Q 40/00; G07C 9/00158; H04W 12/04; H04W 12/06
See application file for complete search history.

(56) References Cited

U.S. PATENT DOCUMENTS

| | | |
|---|---|---|
| 5,623,552 A | 4/1997 | Lane |
| 6,177,887 B1 | 1/2001 | Jerome |
| (Continued) | | |

FOREIGN PATENT DOCUMENTS

WO WO2007087558 8/2007

*Primary Examiner* — Orlando Bousono
(74) *Attorney, Agent, or Firm* — Patent Law Works LLP

(57) ABSTRACT

A system and method provide automatic access to applications or data. A portable physical device, referred to herein as a Personal Digital Key or "PDK", stores one or more profiles in memory, including a biometric profile acquired in a secure trusted process and uniquely associated with a user that is authorized to use and associated with the PDK. The PDK wirelessly transmits identification information including a unique PDK identification number, the biometric profile and a profile over a secure wireless channel to a reader. A computing device is coupled to the reader. An auto login server is coupled to the reader and the computing device and launches one or more applications associated with a user name identified by the received profile.

20 Claims, 35 Drawing Sheets

Related U.S. Application Data

(60) Provisional application No. 61/314,032, filed on Mar. 15, 2010.

(56) References Cited

U.S. PATENT DOCUMENTS

| | | |
|---|---|---|
| 6,728,397 B2 | 4/2004 | McNeal |
| 6,859,812 B1 | 2/2005 | Paynor |
| 6,879,966 B1 | 4/2005 | Lapsley et al. |
| 7,055,171 B1 | 5/2006 | Martin et al. |
| 7,231,068 B2 | 6/2007 | Tibor |
| 7,349,557 B2 | 3/2008 | Tibor |
| 7,380,202 B1 | 5/2008 | Lindhorst et al. |
| 7,565,329 B2 | 7/2009 | Lapsley et al. |
| 7,606,733 B2 | 10/2009 | Shmueli et al. |
| 8,678,273 B2 | 3/2014 | McNeal |
| 2002/0199120 A1 | 12/2002 | Schmidt |
| 2004/0246950 A1 | 12/2004 | Parker et al. |
| 2005/0028168 A1 | 2/2005 | Marcjan |
| 2005/0210270 A1 | 9/2005 | Rohatgi et al. |
| 2005/0216639 A1 | 9/2005 | Sparer et al. |
| 2006/0143441 A1 | 6/2006 | Giobbi |
| 2006/0273176 A1 | 12/2006 | Audebert et al. |
| 2006/0293925 A1 | 12/2006 | Floma |
| 2007/0156850 A1 | 7/2007 | Corrion |
| 2007/0169121 A1 | 7/2007 | Hunt et al. |
| 2007/0294755 A1 | 12/2007 | Dadhia et al. |
| 2008/0071577 A1 | 3/2008 | Highley |
| 2008/0109895 A1 | 5/2008 | Janevski |
| 2008/0150678 A1 | 6/2008 | Giobbi et al. |
| 2008/0250388 A1 | 10/2008 | Meyer et al. |
| 2008/0313728 A1 | 12/2008 | Pandrangi et al. |
| 2009/0081996 A1 | 3/2009 | Duggal et al. |
| 2010/0169442 A1 | 7/2010 | Liu et al. |
| 2010/0169964 A1 | 7/2010 | Liu et al. |
| 2011/0072034 A1 | 3/2011 | Sly et al. |

Figure 30

Current Alert List — 3202

| Name | Description | Source | Trigger |
|---|---|---|---|
| alert name | alert description | monitored item | trigger event |

Create New | Edit | Delete | View Log

Alert Details — 3204

If ⦿ PROX ○ Group
○ Sensor ○ Group
identifier sensor list ▽

○ is detected by
○ is not detected by
○ temperature enters range
○ temperature is out of range    lower temp - upper temp    Add / Remove
○ response is lost via: ⦿ default
○ custom message

| Select | Message Type | Address List | Priority Level |
|---|---|---|---|
| ✓ | Visual | user list | 1 |
| ✓ | Email | address list | 1 |
|  | SMS | address list | 2 |
| ✓ | Workstation Message | workstation ID list | 2 |
|  | Broadcast Message | network ID | 3 |
|  | Custom | custom interface | 4 |

Save New | Update Current | Clear

Current Report List

| Name | Description | Form | Type |
|---|---|---|---|
| report name | report description | graphic/text | Report type |

[Create New] [Edit] [Delete] [Go]

3302

3300

Report Details

*report type*

1 Select Report Type: *Criteria Record*   [New Search]

2 Select PROX: ○ All Visited  ● Sensor ○ Group
 ○ Custom ▷  *identifier*  ... and Make Primary:

3 Select Zones:

4 Select Time Period: *yesterday*  00/00/00  00:00 AM/PM  thru  00/00/00  00:00 AM/PM 5 Select Display Options:

Visit Details
- ☑ Arrival Time
- ☑ Departure Time
- ☑ Time in Zone
- ☑ Last Zone Visited
- ☑ Time Between Zones

Sub-Totals
- ☑ Total Visits
- ☑ Total Time of Visits
- ☑ Average Time Per Visit
- ☑ Average Time Between Zones
- ☐ Most Common Previous Zone

Report Totals (Zone focus)
- ☑ Total PROX Visiting
- ☑ Total Visits
- ☑ Total Time of Visits
- ☑ Average Visits Per PROX
- ☑ Average Time Per Visit
- ☑ Average Time Between Zones
- ☑ Most Common Previous Zone

*PROX list*

Report Totals (PROX focus)
- ☑ Total Zones Visited
- ☑ Total Visits
- ☑ Total Time of Visits
- ☐ Average Visits Per Zone
- ☐ Average Time Per Visit
- ☐ Average Time Between Zones
- ☐ Most Common Previous Zone
- ☐ Total Time Out of Coverage

[Save New] [Update Current] [Clear]

PROXIMITY-BASED SYSTEM FOR AUTOMATIC APPLICATION OR DATA ACCESS AND ITEM TRACKING

CROSS REFERENCE TO RELATED APPLICATIONS

This application is a continuation of and claims priority to U.S. application Ser. No. 13/048,740, filed Mar. 15, 2011, titled "Proximity-Based System for Automatic Application or Data Access and Item Tracking", which claims the benefit of U.S. Patent Application No. 61/314,032, filed Mar. 15, 2010, the entireties of which are hereby incorporated by reference.

Applicants hereby notify the USPTO that the claims of the present application are different from those of the aforementioned related applications. Therefore, Applicant rescinds any disclaimer of claim scope made in the parent application or any other predecessor application in relation to the present application. The Examiner is therefore advised that any such disclaimer and the cited reference that it was made to avoid may need to be revisited at this time. Furthermore, the Examiner is also reminded that any disclaimer made in the present application should not be read into or against the parent application, the grandparent application or any other related application.

BACKGROUND OF THE INVENTION

1. Field of Art

This disclosure generally relates to the field of radio frequency identification (RFID) and electronic authentication, and more specifically, to systems and methods for automatic and secure authentication of users.

2. Description of the Related Art

Optimizing patient care is an ever-changing and challenging endeavor. Ensuring quality patient care that is safe, efficient and cost-effective is very important to patients, as well as healthcare providers. Conventional technologies used in the healthcare industry for aiding provider patient care, monitoring patient treatment, receiving and retrieving patient data and monitoring provider activity have not yet provided optimal features to meet these needs. Recently, software application systems have been developed in an attempt to improve patient care and provider performance.

Currently, many healthcare facilities utilize electronic software and applications to securely store and efficiently access private patient information. In many healthcare institutions, healthcare providers access patient electronic records with authorized entry into the healthcare software application system. In most conventional systems, providers are provided with a unique user name and password that they must enter into a system each time they need to access patient information. Further, when a healthcare provider is done accessing patient records, the healthcare provider must log out of the system to ensure that unauthorized use does not occur. The process of logging in and logging off each time may prove to be quite time-consuming given the number of patients a provider visits in a given day.

Another problem for many healthcare facilities is making sure that equipment is deployed in a manner that maximizes their usage and availability. For example, in many hospitals the location of equipment is not tracked and monitored other than during an annual equipment inventory. Thus, healthcare providers may not be aware of the precise location of equipment or know when equipment is currently in use. Thus, conventional methods provided limited ability to track the location of equipment.

BRIEF SUMMARY OF THE INVENTION

A system and method provides automatic access to applications or data while maintaining application or data security. A portable physical device, referred to herein as a Personal Digital Key or "PDK", stores one or more profiles uniquely associated with a user in a memory. In one embodiment, one of the profiles is a biometric profile that is acquired in a secure trusted process and is uniquely associated with a user authorized to use the PDK and associated with the PDK. A reader wirelessly communicates with the PDK and receives a profile from the PDK. A computing device is coupled to the reader and displays data on a display device responsive to receiving data associated with the profile from the reader. Additionally, an auto login sever is coupled to the computing device and to the reader and the auto login server receives the profile from the reader and launches, on the computing device, one or more applications associated with a user name identified by the profile.

In one embodiment, the reader acquires a biometric input from the user associated. The biometric input can be acquired by, for example, a fingerprint scan, iris scan, retinal scan, palm scan, face scan, DNA analysis, signature analysis, voice analysis or any other input mechanism that provides physical or behavioral characteristics uniquely associated with the individual. The reader compares the biometric profile received from the PDK to the biometric input acquired from the user to determine if an application should be launched or if data access is authorized.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the disclosed subject matter.

BRIEF DESCRIPTION OF DRAWINGS

The disclosed embodiments have other advantages and features which will be more readily apparent from the detailed description, the appended claims, and the accompanying figures (or drawings). A brief introduction of the figures is below.

FIG. 30 is an example user interface for tracking a user or an asset associated with a PDK in accordance with the present invention.

FIG. 32 is an example user interface for describing an alert for a tracked user or asset in accordance with the present invention.

FIG. 33 is an example user interface for describing a report for a tracked user or asset in accordance with the present invention.

Figure 1:
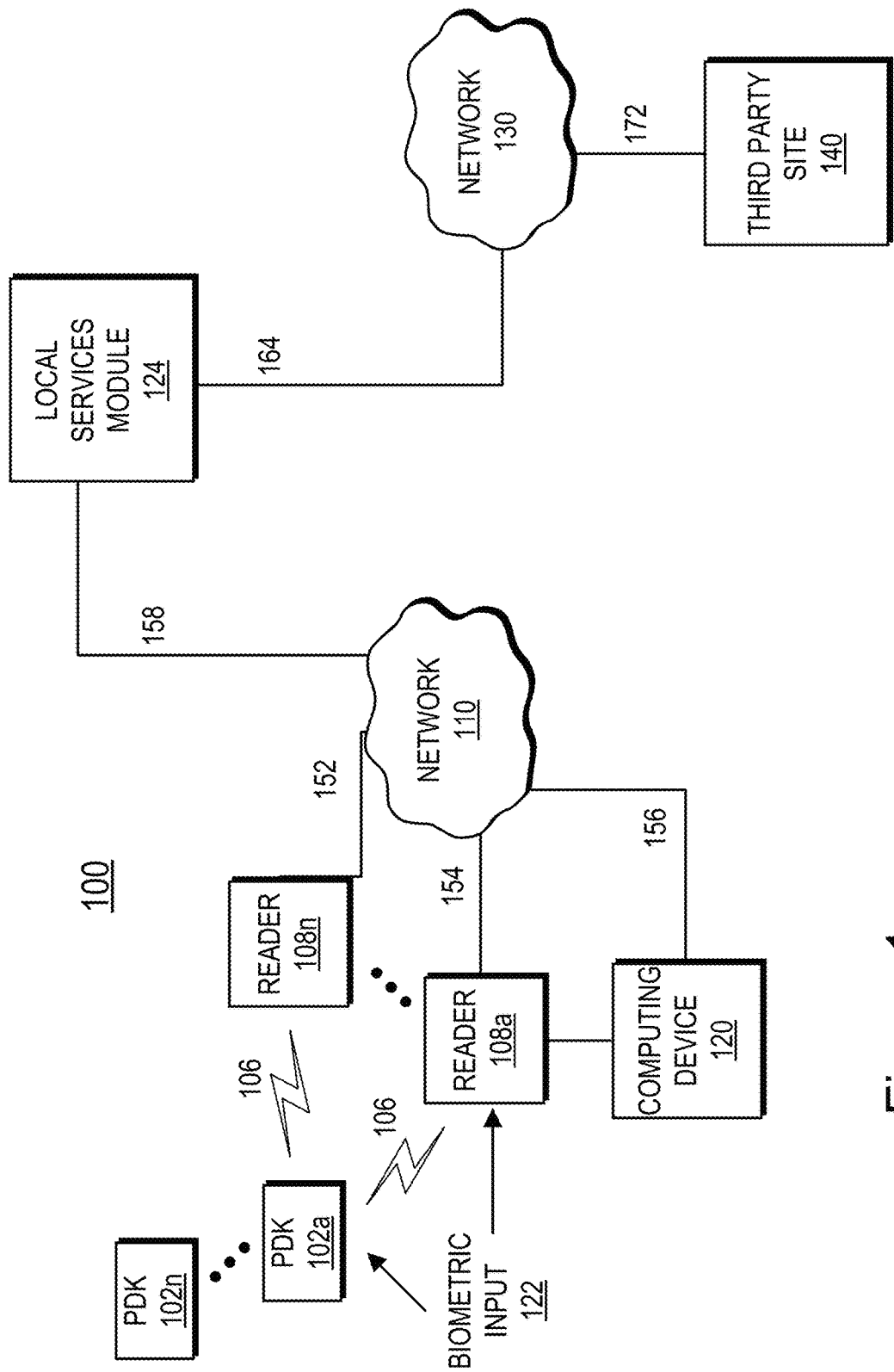
FIG. 1 is a block diagram illustrating a system for securely authenticating an individual for accessing data or one or more applications in accordance with the present invention.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

A system and method for transitioning between pages using an electronic paper display (EPD) are described. In the following description, for purposes of explanation, numerous specific details are set forth in order to provide a thorough understanding of the invention. It will be apparent, however, to one skilled in the art that the invention can be practiced without these specific details. In other instances, structures and devices are shown in block diagram form in order to avoid obscuring the invention. For example, the present embodiment of invention is described in one embodiment below with reference to portable computing devices that are exemplified in a hardware and software platform using electronic paper, e-paper or electronic ink display. However, the present embodiment of invention applies to any type of portable computing device that can capture ink, data and commands, and send documents electronically.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment. In particular the present embodiment of invention is described below in the content of two distinct architectures and some of the components are operable in both architectures while others are not.

Some portions of the detailed descriptions that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present embodiment of invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Finally, the algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the present embodiment of invention is described with reference to a particular programming language. It will be appreciated that a variety of programming languages may be used to implement the teachings of the invention as described herein.

FIG. 1 is a high level block diagram illustrating a system for securely authenticating an individual for accessing data or one or more applications. The system 100 comprises a Personal Digital Key (PDK) 102, a Reader 108, a network 110, a computing device 120, a local services module 124, a third party link module 126, a record system 128, a network 130 and a third party site 140. The Reader 108 is coupled to PDK 102 by a wireless link 106 and coupled to a network 110 by either a wired or wireless link represented by lines 152 and 154. The Reader 108 is also adapted to receive a biometric input 122 from a user and is capable of displaying status to a user. The PDK 102 is also adapted to receive biometric input 122 from a user. The network 110 couples the local services module 124 and third party link module 126 to the Reader 108. The network 110 also couples the local servers 124 and third party link module 126 to the record system 128 via signal lines 158 and 160. In alternative embodiments, different or additional external services, registries or databases (not shown) are coupled to the network 110. In another embodiment, the Reader 108 operates as a standalone device without a connection to the network 110. The network 130 couples the third party link module 126 to the third party site 140 and services provided by the third party site 140, such as pharmacy services, insurance services or lab services.

The system 100 addresses applications where it is important to ensure a specific individual is authorized to perform a given transaction. A transaction as used herein include executing a purchase or financial dealing, enabling access to physical and/or digital items, providing identification or personal information or executing other tasks where it is important to authenticate an individual for use. In one embodiment, the Reader 108 wirelessly receives information stored in the PDK 102 that uniquely identifies the PDK 102 and the individual carrying the PDK 102. In another embodiment, the Reader 108 also receives a biometric input 122 from the individual. For example, the Reader 108 receives a fingerprint, a retinal scan, an iris scan, a facial scan or any other suitable biometric input associated with the individual. The PDK 102 can also receive biometric input 122 from the individual. Based on the received information, the Reader 108 determines if the transaction should be authorized. Beneficially, the system 100 provides comprehensive authentication without the need for PINs or passwords. Moreover, personal biometric information need not be stored in any local or remote storage database and is only stored on the user's own PDK 102. Furthermore, in one embodiment, purchase transactions can be efficiently completed without requiring the use of physical credit cards, tokens or other user action beyond initiating the transaction.

The PDK 102 is a compact, portable uniquely identifiable wireless device typically carried by an individual or affixed to an object or device. The PDK 102 stores digital information in a tamper-proof format uniquely associating the PDK 102 with an individual. Example embodiments of PDKs are described in more detail in U.S. patent application Ser. No. 11/292,330, entitled "Personal Digital Key And Receiver/Decoder Circuit System And Method" filed on Nov. 30, 2005; U.S. patent application Ser. No. 11/620,581 entitled "Wireless Network Synchronization Of Cells And Client Devices On A Network" filed on Jan. 5, 2007; and U.S. patent application Ser. No. 11/620,577 entitled "Dynamic Real-Time Tiered Client Access" filed on Jan. 5, 2007, the entire contents of which are all incorporated herein by reference.

To establish the trust, credibility and confidence of the authentication system, information stored in the PDK 102 is acquired by a process that is trusted, audited and easily verified. The process is ensured by a trusted third-party system, referred to herein as a "Notary," that administers the acquisition and storage of information in the PDK 102 according to defined security protocols. In one embodiment, the Notary is a system and/or a trusted individual that witnesses the acquisition and storage either in person or remotely. In another embodiment, the Notary comprises trusted hardware that administers the initialization process by an automated system. Thus, once initialized by the trusted process, the PDK 102 can prove that the information it stores is that of the individual. Example embodiments of the initialization process are described in U.S. patent application Ser. No. 11/744,832 to John Giobbi, et al., entitled "Personal Digital Key Initialization and Registration For Secure Transaction" filed on May 5, 2007, the entire contents of which are incorporated herein by reference.

The Reader 108 wirelessly communicates with the PDK 102 when the PDK 102 is within a proximity zone of the Reader 108. The proximity zone can be, for example, several meters in radius and can be adjusted dynamically by the Reader 108. Thus, in contrast to many conventional radio frequency identification (RFID) devices, the Reader 108 is able to detect and communicate with the PDK 102 without requiring an individual using, or associated with the PDK 102, to remove the PDK 102 from his/her pocket, wallet, purse, etc. Generally, the Reader 108 receives uniquely identifying information from the PDK 102 and initiates an authentication process for the individual carrying the PDK 102. In one embodiment, the Reader 108 is adapted to receive a biometric input 122 from the individual. The biometric input 122 comprises a representation of physical or behavioral characteristics unique to the individual. For example, the biometric input 122 can include a fingerprint, a palm print, a retinal scan, an iris scan, a photograph, a signature, a voice sample or any other biometric information such as DNA, RNA or their derivatives that can uniquely identify the individual. The Reader 108 compares the biometric input 122 to information received from the PDK 102 to determine if a transaction should be authorized. Alternatively, the biometric input 122 can be obtained by a biometric reader 470 (FIG. 4) on the PDK 102 and transmitted to the Reader 108 for authentication. In additional alternative embodiment, some or all of the authentication process can be performed by the PDK 102 instead of the Reader 108.

Figure 2:
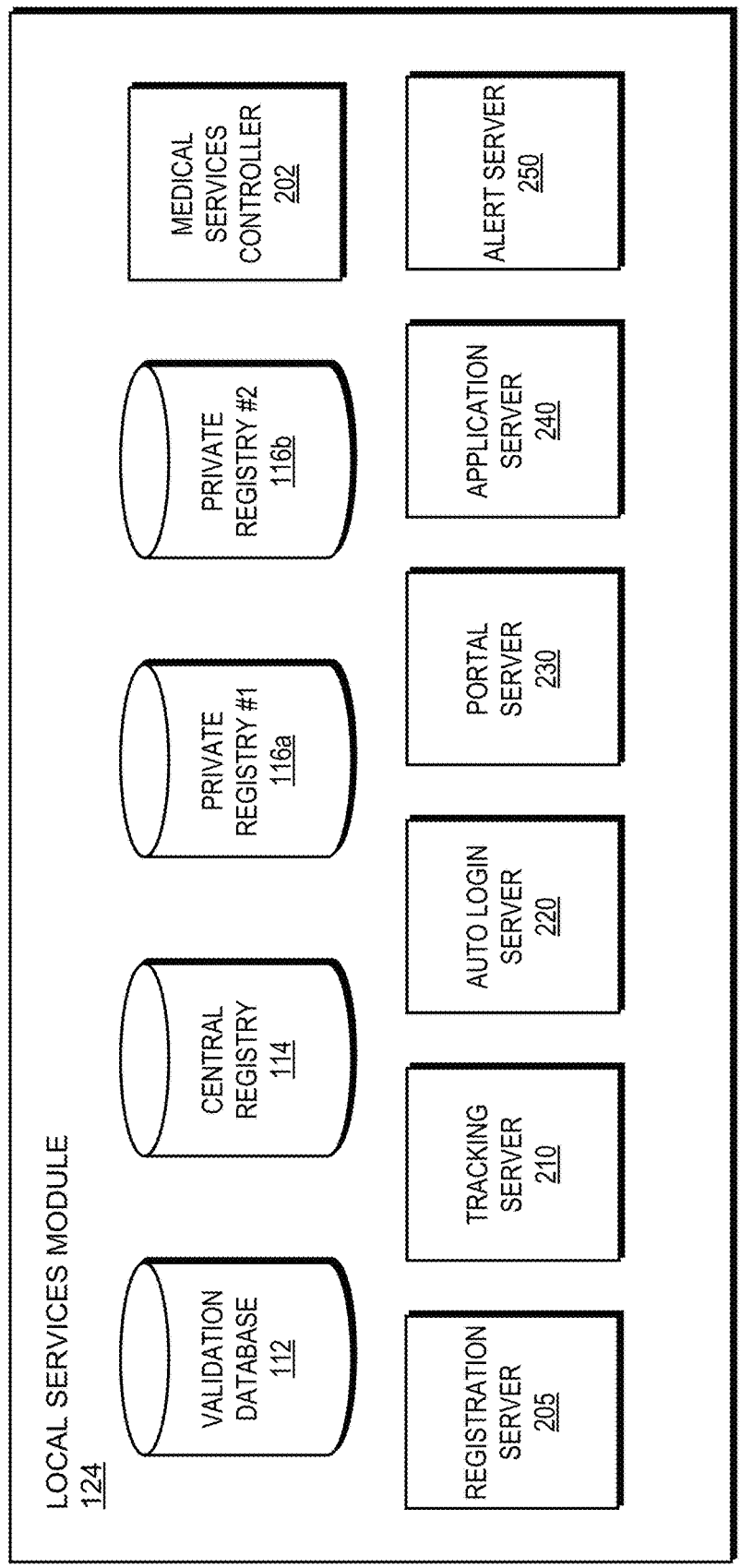
FIG. 2 is a block diagram illustrating one embodiment of a local services module in accordance with the present invention.

The Reader 108 is further communicatively coupled to the network 110 in order to receive and/or transmit information to remote databases for remote authentication. In an alternative embodiment, the Reader 108 includes a non-volatile data storage that can be synchronized with one or more remote databases 112 or registries 114, 116a, 116b (FIG. 2). Such an embodiment alleviates the need for a continuous connection to the network 110 and allows the Reader 108 to operate in a standalone mode and for the local data storage to be updated when a connection is available. For example, a standalone Reader 108 can periodically download updated registry entries and perform authentication locally without any remote lookup.

The network 110 provides communication between the Reader 108 and the computing device 120, local services module 124, and third party link module 126. For example, a communication channel 156 couples the computing device 120 to the network 110. For example, the communication channel 156 is a wired or wireless connection. In alternative embodiments, one or more of these connections may not be present or different or additional network connections may be present. In one embodiment, the network 110 uses standard communications technologies and/or protocols. Thus, the network 110 can include links using technologies such as Ethernet, 802.11, 802.16, integrated services digital network (ISDN), digital subscriber line (DSL), asynchronous transfer mode (ATM), etc. Similarly, the networking protocols used on the network 110 can include the transmission control protocol/Internet protocol (TCP/IP), the hypertext transport protocol (HTTP), the simple mail transfer protocol (SMTP), the file transfer protocol (FTP), etc. The data exchanged over the network 110 can be represented using technologies and/or formats including the hypertext markup language (HTML), the extensible markup language (XML), etc. In addition, all or some of links can be encrypted using conventional encryption technologies such as the secure sockets layer (SSL), Secure HTTP and/or virtual private networks (VPNs). In another embodiment, the entities can use custom and/or dedicated data communications technologies instead of, or in addition to, the ones described above.

Similarly, the network 130 provides communication between the local services module 124 and third party site 140. In alternative embodiments, one or more of these connections may not be present or different or additional network connections may be present. In one embodiment, the network 130 uses standard communications technologies and/or protocols. Thus, the network 130 can include links using technologies such as Ethernet, 802.11, 802.16, integrated services digital network (ISDN), digital subscriber line (DSL), asynchronous transfer mode (ATM), etc. Similarly, the networking protocols used on the network 110 can include the transmission control protocol/Internet protocol (TCP/IP), the hypertext transport protocol (HTTP), the simple mail transfer protocol (SMTP), the file transfer protocol (FTP), etc. The data exchanged over the network 110 can be represented using technologies and/or formats including the hypertext markup language (HTML), the extensible markup language (XML), etc. In addition, all or some of links can be encrypted using conventional encryption technologies such as the secure sockets layer (SSL), Secure HTTP and/or virtual private networks (VPNs). In another embodiment, the entities can use custom and/or dedicated data communications technologies instead of, or in addition to, the ones described above.

FIG. 2 is a block diagram illustrating a local services module 124, which includes one or more external databases including a validation database 112, a Central Registry 114 and one or more private registries 116a, 116b. The local services module 124 also includes a medical services controller 202, a registration server 205, a tracking server 210, an auto login server 220, a quality assurance server 240, and an internet portal server 250.

The validation database 112 stores additional information that may be used for authorizing a transaction to be processed at the Reader 108. For example, in purchase transactions, the validation database 112 is a credit card validation database that is separate from the merchant providing the sale. Alternatively, a different database may be used to validate different types of purchasing means such as a debit card, ATM card, or bank account number. As another example in healthcare systems, the validation database 112 is a medical record number validation database that separate from the healthcare institution providing the patient care, which provides confirmation of the patient's identification.

The registries 114, 116a, 116b are securely-accessible databases coupled to the network 110 that store, among other items, PDK, Notary, and Reader information. In one embodiment, the registries 114, 116a, 116b do not store biometric information. In an alternative embodiment, the registries 114, 116a, 116b store biometric information in an encoded format that can only be recovered using an algorithm or encoding key stored in the PDK 102. Information stored in the registries 114, 116a, 116b can be accessed by the Reader 108 via the network 110 for use in the authentication process. There are two basic types of registries 114, 116a, 116b illustrated: private registries 116a, 116b and the Central Registry 114. Private registries 116a, 116b are generally established and administered by their controlling entities (e.g., a health care provider, business authority, or other entity administering authentication). Private registries 116a, 116b can be custom configured to meet the specialized and independent needs of each controlling entity. The Central Registry 114 is a single highly-secured, centrally-located database administered by a trusted third-party organization. In one embodiment, all PDKs 102 are registered with the Central Registry 114 and may be optionally registered with one or more selected private registries 116a, 116b. In alternative embodiments, a different number or different types of registries 114, 116a, 116b may be coupled to the network 110.

In one embodiment, a registry 114, 116 or the database 112 includes one or more records. A record includes login information associated with one or more applications. For example, the record includes a PDK ID 312, an application identifier, an application username and an application password. When the PDK 102 is identified by a Reader, data from the registry profile is communicated to the local services module 124 and used to allow a user to login or access an application using the data stored in the registry profile. In one embodiment, different records in the registry 114, 116 or database 112 are encrypted using a registry key that is also stored in the PDK 102 to prevent access to a record without the PDK 102. One embodiment of launching, or accessing, application using a registry profile is further described below in conjunction with FIGS. 18-20.

The medical services controller 202 enables communication between the servers and modules of the local services module 124 and third party link module 126 with the computing device 120. In one embodiment, the medical services controller 202 receives information and requests from the computing device 120 via the network 110. In another embodiment, the medical services controller 202 coordinates the operation of the various servers and modules of the local services module 124 and third party link module 126. For example, when a patient registration request is received from the Reader 108, the medical services controller 202 routes the request to the registration server 205 and forwards registration confirmation to the appropriate destination, such as the computing device 120.

The registration server 205 automates the process of registering new patients and ensures that a patient never needs to register more than once. In one embodiment, the registration server 205 resides in the local services module 124, which is coupled to the network via signal line 158. In one embodiment, the registration server 205 is coupled to the validation database 112, central registry 114 and private registries 116a, 116b. The registration server 205 receives patient registration requests from Readers 108 via the network 110 and sends information to the computing device 120 also via the network 110.

The tracking server 210 enables real-time tracking of individuals, equipment and supplies. In one embodiment, the tracking server 210 resides in the local services module 124, which is coupled to the network 110 via signal line 158. The tracking server 210 receives information from the Readers 108 and sends information back to the Readers 108 and PDK 102. One embodiment of the tracking server 210 is described in more detail below with reference to FIG. 15.

The auto login server 220 allows for automated logging in of providers into the healthcare computer system. In one embodiment, the auto login server 220 resides in the local services module 124 and is coupled to the validation database 112, central registry 114 and private registries 116a, 116b. The auto login server receives login requests from the Readers 108 and sends login authorization to the computing device 120. One embodiment of the auto login server 220 is described in more detail below with reference to FIG. 17.

The portal server 230 exchanges data between the local services module 124 and one or more third party sites 140. For example, the portal server 230 includes identifiers associated with one or more third party sites 140 to identify a third party site 140 and enable access to data maintained by the third party site 140. In one embodiment, the portal server 230 also modifies the format of data received from a third party site 140 to expedite use of the received data by another component, such as the application server 240 or a computing device 120 coupled to the local services module 124.

The application server 240 includes data that, when executed by a processor, implements one or more applications to provide one or more types of functionality. In one embodiment, the application server 240 is included in the local services module 124. Additionally, in one embodiment, the application server 240 communicates with one or more third party sites 140 via a signal line 164 and the network 130, which communicates with the third party site 140 via a communication channel 172. This allows the application server 250 to communicate data from the third party site 140 to the computing device 120. One embodiment of the application server 240 is described in more detail below with reference to FIG. 24. Such third party services may include accessing a patient's virtual database records or insurance information or sending prescription requests to remote pharmacies. More detailed information describing the components and functions of these servers is described in more detail below.

The alert server 250 provides automatic updates and alerts for monitored patients or other entities. The alert server 250 receives information from Readers 108 and sends information to the computing device 120. In one embodiment, the alert server 250 resides in the local services module 124. In one embodiment, the alert server 250 receives data from the tracking server 210 to allow generation of updates or alerts based on the location of a PDK 102.

Figure 3:
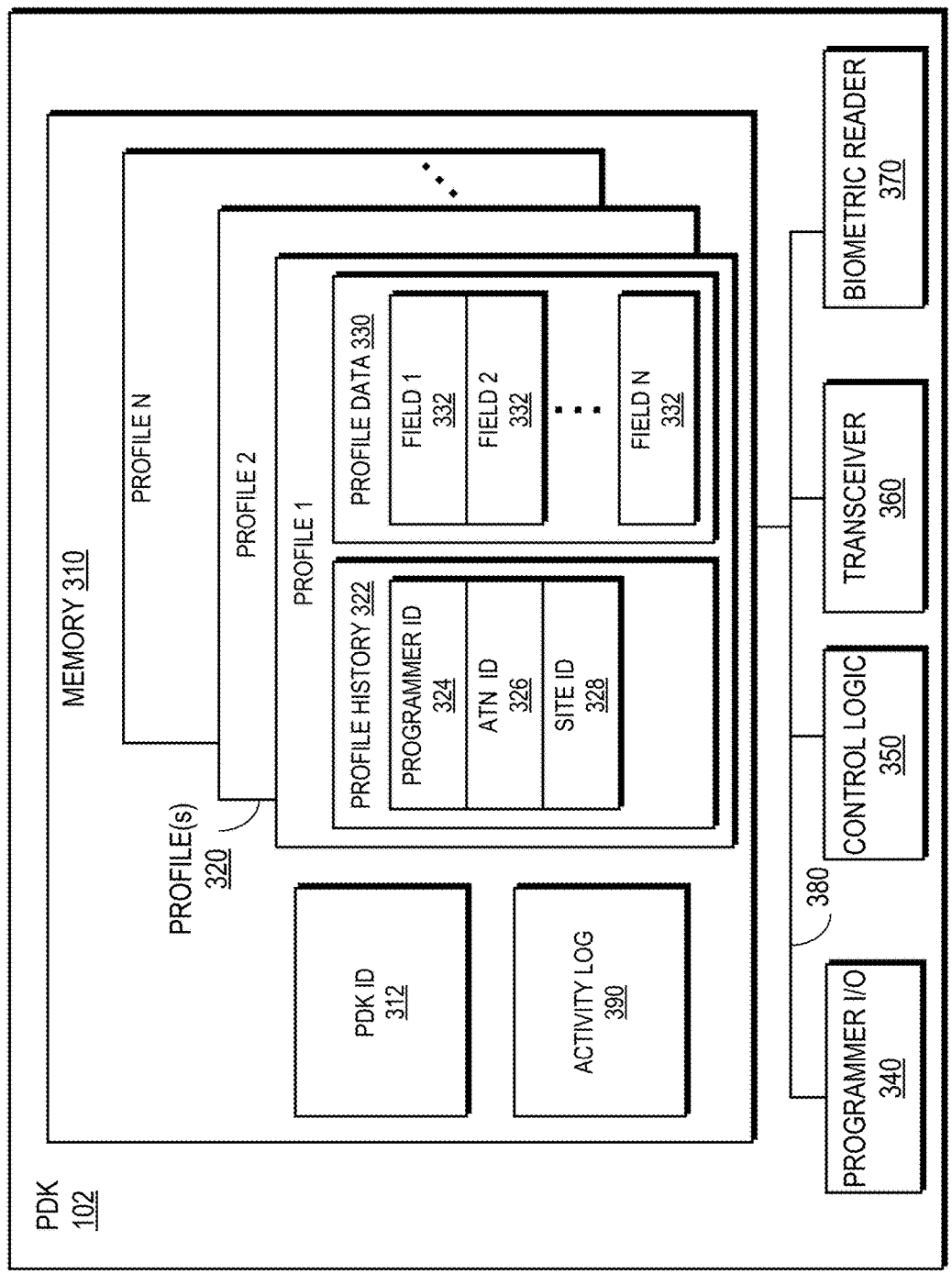
FIG. 3 is a block diagram illustrating one embodiment of a Personal Digital Key (PDK) in accordance with the present invention.

Turning now to FIG. 3, an example embodiment of a PDK 102 is illustrated. The PDK 102 comprises a memory 310, a programmer I/O 340, control logic 350, a transceiver 360 and a biometric reader 370 coupled by a bus 380. The PDK 102 can be standalone as a portable, physical device or can be integrated into commonly carried items. For example, a PDK 102 can be integrated into a portable electronic device such as a cell phone, Personal Digital Assistant (PDA), or GPS unit, an employee identification tag or badge, clothing, or jewelry items such as watches, rings, necklaces or bracelets. In one embodiment, the PDK 102 can be, for example, about the size of a Subscriber Identity Module (SIM) card and be as small as a square inch in area or less. In another embodiment, the PDK 102 can be easily contained in a pocket, on a keychain, or in a wallet. In yet another embodiment, a PDK 102 can be integrated into a sticker, tag or other item attachable to various items or equipment. In other embodiments, the PDK 102 can be integrated into a clipboard, patient wristband or other patient identification tags or badges. In some embodiments, where the PDK 102 is attached to equipment for tracking purposes, the PDK 102 also includes a button or switch that can be activated or deactivated to indicate whether the equipment is in use.

The memory 310 can be a read-only memory, a once-programmable memory, a read/write memory or any combination of memory types including physical access secured and tamperproof memories. The memory 310 typically stores a unique PDK ID 312, an activity log 390 and one or more profiles 320. The PDK ID 312 comprises a public section and a private section of information, each of which can be used for identification and authentication. In one embodiment, the PDK ID 312 is stored in a read-only format that cannot be changed subsequent to manufacture. The PDK ID 312 is used as an identifying feature of a PDK 102 and distinguishes between PDKs 102 in private 116 or Central 114 registry entries. In an alternative embodiment, the registries can identify a PDK 102 by a different ID than the PDK ID 412 stored in the PDK 102, or may use both the PDK ID 312 and the different ID in conjunction. The PDK ID 312 can also be used in basic PDK authentication to ensure that the PDK 102 is a valid device.

The activity log 390 stores information associated with various activities of the PDK. For example, if the PDK 102 is a patient's PDK, the activity log 390 stores information identifying the patient's location throughout various times. In one embodiment, the activity log 390 keeps track of each time a patient visits a healthcare facility or each time a doctor or nurse visits a department within the healthcare facility. In another embodiment, the activity log 390 stores the patient's location throughout various points as the patient is in the provider's facility. Similarly, the if PDK 102 is attached to a piece of equipment or a cart of supplies, the activity log 390 stores location information as well. In another embodiment, if the PDK 102 is that of a provider, the activity log 390 stores information associated with the provider's rounds, i.e. each time a provider visits a certain patient or uses a particular medical device.

The profile fields 320 can be initially empty at the time of manufacture but can be written to by authorized individuals (e.g., a Notary) and/or hardware (e.g., a Programmer). In one embodiment, each profile 320 comprises a profile history 322 and profile data 330. Many different types of profiles 320 are possible. A biometric profile, for example, includes profile data 330 representing physical and/or behavioral information that can uniquely identify the PDK owner. A PDK 102 can store multiple biometric profiles, each comprising a different type of biometric information. In one embodiment, the biometric profile 320 comprises biometric information transformed by a mathematical operation, algorithm, or hash that represents the complete biometric information (e.g., a complete fingerprint scan). In one embodiment, a mathematical hash is a "one-way" operation such that there is no practical way to re-compute or recover the complete biometric information from the biometric profile. This both reduces the amount of data to be stored and adds an additional layer of protection to the user's personal biometric information. In one embodiment, the biometric profile is further encoded using an encoding key and/or algorithm that is stored with the biometric profile data. Then, for authentication, the biometric profile data and the encoding key and/or algorithm are passed to the Reader 108.

In one embodiment, the PDK 102 also stores one or more biometric profile "samples" associated with each biometric profile. The biometric profile sample is a subset of the complete profile that can be used for quick comparisons of biometric data. In one embodiment, the profile samples can be transmitted over a public communication channel or transmitted with reduced level of encryption while the full biometric profiles are only transmitted over secure channels. In the case of fingerprint authentication, for example, the biometric profile sample may represent only small portion area of the full fingerprint image. In another embodiment, the fingerprint profile sample is data that describes an arc of one or more lines of the fingerprint. In yet another embodiment, the fingerprint profile sample can be data representing color information of the fingerprint.

In another embodiment, the stored profiles 320 include a PIN profile that stores one or more PINs or passwords associated with the PDK owner. Here, the number or password stored in the PIN profile can be compared against an input provided by the user at the point of transaction to authenticate the user. In one embodiment, a PIN profile sample is also stored with the PIN profile that comprises a subset of the full PIN. For example, a PIN profile sample can be only the first two numbers of the PIN that can be used to quickly compare the stored PIN profile to a PIN obtained at the point of transaction.

In yet another embodiment, the PDK 102 stores a picture profile that includes one or more pictures of the PDK owner. In a picture profile authentication, the picture stored in the PDK 102 is transmitted to a display at the point of transaction to allow an administrator (e.g., a clerk or security guard) to confirm or reject the identity of the individual requesting the transaction. In another embodiment, an image is captured of the individual at the point of transaction and compared to the picture profile by an automated image analysis means. Furthermore, picture profiles could be used, for example, in place of conventional passports or drivers licenses to authenticate the identity of an individual and allow for remote identification of individuals. For example, a police officer following a vehicle could obtain an image and identity of the driver while still maintaining a safe distance from the vehicle. In the hospitality industry, a host could greet a guest at the door of a hotel, casino or restaurant and easily recognize the guest by obtaining the guest's picture profile as he/she enters. In healthcare, a doctor or nurse can ensure that he or she is administering the correct medication to the right patient by looking at the profile picture associated with that patient.

A registry or database profile typically stores information associating the user with a registry. The registry profile can be used to determine if the individual is associated with the controlling entity for that registry and if different types of transactions are authorized for the individual. A registry profile can further include additional user information for use with the registry. For example, a private registry profile associated with a particular merchant may include a credit card number that the user has selected as a default for that merchant. In one embodiment, a profile can further include spending limits that limits the amount of purchases a user can make with a particular vendor or using a particular profile.

A registry profile may include one or more service blocks identifying a registry 114, 116 or database 112 in the local services module 124 and identify a record within the identified registry 114, 116 or database 112. In one embodiment, the service block includes a registry identifier, a record identifier to specify a record within the identified registry and a registry key. In one embodiment, different records in the registry 114, 116 or database 112 are encrypted using registry key that is stored in the PDK 102 to prevent access to a record without the PDK 102. In one embodiment, one or more processes implemented by the control logic 350 are used to identify a service block within a registry profile, allowing access to specific service blocks. This also allows application of service block-specific security by making different service blocks independent of each other. One embodiment of launching, or accessing, an application using a registry profile is further described below in conjunction with FIGS. 18-21.

Additionally, a profile may include application specific information, allowing a registry profile to be used to launch or access an application and application specific information included in the registry profile or in another profile to be accessed by the application. This allows the PDK 102 to include data customizing operation of an application. For example, a patient of a healthcare facility may have a PDK 102 having a profile that stores the patient's medical records, allowing a computing device 120 to retrieve the patient's medical records when the PDK 102 communicates with a Reader 108 coupled to the computing device 120. As another example, a PDK 102 profile includes user preference data, allowing configuration of an application executed by a computing device 120 by communicating the user preference data from the PDK 102 to the computing device 120 via a Reader 108 coupled to the computing device 120. Hence, in addition to including data used for authentication or security, a PDK 102 may include profiles for customizing operation of applications or for storing data for subsequent access.

A profile can further include personal identification information such as name, address, phone number, etc., insurance information, credit/debit card information, or information regarding visited providers. This information can be useful for certain types of transactions. For example, patient office visits, a PDK 102 can automatically transmit address, insurance and billing information to the Reader 108 at the conclusion of the office visit.

Figure 25:
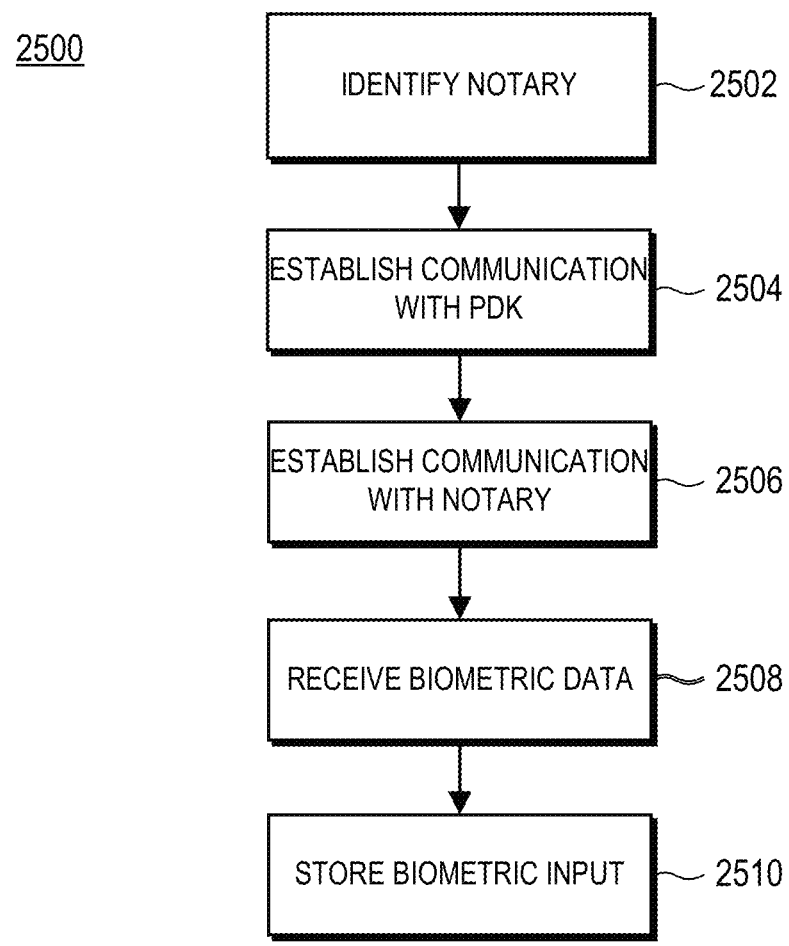
FIG. 25 is a flow chart of a method for initially storing data on a PDK in accordance with the present invention.

Generally, some types of profile information (e.g., a biometric profile) can only be acquired during a trusted initialization process that is administered by a trusted Notary. In one embodiment, other secure information such as medical conditions are also stored to the PDK 102 in the presence of a Notary. Alternatively, certain types of low-risk information can be added by the user without a Notary, such as, for example a change of address. In another embodiment, once an initial profile has been stored to the PDK 102, a user can add information to the PDK 102 using a Programmer without a Notary through self-authentication. For example, in one embodiment, a PDK 102 that has a stored biometric profile can be "unlocked" by providing a matching biometric input. Then, once unlocked, the user can add or remove additional profiles, insurance cards, personal information, etc. to the PDK 102 using a Programmer. For example, in one embodiment, a user that has unlocked his/her own PDK 102 can store additional biometric information (such as fingerprint information for other fingers) in his/her PDK 102. In another example, a user that cancels an insurance card, can unlock his/her PDK 102 to remove the insurance card information. In another embodiment, the user can make copies of the PDK 102 or move profiles from one PDK 102 to another once the PDK 102 is unlocked. FIG. 25 provides additional description of acquisition of an initialization process.

The profile history 322 includes a programmer ID field 324, a Notary ID 326, and a site ID field 328. The profile history 322 relates to the specific hardware, Notary, and site used at the time the profile data was created and stored to the PDK. Typically each profile 320 stores its specific profile history 322 along with the profile data 330. The profile history 322 can be recalled for auditing purposes at a later time to ensure the credibility of the stored data. In one embodiment, transaction history can also be stored to the PDK memory 310. Here, the PDK 102 stores information associated with any transactions made with the PDK 102 such as the healthcare provider, reason for office visit and insurance used, etc.

The PDK 102 also includes a programmer I/O 340 that provides an interface to a trusted Programmer (not shown). The Programmer comprises trusted hardware that is used to program the memory 310 of the PDK 102. An example embodiment of a Programmer is described in U.S. patent application Ser. No. 11/744,832 to John Giobbi, et al., entitled "Personal Digital Key Initialization and Registration For Secure Transaction" and filed on May 5, 2007, the entire contents of which are incorporated herein by reference. The programmer I/O 340 can be, for example, a USB interface, serial interface, parallel interface, or any other direct or wireless link for transferring information between the PDK 102 and the Programmer. When coupled to the Programmer, the programmer I/O 340 receives initialization data, registration data or other information to be stored in the memory 310.

The control logic 350 coordinates between functions of the PDK 102. In one embodiment, the control logic 350 facilitates the flow of information between the programmer I/O 340, transceiver 360 and memory 310. The control logic 350 can further process data received from the memories 310, programmer I/O 340 and transceiver 360. Note that the control logic 350 is merely a grouping of control functions in a central architecture, and in other embodiments, the control functions can be distributed between the different modules of the PDK 102. The operation of the control logic will be understood to those skilled in the art based on the description below corresponding to FIGS. 8-11D.

Optionally, the PDK 102 can also include a built in biometric reader 370 to acquire a biometric input from the user. The biometric reader 370 is configured to obtain a representation of physical or behavioral characteristics derived from the individual. The biometric input can be used to unlock the PDK 102 for profile updates, or for various types of authentication. For example, in one embodiment, a biometric input is received by the PDK 102 and compared to stored biometric information. Then, if the user is authenticated, the PDK 102 can indicate to the Reader 108 that the user is authenticated and transmit additional information (e.g., a credit card number) needed to complete a transaction.

The transceiver 360 is a wireless transmitter and receiver for wirelessly communicating with a Reader 108 or other wireless device. The transceiver 360 sends and receives data as modulated electromagnetic signals. Moreover, the data can be encrypted by the transceiver 360 and transmitted over a secure link. Further, the transceiver 360 can actively send connection requests, or can passively detect connection requests from another wireless source. In one embodiment, the transceiver 360 is used in place of a separate programmer I/O 340 and is used to wirelessly communicate with the Programmer for programming. In one embodiment, the transceiver 360 is adapted to communicate over a range of up to around 5 meters.

Figure 4:
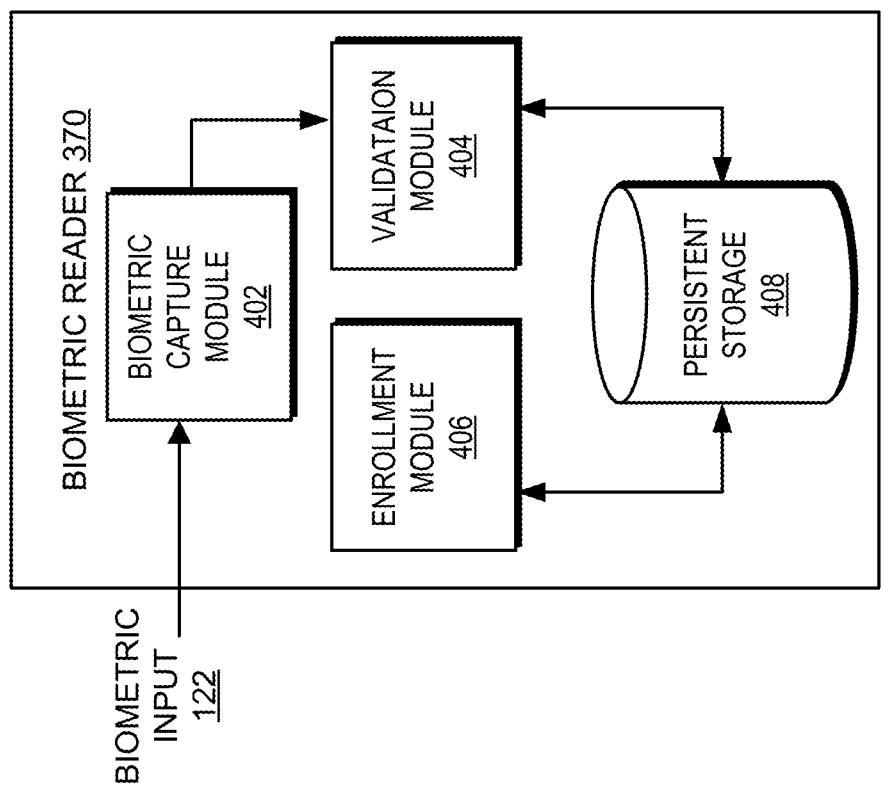
FIG. 4 is a block diagram illustrating one embodiment of a biometric reader of a PDK in accordance with the present invention.

FIG. 4 is a block diagram illustrating one embodiment of a biometric reader 370 of a PDK 102. The biometric reader 370 includes a biometric capture module 402, a validation module 404, an enrollment module 406 and persistent storage 408. In one embodiment, the enrollment module 406 registers a user with a PDK 102 by persistently storing biometric data associated with the user. Further, enrollment module 406 registers PDK 102 with a trusted authority by providing the code (e.g., device ID) to the trusted authority. Or conversely, the trusted authority can provide the code to PDK 102 to be stored therein.

The biometric capture module 402 comprises a scan pad to capture scan data from a user's fingerprint (e.g., a digital or analog representation of the fingerprint). Other embodiments of the biometric capture module 402 includes retinal scanners, iris scanners, facial scanner, palm scanners, DNA/RNA analyzers, signature analyzers, cameras, microphones, and voice analyzers to capture other identifying biometric data. Using the biometric data, validation module 404 determines whether the user's fingerprint, or other biometric data, matches the stored biometric data from enrollment. Conventional techniques for comparing fingerprints can be used. For example, the unique pattern of ridges and valleys of the fingerprints can be compared. A statistical model can be used to determine comparison results. Validation module 404 can send comparison results to control logic 350 of the PDK 102.

In other embodiments, validation module 404 can be configured to capture biometric data for other human characteristics. For example, a digital image of a retina, iris, and/or handwriting sample can be captured. In another example, a microphone can capture a voice sample.

Persistent storage 408 persistently stores biometric data from one or more users which can be provided according to specific implementations. In one embodiment, at least some of persistent storage 408 is a memory element that can be written to once but cannot subsequently be altered. Persistent storage 408 can include, for example, a ROM element, a flash memory element, or any other type of non-volatile storage element. Persistent storage 508 is itself, and stores data in, a tamper-proof format to prevent any changes to the stored data. Tamper-proofing increases reliability of authentication because it does not allow any changes to biometric data (i.e., allows reads of stored data, but not writes to store new data or modify existing data). Furthermore, data can be stored in an encrypted form.

In one embodiment, persistent storage 408 also stores the code that is provided by the PDK 102 responsive to successful verification of the user. Further, in some embodiments persistent storage 408 stores other data utilized during the operation of PDK 102. For example, persistent storage 408 can store encryption/decryption keys utilized to establish secure communications links.

An example embodiment of PDK 102 including a biometric reader is described in U.S. patent application Ser. No. 11/314,199 to John Giobbi, et al., entitled "Biometric Personal Data Key (PDK) Authentication", the entire contents of which are incorporated herein by reference.

Figure 5:
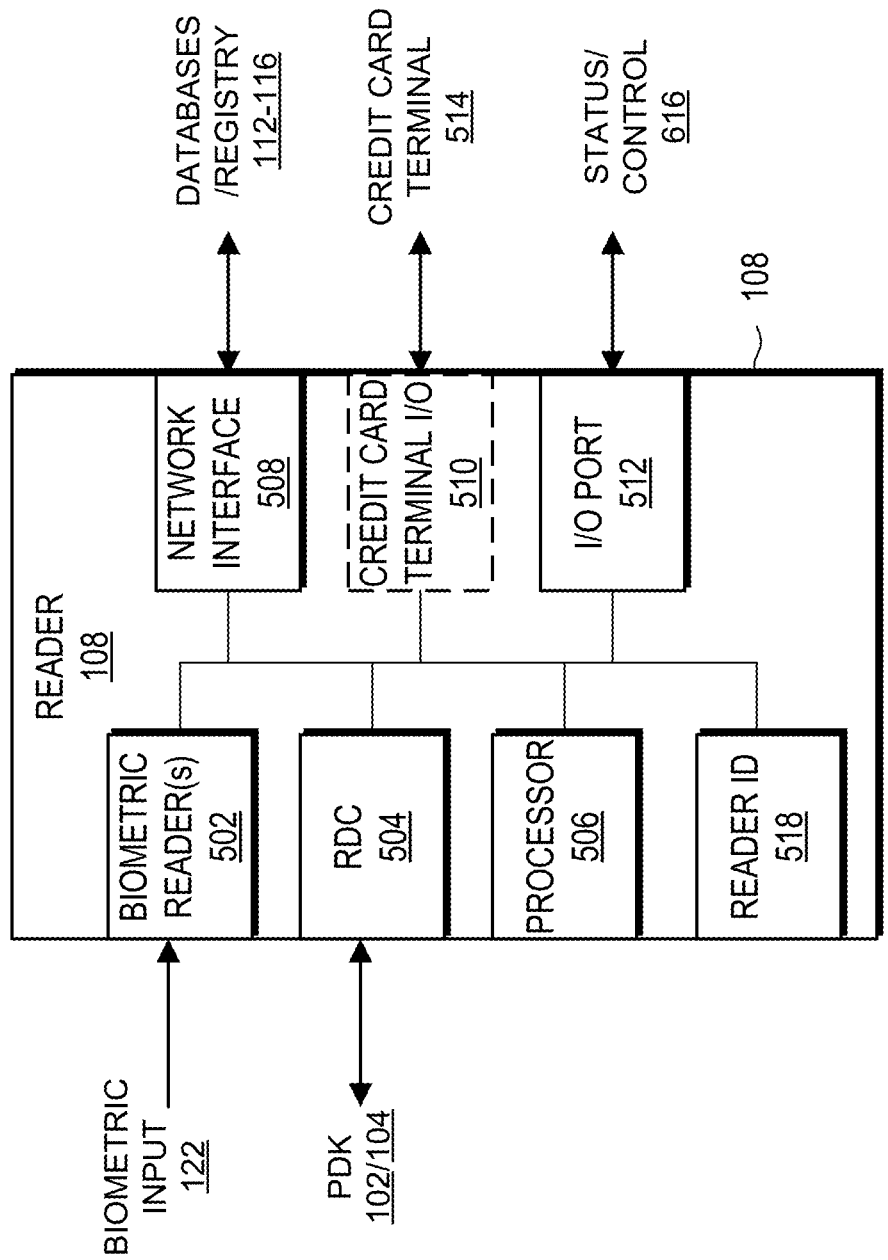
FIG. 5 is a block diagram illustrating one embodiment of a reader in accordance with the present invention.

Turning now to FIG. 5, an example embodiment of a Reader 108 is illustrated. The embodiment includes one or more biometric readers 502, a receiver-decoder circuit (RDC) 504, a processor 506, a network interface 508, an I/O port 612, optionally a credit card terminal I/O 510 and a reader ID 518. In alternative embodiments, different or additional modules can be included in the Reader 108.

The RDC 504 provides the wireless interface to the PDK 102. Generally, the RDC 504 wirelessly receives data from the PDKs 102 in an encrypted format and decodes the encrypted data for processing by the processor 506. An example embodiment of an RDC is described in U.S. patent application Ser. No. 11/292,330 entitled "Personal Digital Key And Receiver/Decoder Circuit System And Method", the entire contents of which are incorporated herein by reference. Encrypting data transmitted between the PDK 102 and Reader 108 minimizes the possibility of eavesdropping or other fraudulent activity. In one embodiment, the RDC 504 is also configured to transmit and receive certain types of information in an unencrypted or public format.

The biometric reader 502 receives and processes the biometric input 122 from an individual and is configured to obtain a representation of physical or behavioral characteristics derived from the individual. In one embodiment, the biometric reader 602 is a fingerprint scanner. Here, the biometric reader 502 includes an image capture device adapted to capture the unique pattern of ridges and valleys in a fingerprint also known as minutiae. Other embodiments of biometric readers 502 include retinal scanners, iris scanners, facial scanner, palm scanners, DNA/RNA analyzers, signature analyzers, cameras, microphones, and voice analyzers. Furthermore, the Reader 108 can include multiple biometric readers 502 of different types. In one embodiment, the biometric reader 502 automatically computes mathematical representations or hashes of the scanned data that can be compared to the mathematically processed biometric profile information stored in the PDK 102.

The processor 506 can be any general-purpose processor for implementing a number of processing tasks. Generally, the processor 506 processes data received by the Reader 108 or data to be transmitted by the Reader 108. For example, a biometric input 122 received by the biometric reader 502 can be processed and compared to the biometric profile 420 received from the PDK 102 in order to determine if a transaction should be authorized. In different embodiments, processing tasks can be performed within each individual module or can be distributed between local processors and a central processor. The processor 506 further includes a working memory for use in various processes.

The network interface 508 is a wired or wireless communication link between the Reader 108 and one or more external databases such as, for example, a validation database 112, the Central Registry 114 or a private registry 116a, 116b. For example, in one type of authentication, information is received from the PDK 102 at the RDC 504, processed by the processor 506, and transmitted to an external database 112-116 through the network interface 508. The network interface 508 can also receive data sent through the network 110 for local processing by the Reader 108. In one embodiment, the network interface 508 provides a connection to a remote system administrator to configure the Reader 108 according to various control settings.

The I/O port 512 provides a general input and output interface to the Reader 108. The I/O port 512 may be coupled to any variety of input devices to receive inputs such as a numerical or alphabetic input from a keypad, control settings, menu selections, confirmations, and so on. Outputs can include, for example, status LEDs, an LCD, or other display that provides instructions, menus or control options to a user.

The credit card terminal I/O 510 optionally provides an interface to an existing credit card terminal 514. In embodiments including the credit card terminal I/O 510, the Reader 108 supplements existing hardware and acts in conjunction with a conventional credit card terminal 514. In an alternative embodiment, the functions of an external credit card terminal 514 are instead built into the Reader 108. Here, a Reader 108 can completely replace an existing credit card terminal 514.

In one embodiment, a Reader 108 is adapted to detect and prevent fraudulent use of PDKs that are lost, stolen, revoked, expired or otherwise invalid. For example, the Reader 108 can download lists of invalid PDKs IDs 312 from a remote database and block these PDKs 102 from use with the Reader 108. Furthermore, in one embodiment, the Reader 108 can update the blocked list and/or send updates to remote registries 114, 116a, 116b or remote Readers 108 upon detecting a fraudulently used PDK 102. For example, if a biometric input 122 is received by the Reader 108 that does not match the biometric profile received from the PDK 102, the Reader 108 can obtain the PDK ID 312 and add it to a list of blocked PDK IDs 312. In another embodiment, upon detecting fraudulent use, the Reader 108 can send a signal to the PDK 102 that instructs the PDK 102 to deactivate itself. The deactivation period can be, for example, a fixed period of time, or until the rightful owner requests re-activation of the PDK 102. In yet another embodiment, the Reader 108 can send a signal instructing the fraudulently obtained PDK 102 to send alarm signals indicating that the PDK 102 a stolen device. Here, a stolen PDK 102 can be tracked, located and recovered by monitoring the alarm signals. In one embodiment, the Reader 108 stores biometric or other identifying information from an individual that attempts to fraudulently use a PDK 102 so that the individual's identity can be determined.

The reader ID 518 is memory that stores the reader's unique identification number. The memory can be a read-only memory, a once-programmable memory, a read/write memory or any combination of memory types including physical access secured and tamperproof memories. The reader ID 518 plays an integral role in the process for tracking equipment, supplies and individuals as will be explained in more detail below.

Generally, the Reader 108 is configured to implement at least one type of authentication prior to enabling a transaction. In many cases, multiple layers of authentication are used. A first layer of authentication, referred to herein as "device authentication," begins any time a PDK 102 moves within range of a Reader 108. In device authentication, the Reader 108 and the PDK 102 each ensure that the other is valid based on the device characteristics, independent of any profiles stored in the PDK 102. In some configurations, when fast and simple authentication is desirable, only device authentication is required to initiate the transaction. For example, a Reader 108 may be configured to use only device authentication for office visit check-ins. The configuration is also useful in other types of low risk transactions where speed is preferred over additional layers of authentication.

Other configurations of the Reader 108 require one or more additional layers of authentication, referred to herein as "profile authentication" based on one or more profiles stored in the PDK 102. Profile authentication can include, for example, a biometric authentication, a PIN authentication, a photo authentication, a registry authentication, etc. or any combination of the above authentication types. Profile authentications are useful when a more exhaustive authentication process is desired, for example, for invasive patient treatments or drug administration.

Figure 6:
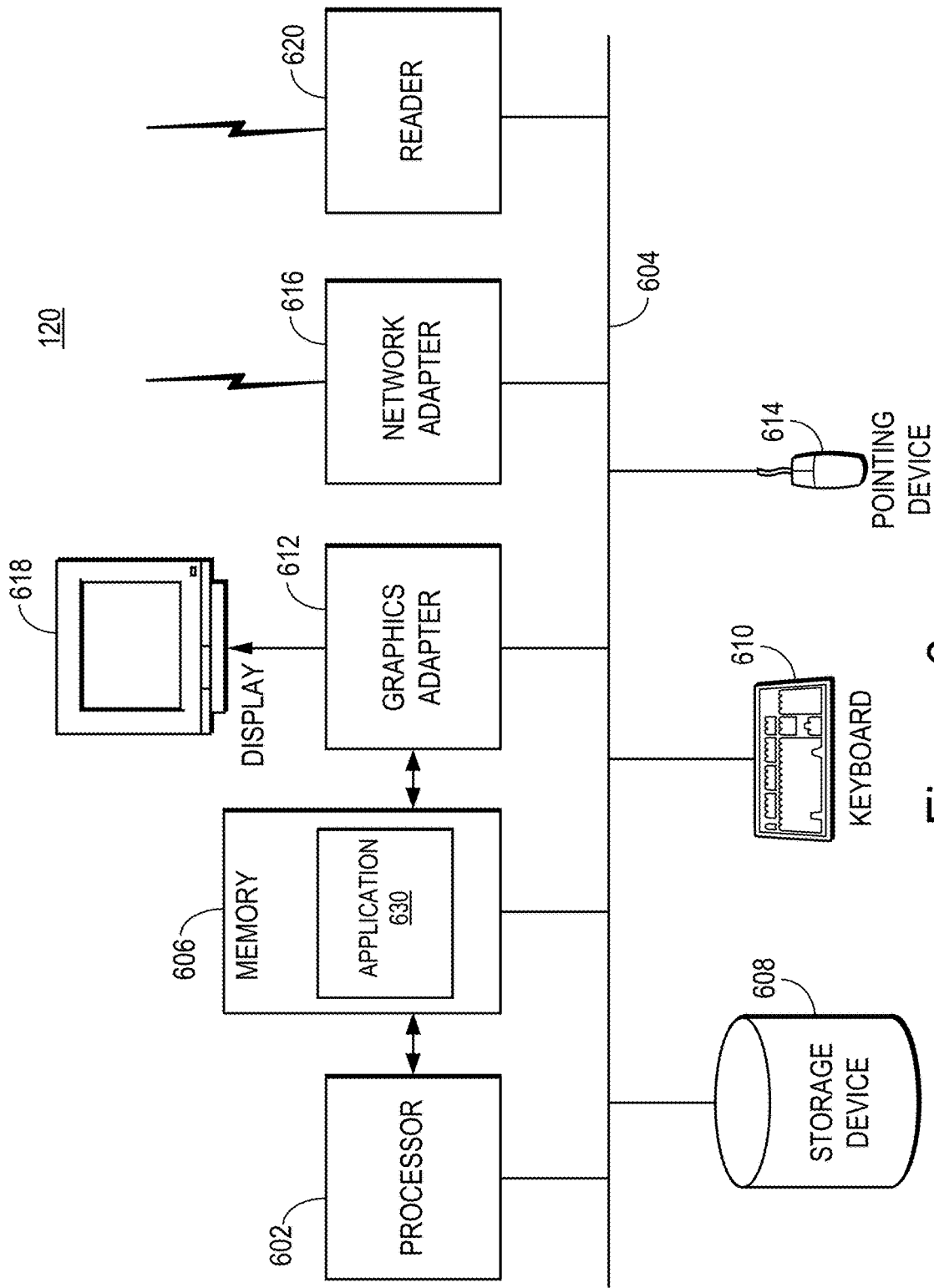
FIG. 6 is a block diagram illustrating one embodiment of a computing device in accordance with the present invention.

FIG. 6 is a high-level block diagram of one embodiment of a computing device 120. In one embodiment, the computing device 120 is a personal computer. In another embodiment, the computing device 120 is a smart phone or other mobile computing and communication device. Illustrated are at least one processor 602 coupled to a bus 604. Also coupled to the bus 604 are a memory 606, a storage device 608, a keyboard 610, a graphics adapter 612, a pointing device 614, a network adapter 616 and a reader 620. In one embodiment, the functionality of the bus 604 is provided by an interconnecting chipset. A display device 618 is coupled to the graphics adapter 612.

The memory 606 includes an application 630. In one embodiment, the application 630 enables the computing device 120 to communicate with the local services 124. In another embodiment, the application 630 processes information and data received from the readers 620 and various modules and servers of the local services 124 and third party link module 126.

The storage device 608 is any device capable of holding data, like a hard drive, compact disk read-only memory (CD-ROM), DVD, or a solid-state memory device. The memory 606 holds instructions and data used by the processor 602. The pointing device 614 may be a mouse, track ball, or other type of pointing device, and is used in combination with the keyboard 610 to input data into the computing device 120. The graphics adapter 612 displays images and other information on the display device 618. The network adapter 616 couples the computing device 120 to a local or wide area network.

As is known in the art, a computing device 120 can have different and/or other components than those shown in FIG. 6. In addition, the computing device 120 can lack certain illustrated components. In one embodiment, a computing device 120 lacks a keyboard 610, a pointing device 614, a graphics adapter 612, and/or a display device 618. Moreover, the storage device 608 can be local and/or remote from computing device 120 (such as embodied within a storage area network (SAN)). The reader 620 includes all or some of the components as the Reader 108 described above in conjunction with FIG. 5.

As is known in the art, the computing device 120 is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device 608, loaded into the memory 606, and executed by the processor 602.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

Figure 7:
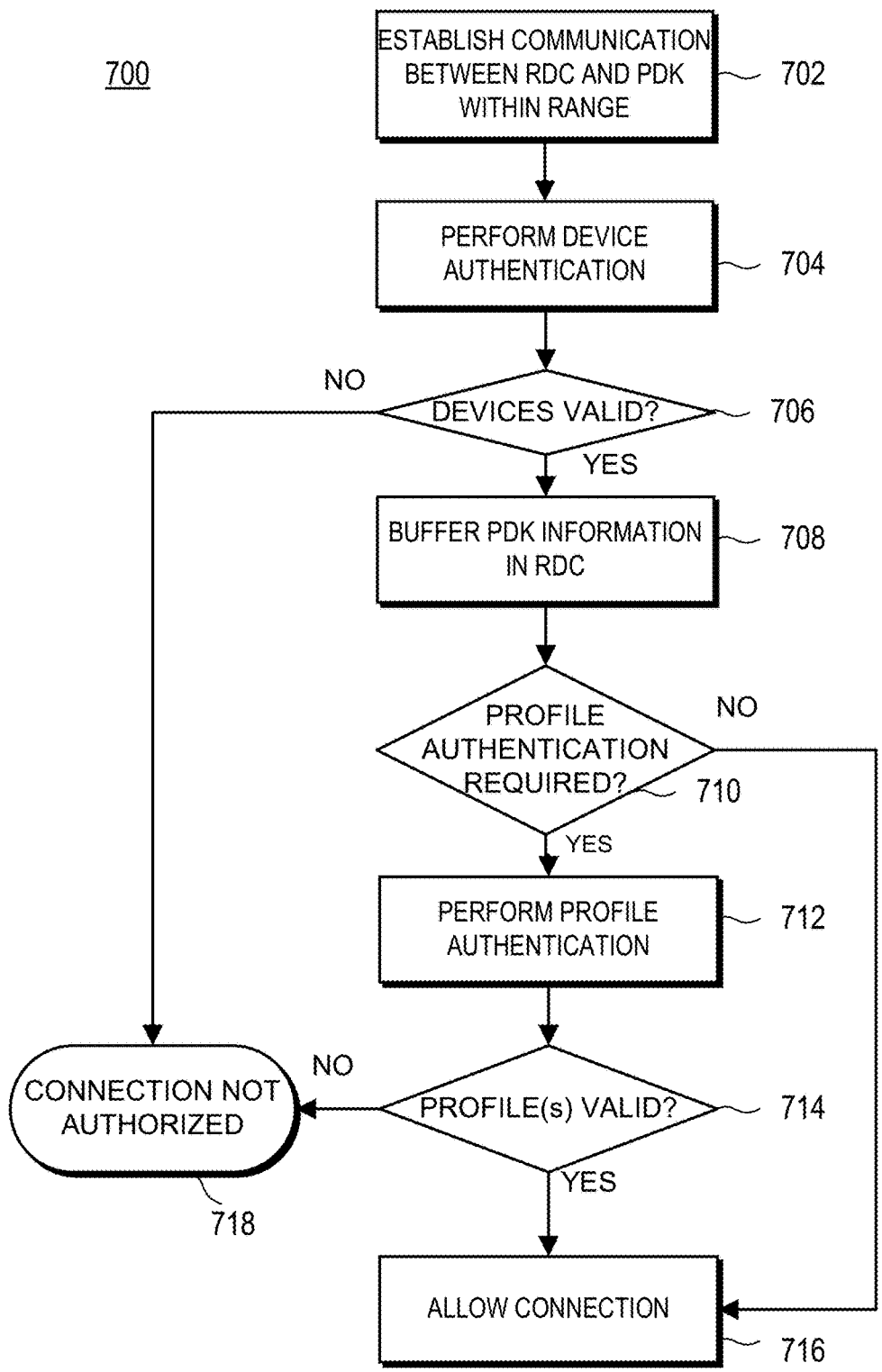
FIG. 7 is a flowchart of a method for authorizing a communication connection using secure authentication in accordance with the present invention.

FIG. 7 is a flowchart illustrating one embodiment of a process for authorizing a communication connection using secure authentication. When a PDK 102 comes within range of a Reader 108, communication is automatically established 702 between the RDC 504 of the Reader 108 and the PDK 102. It should be noted that the processes described herein with regards to Reader 108 may be also performed with reader 620 of the computing device 120.

In one embodiment, the RDC 504 continually transmits beacons that are detected by the PDK 102 when it enters a proximity zone of the Reader 108. In an alternative embodiment, the communication is instead initiated by the PDK 102 and acknowledged by the Reader 108. The initial communication between the Reader 108 and the PDK 102 is not encrypted to provide increased security of communication between the Reader and the PDK 102.

In step 704, a device authentication is performed. Here, the Reader 108 establishes if the PDK 102 is a valid device and PDK 102 establishes if the Reader 108 is valid. Furthermore, device authentication determines if the PDK 102 is capable of providing the type of authentication required by the Reader 108.

Figure 8:
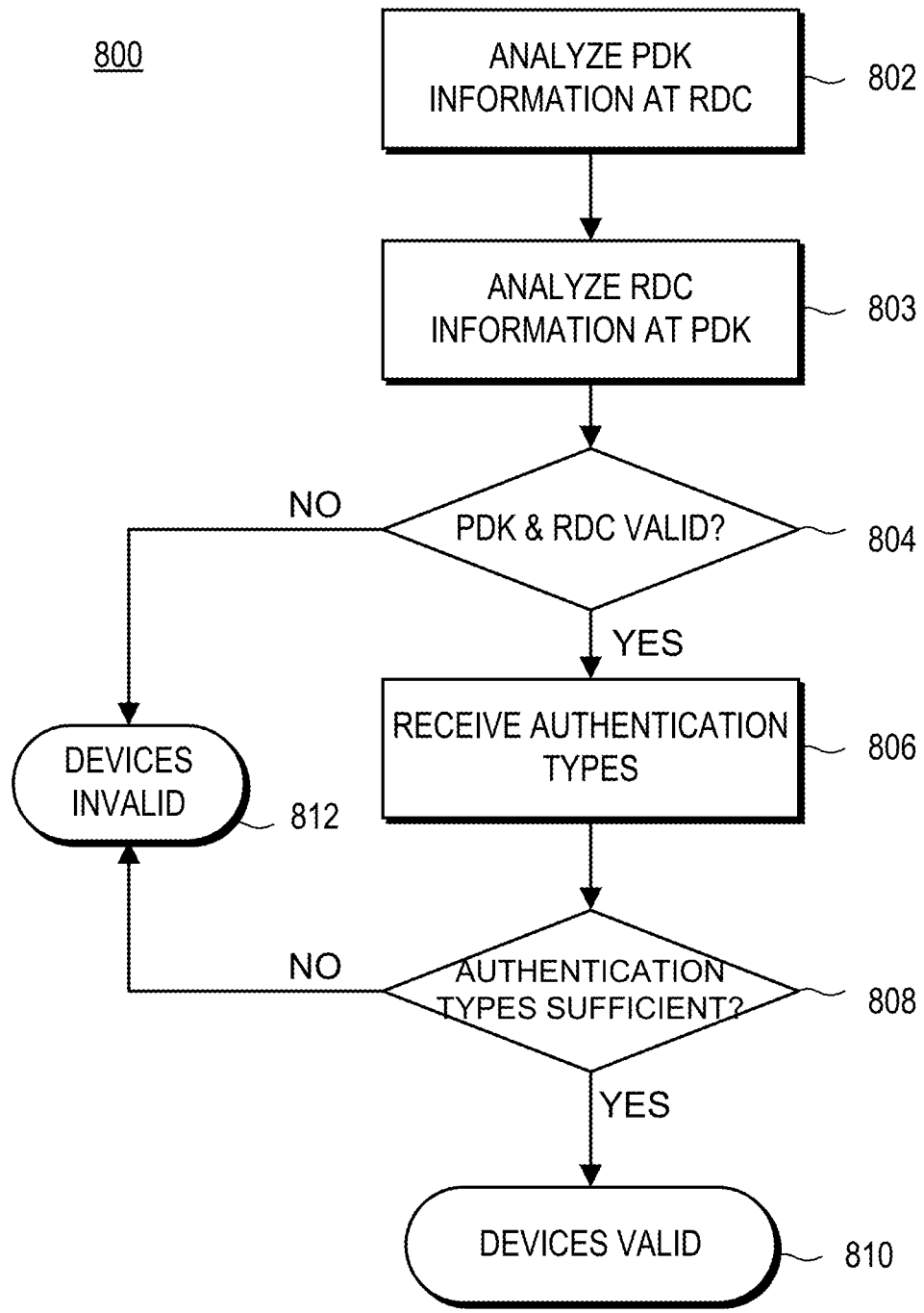
FIG. 8 is a flowchart of a method for device authentication by a reader in accordance with the present invention.

An example embodiment of a method 800 for performing 704 device authentication is illustrated in FIG. 8. The RDC 504 receives and analyzes 802 information from the PDK 102 and the PDK 102 receives and analyzes 802 information received from the RDC 504. Generally, this initial information is transmitted over a public communication channel in an unencrypted format. Based on the received information, each device 102, 504 determines 804 if the other is valid. As will be apparent to one of ordinary skill in the art, a number of different protocols can be used for this type of authentication such as, for example, a challenge-response authentication or a challenge handshake authentication protocol (CHAP). If either of the devices 102, 504 is invalid 812, the process ends. If both the PDK 102 and the RDC 604 are determined by the other to be valid, the Reader 108 requests and receives 806 authentication type information from the PDK 102 indicating the different types of authentication the PDK 102 is capable of satisfying based on the types of profiles stored by the PDK 102.

The available profile types in the PDK 102 are compared against the authentication types that can be used by the Reader 108. For example, a particular Reader 108 may be configured to perform only a fingerprint authentication and therefore any PDK without a fingerprint biometric profile cannot be used with the Reader 108. In one embodiment, the Reader 108 can allow more than one type of profile to be used. In another embodiment, the Reader 108 requires more than one type of profile for authentication, while in yet further embodiments no profile authentications are required. Next, the method determines 808 whether the PDK 102 has one or more profiles sufficient for authentication. If the PDK 102 does not have one or more profiles sufficient for authentication with the Reader 108, the devices 102, 504 are determined to be invalid 812 because they cannot be used with each other. If the PDK 102 does have one or more sufficient types of profiles, the devices are valid 810.

Turning back to FIG. 7, if either the PDK 102 or RDC 504 is not found valid during device authentication 704, the connection is not authorized 718 and the process ends. If the devices are valid, the RDC 504 temporarily buffers 708 the received PDK information. It is noted that in one embodiment, steps 702-708 are automatically initiated each time a PDK 102 enters the proximity zone of the Reader 108. Thus, if multiple PDKs 102 enter the proximity zone, the Reader 108 automatically determines which PDKs 102 are valid and buffers the received information from each valid PDK 102.

The method next determines 710 whether profile authentication is required based on the configuration of the Reader 108, the type of transaction desired or by request of a merchant or other administrator. If the Reader 108 configuration does not require a profile authentication in addition to the PDK authentication, then the Reader 108 proceeds to complete the transaction for the PDK 102. If the Reader 108 does require profile authentication, the profile authentication is performed 712 as will be described below with references to FIGS. 9-10D. If a required profile is determined 714 to be valid, the Reader 108 allows 716 the connection. Otherwise, the Reader 108 indicates that the connection is not authorized 718. In one embodiment, allowing 716 the connection includes enabling access to secure patient records. In another embodiment, allowing 716 the connection includes enabling the automatic logging in and out of software and system applications. Patient or provider name or medical record number (typically stored in a profile memory field 332) can be transmitted by the PDK 102 for identification purposes. In one embodiment, the PDK 102 is configured with multiple purchasing means and a default is configured for different types of transactions. In another embodiment, each insurance card or medical billing information is displayed to the customer by the Reader 108 and the customer is allowed to select which to apply to the office visit.

Figure 9:
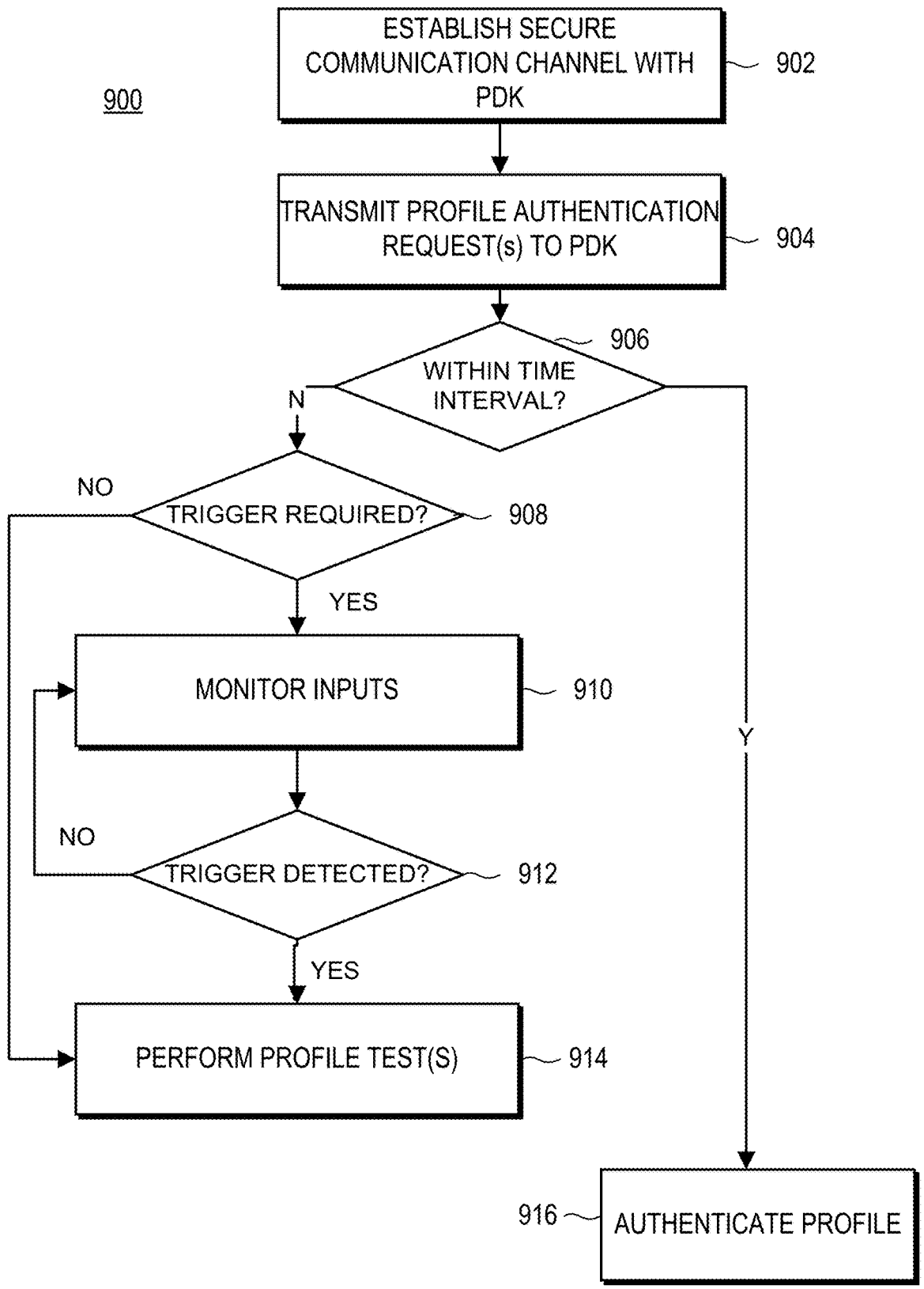
FIG. 9 is a flowchart of a method for profile authentication by a reader in accordance with the present invention.

Turning now to FIG. 9, an embodiment of a method 900 for profile authentication is illustrated. In step 902, a secure communication channel is established between the RDC 504 and the PDK 102. Information sent and received over the secure channel is in an encrypted format that cannot be practically decoded, retransmitted, reused, or replayed to achieve valid responses by an eavesdropping device. The Reader 108 transmits 904 profile authentication requests to the PDK 102 requesting transmission of one or more stored profiles over the secure channel.

In one embodiment, a trigger is required certain times, but not required within specified time intervals. This allows a trigger to initially be required to authenticate a profile, but not required after initial authentication of the profile. For example, a trigger may be required to authenticate a profile the first time the Reader 108 transmits 904 a profile authentication request to the PDK 102, prompting a biometric authentication, or other type of authentication, as further described below. If the profile is authenticated, the next time the Reader 108 transmits 904 a profile authentication request to the PDK 102 during a specified time interval, no trigger is required and the Reader 108 relies on the previous authentication to authenticate the profile. Thus, the time interval simplifies access to a computing device 120 associated with the Reader 108 by identifying a length of time during which the profile is considered to be authenticated without being tested or without requiring detection of a trigger, as described below.

For example, the first time a healthcare provider accesses a computing device 120, the healthcare provider is required to provide a biometric input, as further described below, to verify the identity of the healthcare provider. To simplify subsequent access to the computing device 120, a time interval of four hours is associated with the healthcare provider's profile, so that the healthcare provider's profile remains authenticated by the Reader 108 for four hours after initial authentication. This allows the healthcare provider to subsequently access the computing device 120 without again providing biometric input. However, after four hours have elapsed, when the healthcare provider again accesses the Reader 108, the Reader 108 again requires the healthcare provider to provide a biometric input to verify the healthcare provider's profile.

Accordingly, after the Reader 108 transmits 904 profile authentication requests to the PDK 102 requesting transmission of one or more stored profiles over the secure channel and received a stored profile for authentication, the Reader 108 determines 906 whether a requested profile is within an associated time interval. In one embodiment, the time interval data is transmitted by the PDK 102 along with the profile. Alternatively, the Reader 108 includes data describing time interval data associated with different profiles and uses the included data to determine 906 whether the profile is within its associated time interval. For example, the time interval data includes a profile ID, the time interval and the time when the profile was last authenticated. The Reader 108 determines whether the time when the profile is received responsive to an authentication request is within the duration specified by the time interval of the time when the profile was last authenticated.

If the profile is not within its associated time interval, at 908, the process determines whether a "trigger" is required for authentication. The requirement for a trigger depends on the configuration of the Reader 108, the specific type of transaction to be executed and the type of authentication requested. For example, if it has been longer than the time interval from the time when the profile was previously authenticated to the time when the profile is received responsive to the authentication request, the process determines 908 whether a trigger is needed to authenticate the profile.

In a first configuration, a trigger is required to continue the process because of the type of authentication being used. For example, in biometric authentication, the authentication process cannot continue until the Reader detects a biometric contact and receives biometric information. It is noted that biometric contact is not limited to physical contact and can be, for example, the touch of a finger to a fingerprint scanner, the positioning of a face in front of a facial or retinal scanner, the receipt of a signature, the detection of a voice, the receipt of a DNA sample, RNA sample, or derivatives or any other action that permits the Reader 108 to begin acquiring the biometric input 122. By supplying the biometric contact, the user indicates that the authentication and transaction process should proceed. For example, a PDK holder that wants log in to the healthcare software application system via the computing device 120 initiates the logon process by touching a finger to the reader 720 of the computing device 120. The computing device 120 then displays confirmation of the user's login.

In a second configuration, some other user action is required as a trigger to proceed with the transaction even if the authentication process itself doesn't necessarily require any input. This can be used for many purchasing transactions to ensure that the purchase is not executed until intent to purchase is clear. For example, a Reader 108 at a gas station can be configured to trigger the transaction when a customer begins dispensing gas. At a supermarket, a Reader 108 can be configured to trigger the transaction when items are scanned at a checkout counter. Similarly, a user may log in to healthcare software application system via the computing device 120 by simply being in the proximity zone of the reader 620 of a computing device 120 and beginning to use the keyboard 610 or pointing device 614 of the computing device 120.

In a third configuration, no trigger is used and the Reader 108 automatically completes the remaining authentication/transaction with no explicit action by the user. This configuration is appropriate in situations where the mere presence of a PDK 102 within range of the Reader 108 is by itself a clear indication of the person associated with the PDK 102 desires to complete a transaction. For example, a Reader 108 can be positioned inside the entrance to a doctor's office or clinic. When a patient having an associated PDK 102 walks through the entrance, the Reader 108 detects the PDK 102 within range, authenticates the user, and notifies the receptionist that the patient has arrived for his or her appointment. Thus, if no trigger is required, the process next performs 1014 the requested profile authentication tests.

If a trigger is required, the Reader 108 monitors 910 its inputs (e.g., a biometric reader, key pad, etc.) and checks for the detection 912 of a trigger. If the required trigger is detected, the process continues to perform 914 one or more profile authentication test. FIGS. 10A-10D illustrate various embodiments of profile authentication tests. According to different configurations of the Reader 108, one or more of the illustrated authentication processes may be used. Further, in some embodiments, one or more of the processes may be repeated (e.g., for different types of biometric inputs).

However, if the Reader 108 determines 906 that the requested profile is received within an associated time interval, the Reader authenticates 916 the profile. This beneficially simplifies access to a computing device 120 coupled to the Reader 108 by allowing an individual to bypass profile authentication when the Reader 108 is accessed within a time interval of the initial profile authentication.

Figure 10B:
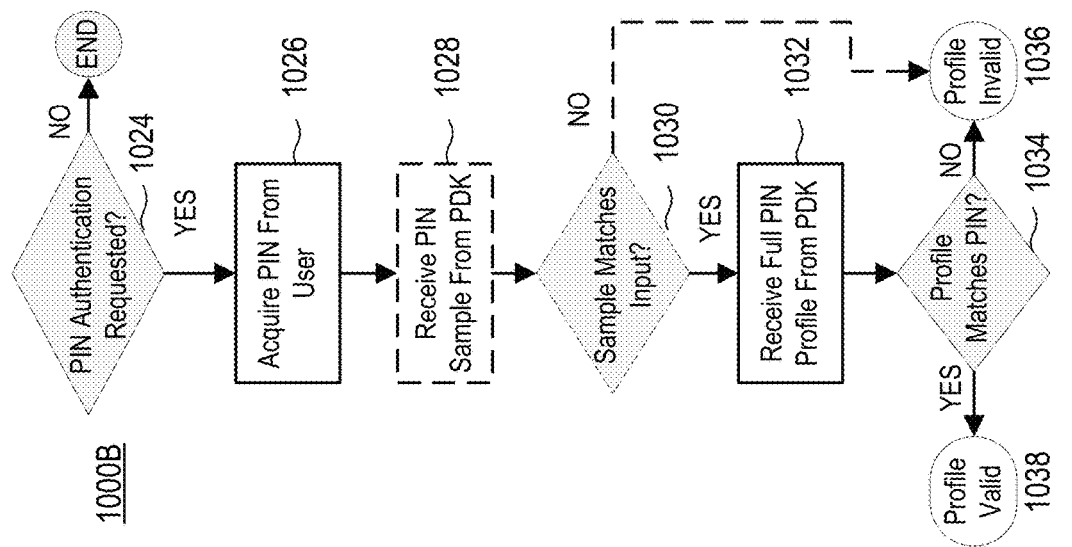
FIG. 10B is a flowchart of a method for profile testing using a personal identification number in accordance with the present invention.
Figure 10A:
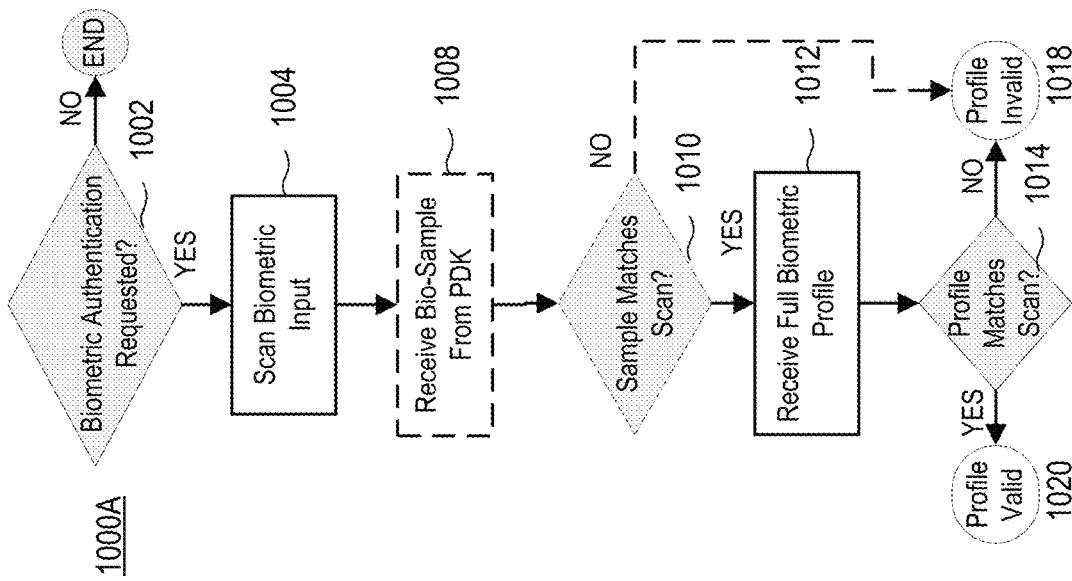
FIG. 10A is a flowchart of a method for biometric authentication in accordance with the present invention.

FIG. 10A illustrates a method 1000A for biometric authentication. In biometric authentication, a Reader 108 compares a biometric profile stored in the PDK 102 to the biometric input 122 acquired by the biometric reader 502. Advantageously, the biometric input 122 is not persistently stored by the Reader 108, reducing the risk of theft or fraudulent use. If the Reader 108 determine 1002 that biometric authentication is requested, the Reader 108 scans 1104 the biometric input 122 supplied by the user. In one embodiment, scanning 1004 includes computing a mathematical representation or hash of the biometric input 122 that can be directly compared to the biometric profile.

In one embodiment, scanning 1004 also includes obtaining a biometric input sample from the biometric input according to the same function used to compute the biometric profile sample stored in the PDK 102. Optionally, the Reader 108 receives 1008 a biometric profile sample from the PDK 102 and determines 1100 if the biometric profile sample matches the biometric input sample. If the biometric profile sample does not match the input sample computed from the scan, the profile is determined to be invalid 1018.

If the biometric profile sample matches, the full biometric profile 1012 is received from the PDK 102 to determine 1014 if the full biometric profile 1012 matches the complete biometric input 122. If the profile 1112 matches the scan, the profile 1112 is determined to be valid 1120, otherwise the profile 1012 is invalid 1018. It is noted that in one embodiment, steps 1008 and 1010 are skipped and only a full comparison is performed. In one embodiment, the biometric profile and/or biometric profile sample is encoded and transmitted to the Reader 108 along with an encoding key and/or algorithm. Then, the Reader 108 uses the encoding key and/or algorithm to recover the biometric profile and/or biometric profile sample. In another alternative embodiment, only the encoding key and/or algorithm is transmitted by the PDK 102 and the biometric profile data is recovered from a remote database in an encoded form that can then be decoded using the key and/or algorithm.

It will be apparent to one of ordinary skill that in alternative embodiments, some of the steps in the biometric profile authentication process can be performed by the PDK 102 instead of the Reader 108 or by an external system coupled to the Reader 108. For example, in one embodiment, the biometric input 122 can be scanned 1004 using a biometric reader built into the PDK 102. Furthermore, in one embodiment, the steps of computing the mathematical representation or hash of the biometric input and/or the steps of comparing the biometric input to the biometric profile can be performed by the PDK 102, by the Reader 108, by an external system coupled to the Reader 108, or by any combination of the devices. In one embodiment, at least some of the information is transmitted back and forth between the PDK 102 and the Reader 108 throughout the authentication process. For example, the biometric input 122 can be acquired by the PDK 102, and transmitted to the Reader 108, altered by the Reader 108, and sent back to the PDK 102 for comparison. Other variations of information exchange and processing are possible without departing from the scope of the invention. The transfer of data between the PDK 102 and the Reader 108 and/or sharing of processing can provide can further contribute to ensuring the legitimacy of each device.

FIG. 10B illustrates a method 1000B for PIN authentication. If PIN authentication is requested 1024, a PIN is acquired 1026 from the user through a keypad, mouse, touch screen or other input mechanism. Optionally, the Reader 108 receives 1028 a PIN sample from the PDK 102 comprising a subset of data from the full PIN. For example, the PIN sample can comprise the first and last digits of the PIN. If the Reader 108 determines 1030 that the PIN sample does not match the input, the profile is immediately determined to be invalid 1036. If the PIN sample matches, the full PIN profile is received 1032 from the PDK 102 and compared to the input. If the Reader 108 determines 1034 that the profile matches the input, the profile is determined to be valid and is otherwise invalid 1036. It is noted that in one embodiment, steps 1028 and 1030 are skipped.

Figures 10C, 10D:
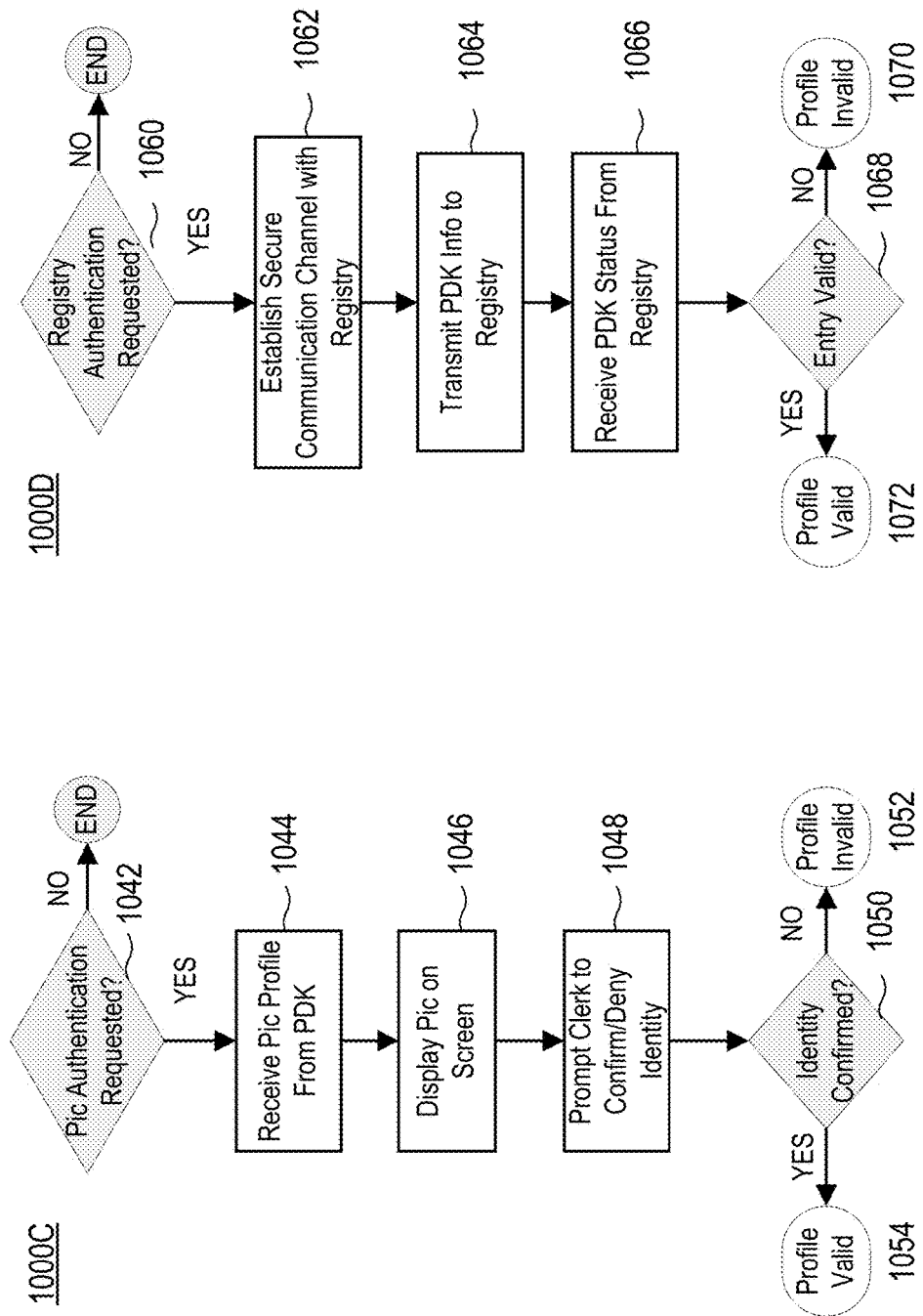
FIG. 10C is a flowchart of a method for profile testing using a picture profile in accordance with the present invention.
FIG. 10D is a flowchart of a method for profile testing using a private or central registry in accordance with the present invention.

FIG. 10C illustrates a method 1000C for a picture authentication. If the Reader 108 determines 1024 that picture authentication is requested, a picture profile is received 1044 from the PDK 102 by the Reader 108 and displayed 1046 on a screen. An administrator (e.g., a clerk, security guard, etc.) is prompted 1048 to compare the displayed picture to the individual and confirms or denies if the identities match. If the administrator confirms that the identities match, the picture profile is determined to be valid 1064 and is otherwise invalid 1052. In an alternative embodiment, the process is automated and the administrator input is replaced with a process similar to that described above with reference to FIG. 10A. Here, an image of the user is captured and face recognition is performed by comparing picture profile information received from the PDK 102 to the captured image.

FIG. 10D illustrates a method 1000D for authentication with a private registry 116a, 116b or the Central Registry 114. If the Reader 108 determines that registry authentication is requested, a secure communication channel is established 1062 over the network 110 between the Reader 108 and one or more registries (e.g., the Central Registry 114, any private registry 116a, 116b, or other validation database 112). If any additional information is needed to process the registry authentication (e.g., an insurance policy number), the Reader 108 requests and receives the additional information from the PDK 102. Identification information is transmitted 1064 from the Reader 108 to the registry 114, 116a, 116b through the network interface 608. The PDK status is received 1066 from the registry to determine 1068 if the status is valid 1072 or invalid 1070. In one embodiment, the information is processed remotely at the registry 114, 116a, 116b and the registry 114, 116a, 116b returns a validation decision to the Reader 108. In another embodiment, the Reader 108 queries the private 116a, 116b or Central registry 114 for information that is returned to the Reader 108. The information is then analyzed by the Reader 108 and the authorization decision is made locally. In one embodiment, the process involves transmitting credit card (or other purchasing information) to a validation database 112 to authorize the purchase and receive the status of the card. Status information may include, for example, confirmation that the card is active and not reported lost or stolen and that sufficient funds are present to execute the purchase.

Figure 11A:
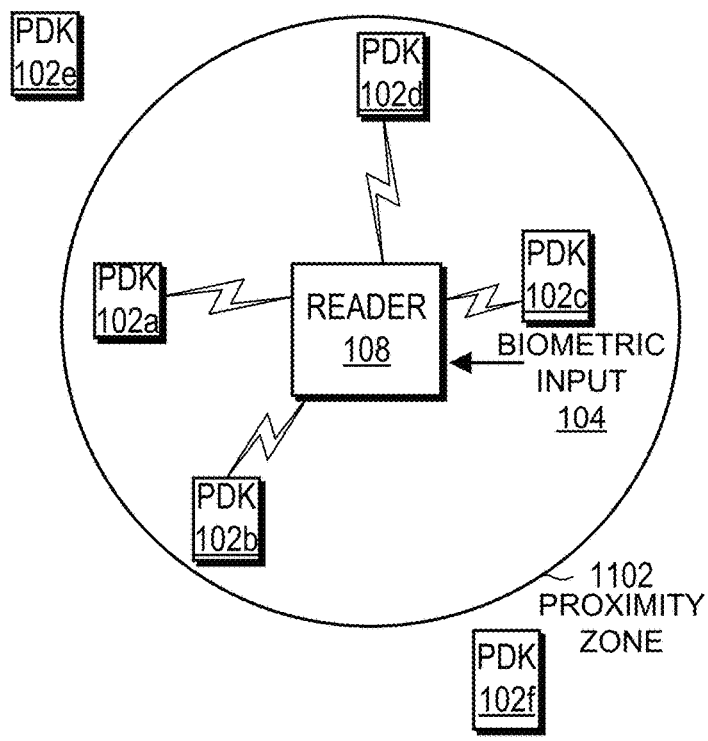
FIG. 11A illustrates an example scenario of a reader operating with multiple PDKs in its proximity zone in accordance with the present invention.
Figure 11B:
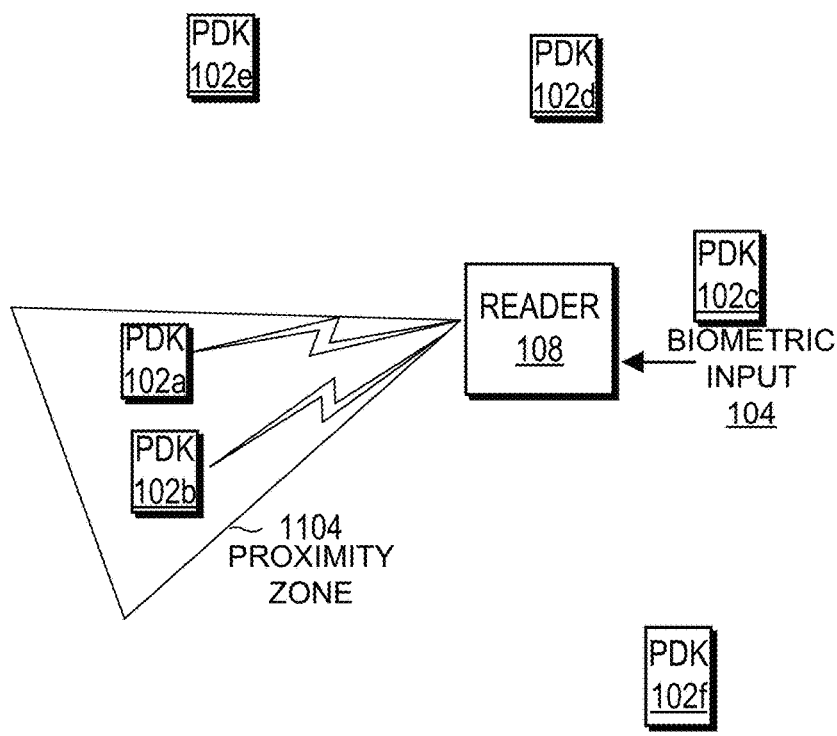
FIG. 11B illustrates an example scenario of operation of a reader with a directional proximity zone in an environment with multiple PDKs in accordance with the present invention.

FIGS. 11A and 11B illustrate scenarios where multiple PDKs 102*a-e* are present near a Reader 108. This scenario is common when a Reader 108 is located in a high occupancy area such as, for example, a hospital lobby or waiting area. In FIG. 11A, the Reader 108 communicates with PDKs 102*a-d* within the proximity zone 1102 and does not communicate with PDKs 102*e-f* outside the proximity zone 1102. In one embodiment, the Reader 108 receives the unique PDK ID from a PDK 102 when it enters the proximity zone 1102 and records its time of arrival. In one embodiment, the Reader 108 further initiates a device authentication of the PDK 102 after a predefined period of time (e.g., 5 seconds) that the PDK 102 is within the proximity zone 1102. For profile authentication, the Reader 108 automatically determines which PDK 102 should be associated with an authentication test and the transaction. For example, if the Reader 108 receives a biometric input 122 from an individual, the Reader 108 automatically determines which PDK 102*a-d* is associated with the individual supplying the biometric input 122. In another embodiment, a different trigger is detected (e.g., a PIN input) to initiate the differentiation decision. In yet another embodiment, the differentiation decision is initiated without any trigger. It is noted that in some embodiments, where no trigger is required (such as a registry authentication), no differentiation decision is made and authentications are instead performed for each PDK 102 within the proximity zone 1102.

In one embodiment, the proximity zone 1102 is scalable, allowing modification of the area in which the Reader 108 communicates with a PDK 102. For example, the proximity zone 1102 of a Reader 108 may be modified from 1 foot to 100 feet. In one embodiment, an administrator or other designated individual modifies the proximity zone 1102 of a Reader 108. This allows the sensitivity of a Reader 108 to be modified based on different operating environment. For example, in a healthcare provider setting, the proximity zone 1102 of a Reader 108 located in a doctor's office is smaller than the proximity zone 1102 of a Reader 108 located in an examination room to reduce the number of times that the Reader 108 in the doctor's office attempts to authenticate a PDK 102.

Additionally, while FIG. 11A shows a proximity zone 1102 that is symmetrical, in other implementations, the proximity zone is directional. FIG. 11B shows a directional proximity zone 1104 where the Reader 108 interacts with PDKs 102a, 102b in a specific location. Hence, in FIG. 11B the Reader 108 communicates with PDKs 102a,b within the directional proximity zone 1104 and does not communicate with PDKs 102c-f outside the directional proximity zone 1104. In one embodiment, a Reader 108 has an initial configuration of a proximity zone 1102 that extends 360 degrees around the Reader; however, the Reader 108 may be modified from the initial configuration to focus the proximity zone into a directional proximity zone 1104. For example, a directional antenna may be coupled to the Reader 108 to generate a directional proximity zone 1104.

Figure 12:
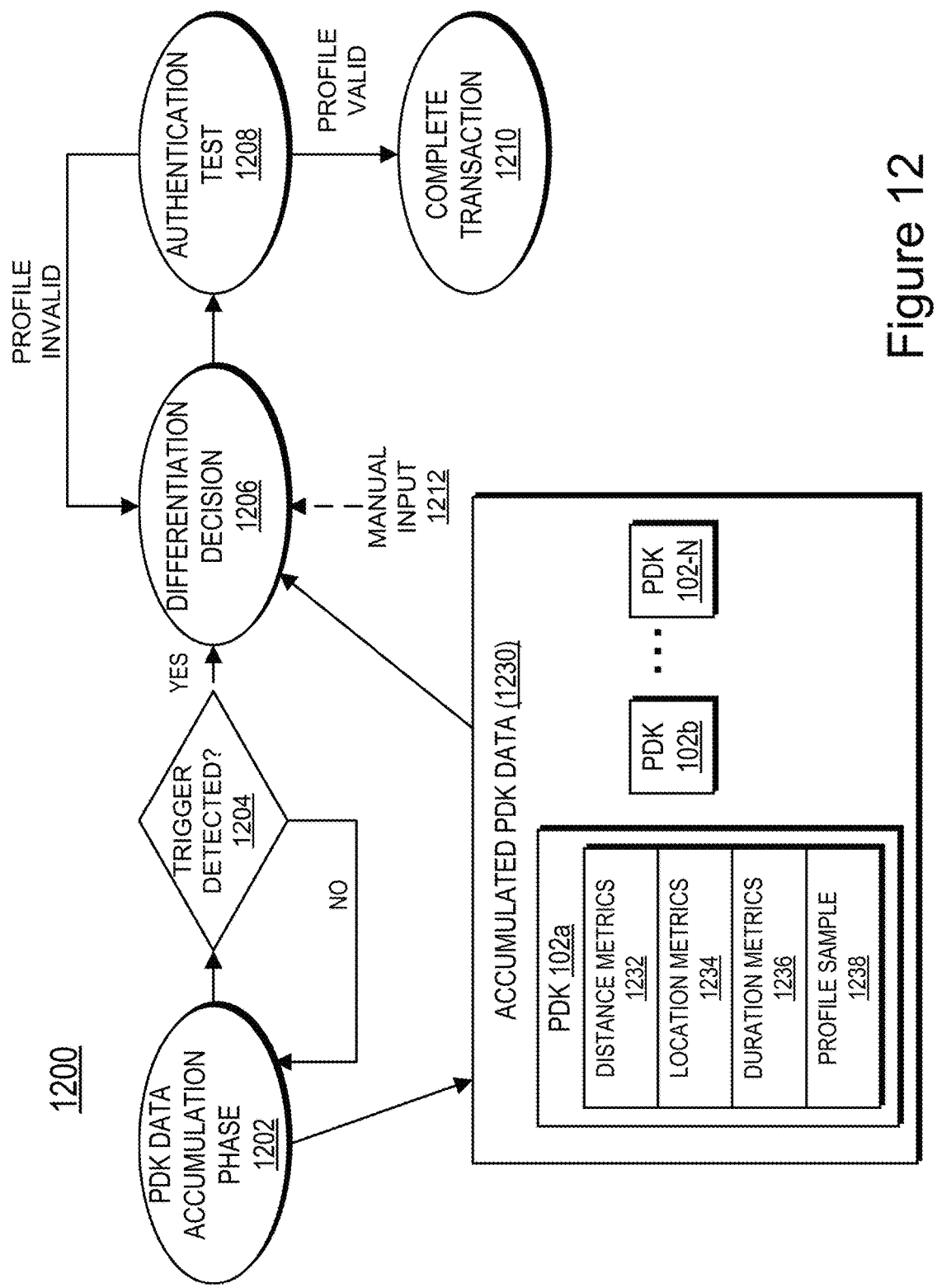
FIG. 12 is a flowchart of a method for differentiating between multiple PDKs within the proximity zone of a reader in accordance with the present invention.

FIG. 12 illustrates an embodiment of an authentication method 1200 for the scenario where multiple PDKs 102 are present within a proximity zone 1102 or directional proximity zone 1104 of a Reader 108. In a PDK data accumulation phase 1202, PDK data 1230 is accumulated and buffered in the Reader 108 for any valid PDKs 102 that enter the proximity zone 1102 or the directional proximity zone 1104. In one embodiment, the accumulation phase 1202 begins for a PDK 102 after it has been within the proximity zone 1102, or directional proximity zone 1104, for a predetermined period of time. In one embodiment, the PDK data accumulation phase 1202 is similar to the steps 702-708 described above in detail with reference to FIG. 7 for each PDK 102a-d in the proximity zone 1102 or the directional proximity zone 1104.

As illustrated, the accumulated PDK data 1230 includes one or more differentiation metrics from each valid PDK 102 within range of the Reader 108. The differentiation metrics can include any information that can be used by the Reader 108 to determine which PDK 102 should be associated with the authentication and/or transaction request. According to various embodiments, differentiation metrics can include one or more of distance metrics 1232, location metrics 1234 and duration metrics 1236.

In one embodiment, a distance metric 1232 indicates the relative distance of a PDK 102 to the Reader 108. This information is useful given that a PDK 102 having the shortest distance to the Reader 108 is generally more likely to be associated with a received authentication trigger (e.g., a biometric input, a PIN input or a transaction request). The distance metrics 1232 can include, for example, bit error rates, packet error rates and/or signal strength of the PDKs 102. These communication measurements can be obtained using a number of conventional techniques that will be apparent to those of ordinary skill in the art. Generally, lower error rates and high signal strength indicate the PDK 102 is closer to the Reader 108.

Location metrics 1234 can be used to determine a location of a PDK 102 and to track movement of a PDK 102 throughout an area. This information can be useful in determining the intent of the PDK holder to execute a transaction. For example, a PDK holder that moves in a direct path towards a cashier and then stops in the vicinity of the cashier is likely ready to make a purchase (or may be waiting in line to make a purchase). On the other hand, if the PDK 102 moves back and forth from the vicinity of a cashier, that PDK holder is likely to be browsing and not ready to make a purchase. Examples of systems for determining location metrics are described in more detail below with reference to FIGS. 13-14.

The differentiation metrics can also include duration metrics 1236 that tracks the relative duration a PDK 102 remains within the proximity zone 1102 or within the directional proximity zone 1104. Generally, the PDK 102 with the longest time duration within the proximity zone 1102, or the proximity zone 1104, is most likely to be associated with the authentication request. For example, if the Reader 108 is busy processing a purchasing transaction at a cashier and another PDK 102 has a long duration within the proximity zone 1102 or the directional proximity zone 1104, it is likely that the user is waiting in line to make a purchase. In one embodiment, the Reader 108 tracks duration 1236 by starting a timer associated with a PDK 102 when the PDK 102 enters the proximity zone 1102, or the directional proximity zone 1104, and resetting the time to zero when the PDK 102 exists. As another example, the Reader 108 tracks the duration when a PDK 102 of a doctor enters the proximity zone of a patient's room. A long duration of the doctor's PDK 102 within the proximity zone can provide evidence that the doctor is spending an adequate amount of time examining the patient. On the other hand, a short duration of the doctor's PDK 102 within the proximity zone can provide evidence that the doctor just merely stopped by and did not perform any thorough examination. This information is useful in monitoring patient treatment and provider performance to help ensure quality patient care.

In one embodiment, the Reader 108 can also receive and buffer profile samples 1238 prior to the start of a profile authentication instead of during the authentication process as described in FIGS. 10A-10B. In one embodiment, the Reader 108 determines which types of biometric profile samples 1238 to request based on, for example, the configuration of the Reader 108, the type of transactions performed by the Reader 108, or manual requests from a clerk, security guard, etc. In one embodiment, the PDK 102 transmits one or more of the requested sample types based on profiles available in the PDK 102 and/or user preferences. In another embodiment, the PDK 102 transmits one or more samples 1238 it has available and only samples that match the authentication types configured for the Reader 108 are buffered. For example, if a Reader 108 is configured for fingerprint authentication, a PDK 102 may transmit samples 1238 for several different fingerprint profiles (each corresponding to a different finger, for example). It will be apparent to one of ordinary skill in the art that other variations are possible to provide flexibility in both the configuration of the Reader 108 for various types of authentication and flexibility for the PDK owner to determine which types of authentication to use.

Because profile samples 1238 only comprise a subset of the profile information, in one embodiment, the samples can be safely transmitted over a public channel without needing any encryption. In another embodiment, the profile samples 1238 are transmitted with at least some level of encryption. In yet another embodiment, some of the data is transmitted over a public communication channel and additional data is transmitted over a secure communication channel. In different configurations, other types of profile information can be accumulated in advance. For example, in one embodiment, a photograph from a picture profile can be obtained by the Reader 102 during the data accumulation phase 1202. By accumulating the profile sample 1238 or other additional information in advance, the Reader 108 can complete the authentication process more quickly because it does not wait to receive the information during authentication. This efficiency becomes increasingly important as the number of PDKs 102 within the proximity zone 1102, or within the directional proximity zone 1104, at the time of the transaction becomes larger.

The PDK accumulation phase 1202 continues until a trigger (e.g., detection of a biometric input) is detected 1204 to initiate a profile authentication process. If a biometric input is received, for example, the Reader 108 computes a mathematical representation or hash of the input that can be compared to a biometric profile and computes one or more input samples from the biometric input. It is noted that in alternative embodiments, the process can continue without any trigger. For example, in one embodiment, the transaction can be initiated when a PDK 102 reaches a predefined distance from the Reader 108 or when the PDK 102 remains within the proximity zone 1102, or within the directional proximity zone 1104, for a predetermined length of time.

The process then computes a differentiation decision 1206 to determine which PDK 102a-d should be associated with the authentication. In one embodiment, the Reader 108 computes a differentiation result for each PDK 102 using one or more of the accumulated data fields 1230. For example, in one embodiment, the differentiation result is computed as a linear combination of weighted values representing one or more of the differentiation metrics. In another embodiment, a more complex function is used. The differentiation results of each PDK 102 are compared and a PDK 102 is selected that is most likely to be associated with the transaction.

In another embodiment, for example, in a photo authentication, the differentiation decision can be made manually by a clerk, security guard, or other administrator that provides a manual input 1212. In such an embodiment, a photograph from one or more PDKs 102 within the proximity zone 1102 or within the directional proximity zone 1104 can be presented to the clerk, security guard, or other administrator on a display and he/she can select which individual to associate with the transaction. In yet another configuration, the decision is made automatically by the Reader 108 but the clerk is given the option to override the decision.

An authentication test 1208 is initiated for the selected PDK 102. The authentication test 908 can include one or more of the methods illustrated in FIGS. 10A-10D. Note that if profile samples 1238 are acquired in advance, they need not be acquired again in the authentication steps of FIGS. 10A-10B. It is additionally noted that in one embodiment, the Reader 108 compares the profile samples 1238 of the PDKs 102 to the computed input sample until a match is found before performing a full profile comparison. In one embodiment, the Reader 108 first compares samples from the selected PDK 102 until a match is found. For example, a Reader 108 may have accumulated multiple fingerprint profiles samples 1238 (e.g., corresponding to different fingers) for the selected PDK 102. The Reader 108 receives a fingerprint input from, for example, the left index finger, computes the input sample, and does a quick comparison against the accumulated samples 1338 for the selected PDK 102 to efficiently determine a matching profile. The Reader 108 then performs the full comparison using the matching profile. In an alternative embodiment, the Reader 108 performs a comparison of a first sample from each PDK 102 and if no match is found, performs comparisons of second samples from each PDK 102. It will be apparent to one of ordinary skill in the art that samples can be compared in a variety of other orders without departing from the scope of the invention.

If the authentication test 1208 indicates a valid profile, the transaction is completed 1210 for the matching PDK 102. If the authentication test 1208 determines the profile is invalid, a new differentiation decision 1206 is made to determine the next mostly likely PDK 102 to be associated with the transaction. The process repeats until a valid profile is found or all the PDKs 102 are determined to be invalid.

Figure 13:
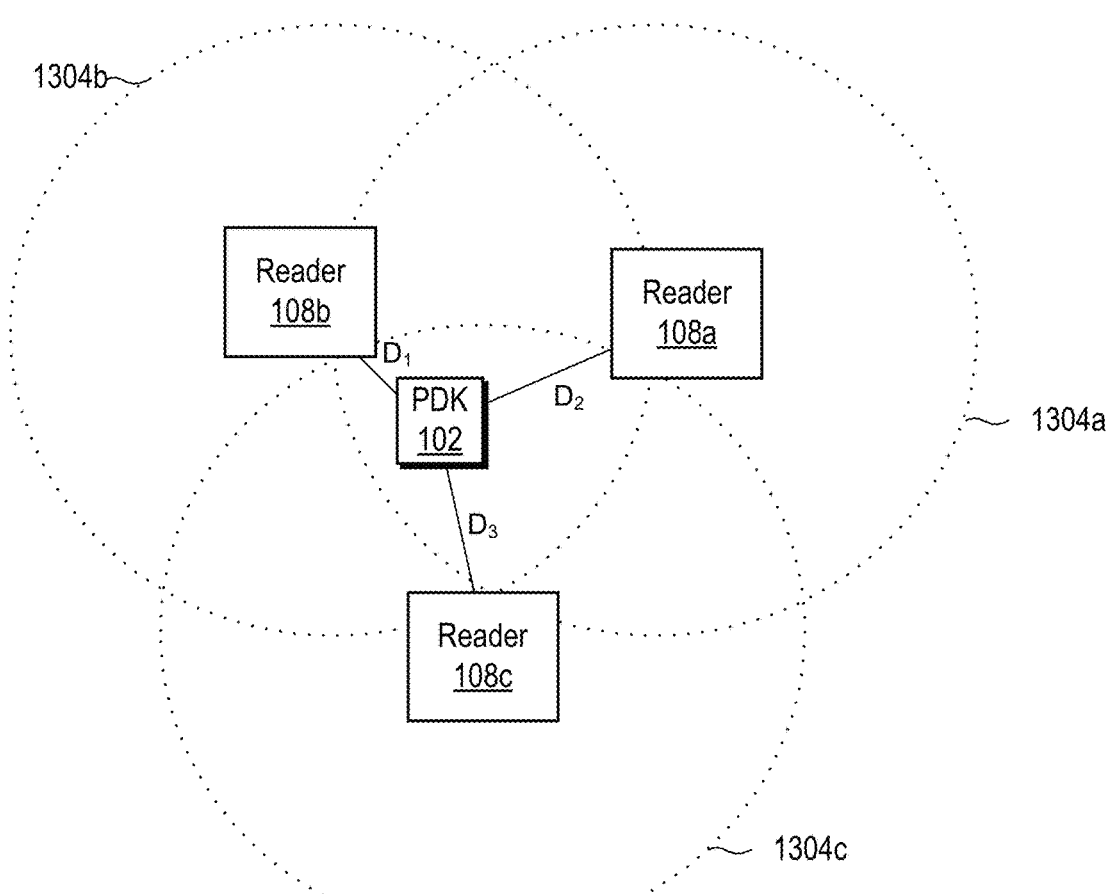
FIG. 13 is a block diagram of a system for estimating location of a PDK using coordinate triangulation in accordance with the present invention.

FIG. 13 illustrates an example system is illustrated for determining a location metric 1234 of a PDK 102 using a coordinate triangulation technique. In one embodiment of coordinate triangulation, multiple transmitting devices (e.g., Readers 108a-c) are spaced throughout an area. In one embodiment, the Readers 108a-c are coupled by a network. Each Reader 108a-c has a range 1304 and the ranges 1304 overlap. Each Reader 108a-c determines a distance D1-D3 between the Reader 108 and the PDK 102. Distance may be estimated, for example, by monitoring signal strength and/or bit error rate as previously described. Then using conventional trigonometry, an approximate location of the PDK 102 can be calculated from D1-D3. Although only three transmitters are illustrated, it will be apparent that any number of transmitters can be used to sufficiently cover a desired area. Location information can be computed at predetermined time intervals to track the movement of PDKs 102 throughout a facility.

Figure 14:
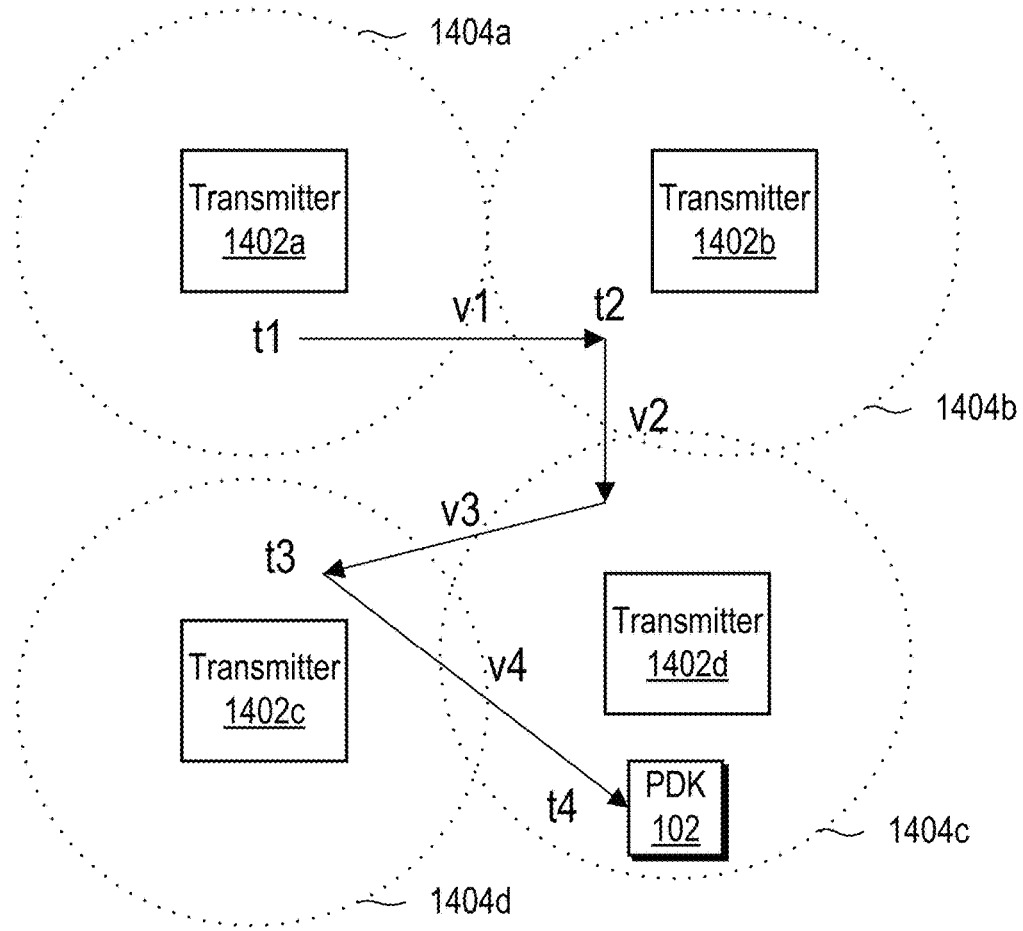
FIG. 14 is a block diagram of an alternative system for location tracking of a PDK in accordance with the present invention.

Another embodiment of location tracking is illustrated in FIG. 14. Here, transmitters 1402 having ranges 1404 are distributed throughout an area. The ranges 1404 can vary and can be overlapping or non-overlapping. In this embodiment, each transmitter 1402 can detect when a PDK 102 enters or exists its range boundaries 1404. By time-stamping the boundary crossings, a location vector can be determined to track the PDK's movement. For example, at a first time, t1, the PDK 102 is detected within the range of transmitter 1402a. At a second time, t2, the PDK 102 is detected within the range of transmitter 1402b. At a third time, t3, the PDK 102 is within the range of transmitter 1402c and at a fourth time, t4, the PDK 102 is within the range of transmitter 1402d. Using the location and time information, approximate motion vectors, v1, v2, v3, and v4 can be computed to track the motion of the PDK 102 without necessarily computing exact distance measurements.

Figure 15:
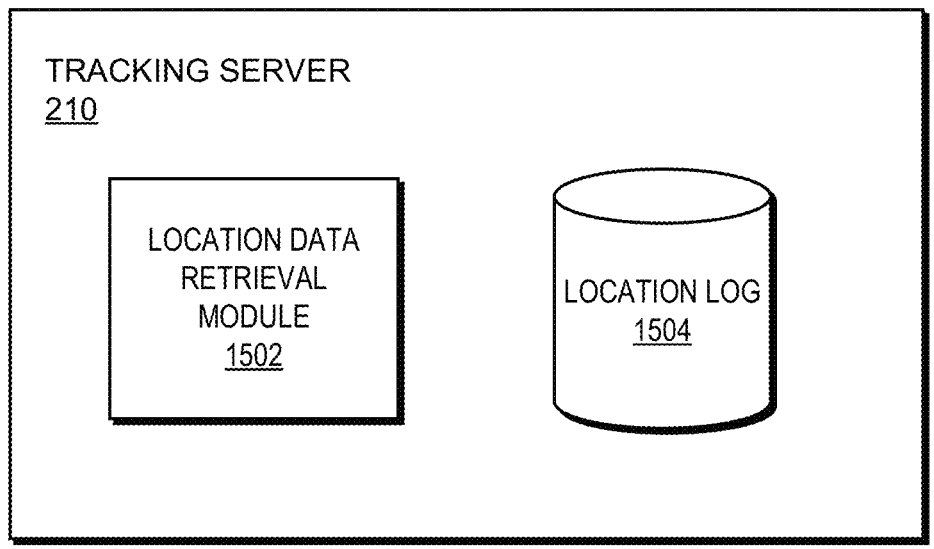
FIG. 15 is a block diagram of a tracking server in accordance with the present invention.

FIG. 15 is a block diagram illustrating an embodiment of a tracking server 210. The tracking server 210 enables real-time tracking of individuals, equipment and supplies by monitoring and storing location information of individuals, equipment or supplies with associated PDKs 102. For example, the tracking server 210 allows rapid location of healthcare providers in case of an emergency, allows monitoring of patient location to ensure timely administration of medications and allows constant monitoring of equipment or supply location to minimize search time and inventory surplus requirements. One embodiment of the tracking server 210 includes a location data retrieval module 1502 and a location log 1504. In one embodiment, the location log 1504 is a database, such as a Structured Query Language (SQL) database.

In one embodiment, multiple Readers 108 are placed at certain and known positions throughout a facility. For example, a Reader is placed above each doorway of every room and at every computing device 120. In another embodiment, Readers 108 are placed in a grid pattern throughout the facility. In one embodiment, entities within the facility carry an associated PDK 102 uniquely identifying the entity and PDKs 102 are attached to different pieces of equipment or supplies within the facility. Example embodiments of a tracking system are described in U.S. patent application Ser. No. 11/939,451 to John Giobbi, et al., entitled "Tracking System Using Personal Digital Key Groups" and filed on Nov. 13, 2007, the entire contents of which are incorporated herein by reference.

Figure 16A:
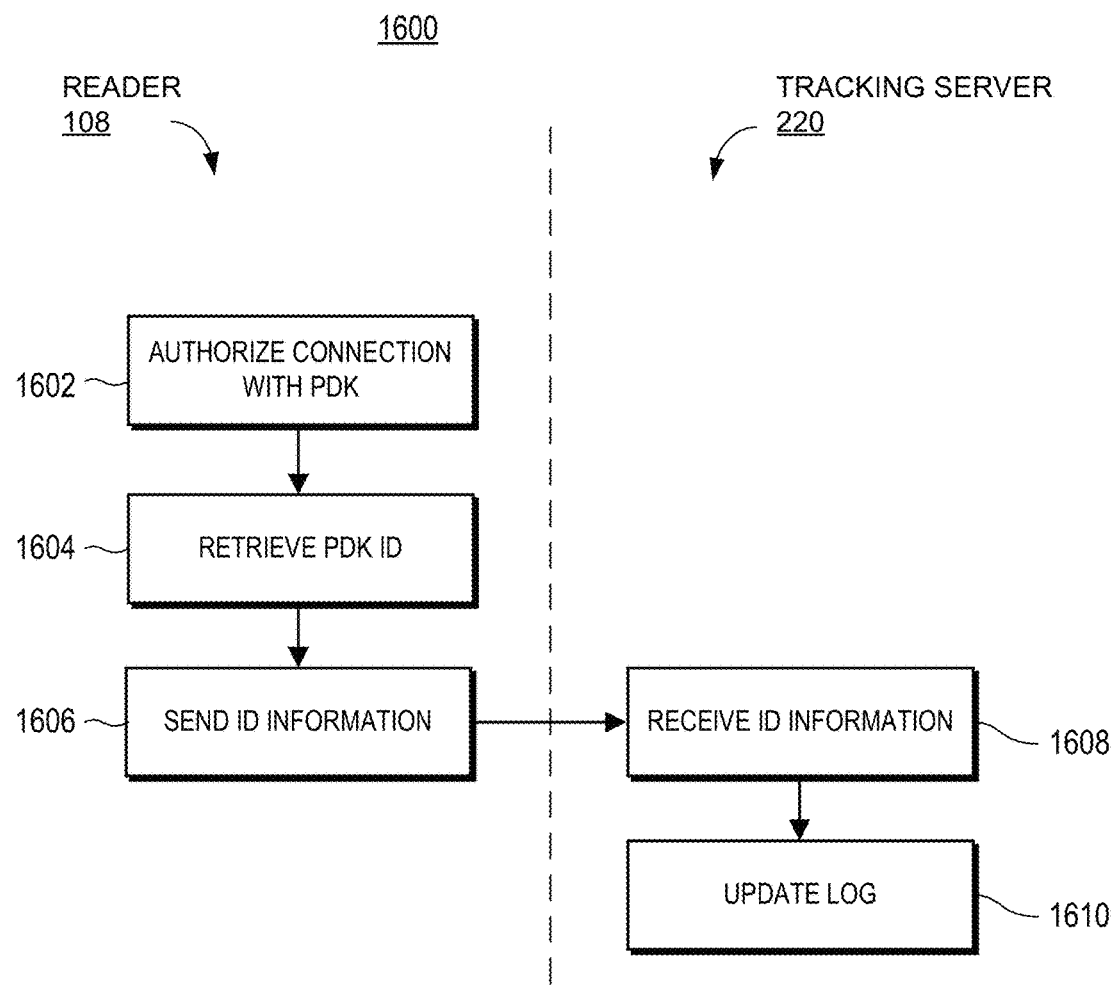
FIG. 16A is a flowchart of a method for tracking assets or users in accordance with the present invention.

A flowchart illustrating one embodiment of a process 1600 for tracking of equipment and individuals is shown in FIG. 16A. When a PDK 102 comes within the range of a Reader 108, connection is authorized 1602 between the RDC 504 of the Reader 108 and the PDK 102. In one embodiment, the RDC 504 continually transmits beacons that are detected by the PDK 102 when it enters a proximity zone of the Reader 108. In an alternative embodiment, the communication is instead initiated by the PDK 102 and acknowledged by the Reader 108. As shown in the previous FIG. 7, device authentication is first performed and once the Reader 108 establishes if the PDK 102 is a valid device and PDK 102 establishes if the Reader 108 is valid, connection can be authorized.

Once connection is authorized 1602, the Reader 108 retrieves 1604 the PDK 102 information, such as PDK ID 312 and other information identifying the owner or entity associated with the PDK 102. In one embodiment, the reader ID 518 of the Reader 108 is sent to the PDK 102 and stored in the activity log 390 of the PDK 102. The reader and PDK information is sent 1606 to the tracking server 210. The location data retrieval module 1502 receives 1608 the information, including the PDK ID 312. The information is updated 1610 in the location log 1604 of the tracking server 210.

In one embodiment, the location log data is retrieved by the computing device 120. In such embodiments, the computing device 120 displays the locations of the individuals and equipment being tracked; therefore making it possible to locate anyone and any piece of equipment at any given moment. In some embodiments, the location log data is displayed graphically, for example, with a map of the facility and indications on the map identifying locations of tracked items and people. In other embodiments, the location log data is displayed on the computing device 120 with text describing the locations of the tracked items and people.

Figure 16B:
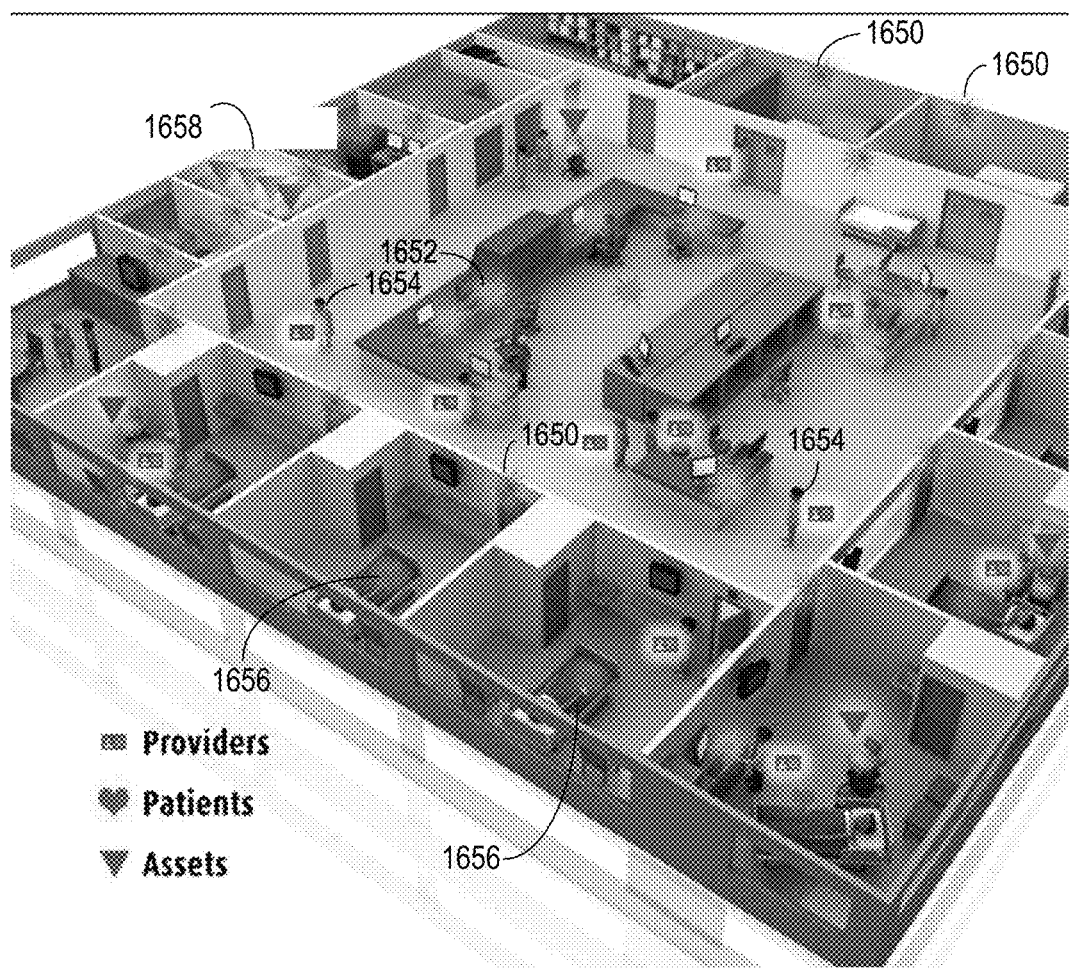
FIG. 16B is a graphical representation illustrating an example embodiment where patient, provider and equipment tracking is provided within a healthcare facility in accordance with the present invention.

This process 1600 occurs whenever a PDK 102 enters the proximity zone of each Reader 108 that it passes enabling constant tracking and location of individuals carrying PDKs 102 and equipment with affixed PDKs 102. FIG. 16B is a graphical representation illustrating an example where patient, provider and equipment tracking is provided within a healthcare facility. Readers 1650 are located at various locations throughout the healthcare facility to receive PDK information. Computing devices are also equipped with readers 1652 for receiving PDK information. The Readers 1650 and 1652 receive information from the provider PDKs 1654, patient PDKs 1656 and equipment PDKs 1658 enabling the location and tracking of providers, patients and equipment anywhere throughout the healthcare facility.

Figure 17:
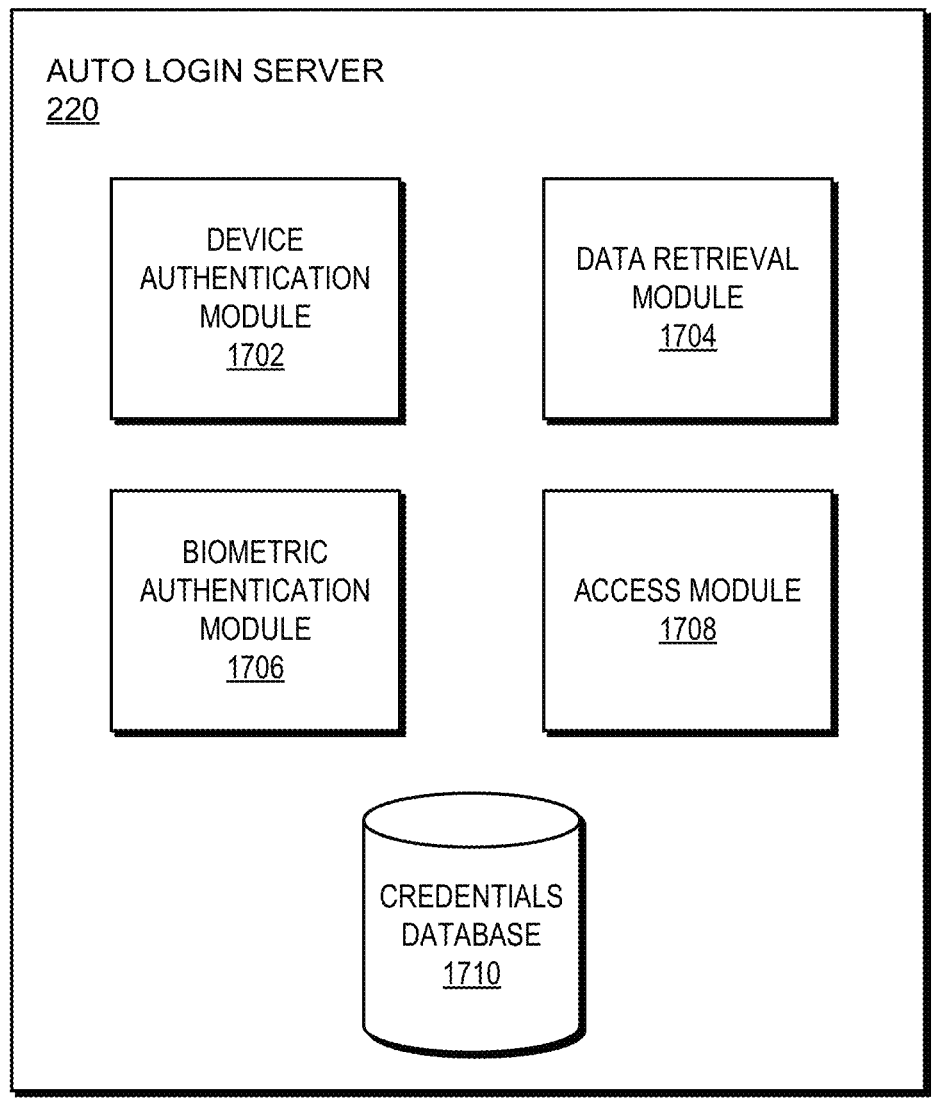
FIG. 17 is a block diagram of an auto login server in accordance with the present invention.

FIG. 17 is a block diagram illustrating an embodiment of an auto login server 220. The auto login server 220 allows for automated electronic signing on of providers into the healthcare computer system, therefore eliminating the constant and time-consuming login and logout of healthcare providers such as doctors, nurses, physician assistants, medical technicians, and other caregivers. In one embodiment, providers can utilize their PDKs 102 to automatically log in to the application software system by simply approaching or entering the proximity zone of a Reader 620 of a computing device 120. In such embodiments, no manual input is necessary. The auto login server 220 includes a device authentication module 1702, a data retrieval module 1704, a biometric authentication module 1706, an access module 1708 and a credentials database 1710. In some embodiments the auto login server resides in the local services module 124. The auto login server includes input and output ports for receiving data from and sending data to one or more Readers 108. The device authentication module 1702 is coupled to the biometric authentication module 1706 and data retrieval module 1704. The data retrieval module is couple to communicate with the access module, which is further configured to send access authorization to readers 620, 108 and computing device 120.

Figure 18:
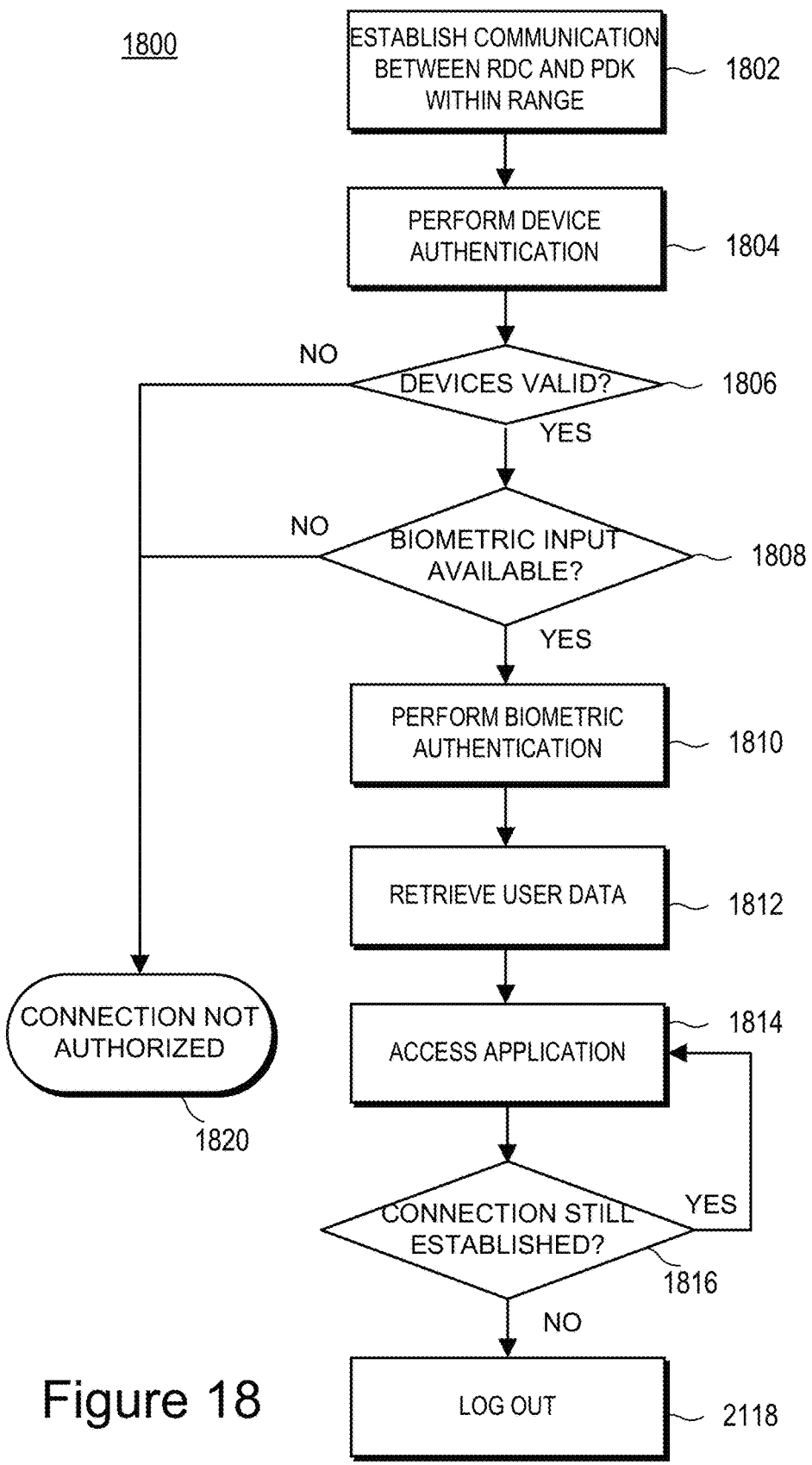
FIG. 18 is a flowchart of a method for automatic login of a user in accordance with the present invention.

FIG. 18 is a flowchart illustrating one embodiment of a method 1800 for automatic login of a user. When a user carrying or wearing a PDK 102 comes within the range of a Reader 620 communicating with a computing device 120, communication is automatically established 1802 between the RDC 504 of the Reader 620 of a computing device 120. In one embodiment, the PDK 102 is incorporated into an identification badge of the user. Once communication with the PDK 102 is established, device authentication is performed 1804.

In one embodiment, the device authentication module 1702 performs 1804 device authentication. In another embodiment, the device authentication is performed by the Reader 108 as described in step 704 of FIG. 7. An example embodiment of a method for performing 1804 device authentication is illustrated in the previous FIG. 8. In one embodiment, the device authentication is performed 1804 responsive to a user accessing an application 630 for execution by the computing device 120. For example, a user selects an application from a user bar or accesses an application 730 using the operating system of the computing device 120.

Next, the device authentication module 1702 determines 1806 whether the PDK 102 is valid. If the PDK 102 is found to be invalid, connection is not authorized 1816 and the process ends without the logging in of the user.

In one embodiment, if the PDK 102 is found to be valid, the biometric authentication module 1706 determines 1806 if biometric information is available. If biometric information is available, the biometric authentication module 1706 performs 1810 biometric authentication. In one embodiment, a provider provides biometric information by swiping their finger on a Reader 108 of the computing device 120. In another embodiment, the provider provides biometric information by entering a PIN number. In yet another embodiment, the provider provides biometric information be swiping their finger on the biometric reader 370 of the PDK 102. If biometric information is not available (the provider has not swiped his finger or entered a PIN number), connection is not authorized 1820 and the process ends. If biometric information is available, biometric authentication is performed 1810. Example embodiments for performing authentication, such as biometric authentication, are described above in conjunction with FIGS. 10A-D.

In one embodiment, biometric authentication is performed 1810 responsive to an accessed application requesting or requiring biometric authentication. For example, responsive to a user accessing an application from an application menu of the computing device 120, the computing device 120 determines whether a biometric check is needed by the accessed application. If a biometric check is needed by the accessed application, the computing device 120 communicates with the Reader 108 to perform 1818 biometric authentication. In one embodiment, the computing device 120 or the application server 240 includes a database specifying whether or not an application performs a biometric check.

Once biometric authentication is performed 1810, or if no biometric authentication is not needed, the data retrieval module 1704 of the registration server 205 retrieves 1812 information from the PDK 102 of the user and the access module 1708 allows 1814 the user to access one or more applications. For example, the user is allowed 1814 to access one or more applications from the application server 240. In some embodiments where biometric authentication is not required, the access module 1708 compares the received data with data stored in the credentials database 1710 to allow or deny access.

In one embodiment, the data retrieval module 1704 identifies a service block of a registry profile stored by the PDK 102 to the computing device 120, which identifies the service block to the Reader 108, which retrieves 1812 data from the identified service block. For example, the data retrieval module 1704 identifies a registry identifier to specify a service block and the Reader 108 retrieves 1812 a record identifier and a key from the service block. The Reader 108 communicates the retrieved 1812 record identifier and the key and a PDK ID to the application server 240 in addition to a request to launch the accessed application.

In one embodiment, the accessed application 630 of the computing device 120 communicates the data retrieved from the PDK 102 to the application server 240, which communicates login credentials associated with the application 630 to the computing device 120. The computing device 120 uses the login credential information access the application 630. For example, the application 630 communicates a PDK ID, a record identifier and a key retrieved form the PDK 102 to the application server 240, which identifies a login and password from the PDK ID, the record identifier and the key. The login and password are communicated from the application server 240 to the computing device 120, which uses the login and password to launch the application 630. In another embodiment, the application 630 of the computing device 120 retrieves the login credential information associated with the data retrieved form the PDK 102 from the credentials database 320 to allow 1814 access to one or more applications. Allowing 1814 access to one or more applications is further described below in conjunction with FIG. 19.

In some embodiments, provider identifying information is stored in the PDK 102. As long as connection is established (1816—Yes) (the provider is in the proximity zone of the reader 620 of the computing device 120), access is allowed 1814. If the provider steps outside the proximity zone of the reader 620, connection is no longer established (1816—No) and the provider is logged out 1818 of the application server 240. Those skilled in the art will recognize that depending on the level of authentication desired, the need for steps 1808 and 1810 may be omitted.

In some embodiments, various rules are applied. In one embodiment, biometric input is required for users who haven't logged in for an extended period of time. In one embodiment, the extended period of time is eight hours. In another embodiment, the extended period of time is twenty four hours. In one embodiment, a secure screen saver is utilized in place of a full login/logout procedure. In another embodiment, the system allows for multiple users to be simultaneously logged in to a single workstation.

Figure 19:
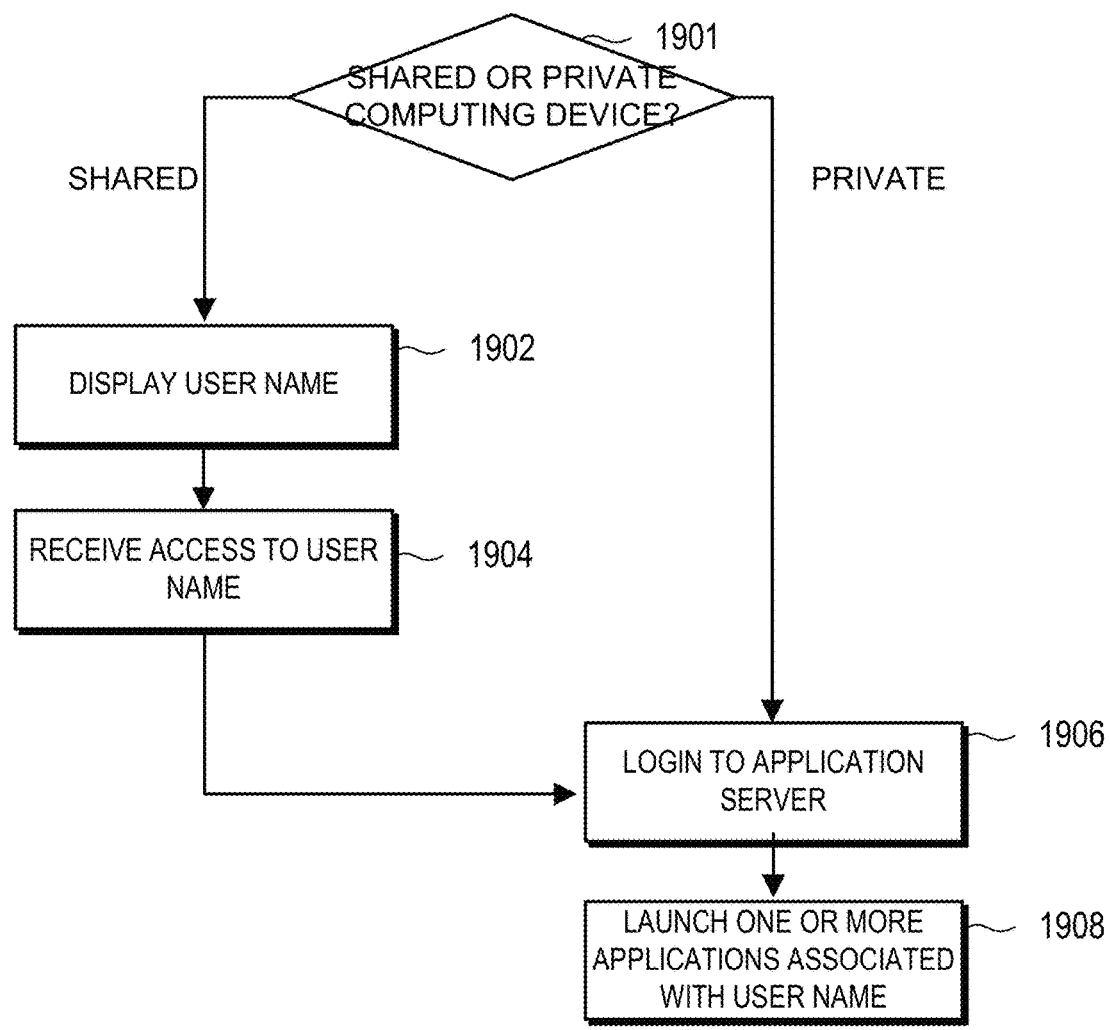
FIG. 19 is a flowchart of a method for automatically allowing access to one or more applications in accordance with the present invention.

FIG. 19 is a flowchart of one embodiment of a method 1814 for automatically allowing access to one or more applications. Initially, it is determined 1901 whether the computing device 120 is shared or private. A shared computing device 120 is able to be automatically accessed by to users associated with a plurality of PDK IDs. A private computing device 120 is able to be automatically accessed by a user associated with a specific PDK ID. For example, a shared computing device 120 is included in a location where it is accessible by multiple users, such as in a clinic room or examination room in a healthcare facility for use by different healthcare providers, while a private computing device 120 is included in a location where its accessible by a specific user, such as in a doctor's office of a healthcare facility for use by a doctor. In one embodiment, data included in the computing device 120 indicates whether the computing device 120 is shared or public.

In an alternative embodiment, rather than determine 1901 whether the computing device 120 is shared or private, the computing device 120 determines whether a user associated with the PDK 102 is a shared user or a private user. When a PDK 102 associated with a shared user communicates with a Reader 620, the computing device 120 coupled to the Reader 620 displays 1902 the user name of the user associated with the PDK 102, as further described below. Thus, if multiple PDKs 102 associated with shared users are within the proximity zone of the Reader 620, the computing device 120 communicating with the Reader 620 displays user names associated with the different shared users, and an application is not launched until one of the displayed user names is selected, as further described below. If a PDK 102 is associated with a private user, when the PDK 102 is within the proximity zone of the Reader 620, the private user is logged into 1906 the application server 240 without displaying one or more user names. Thus, when a PDK 102 associated with a private user is within the proximity zone of a Reader 620, the private user is logged into 1906 the application server 240, as further described below.

If the computing device 120 is shared, after biometric authentication is performed 1810 and the data retrieval module 1704 of the registration server 205 retrieves 1812 information from the PDK 102 of the user, the computing device 120 displays 1902 a user name associated with the information from the PDK 102. In one embodiment, if multiple PDKs 102 are within the proximity zone of the Reader 620, and the computing device 120 is shared, the computing device 120 displays 1902 user names associated with each of the PDKs 102 within the proximity zone of the Reader 620.

The computing device 120 receives 1904 an input accessing the displayed user name. If multiple user names are displayed 1902, the computing device 120 receives 1904 an input accessing one or the displayed user names. The computing device 120 or the Reader 604 then logs into 1906 the application server 240, or to the application 630, using credentials associated with the accessed user name. Using the credentials associated with the accessed user name, the computing device 120 launches 1908 one or more applications associated with the accessed user name.

For example, the application server 240 associates two or more applications with the accessed user name, and responsive to the computing device 120 receiving 1904 an access to the user name, the application server 240 communicates data to the computing device 120 to launch 1908 the two or more applications associated with the accessed user name. In one embodiment, the applications associated with the user name are stored in the application server 240 as a scenario and a user specifies a default scenario to identify applications that are automatically launched 1908 when a user is automatically logged into a computing device 120 using data stored on a PDK 102.

If the computing device 120 is private, after biometric authentication is performed 1810 and the data retrieval module 1704 of the registration server 205 retrieves 1812 information from the PDK 102 of the user, the computing device 120 or the Reader 620 then logs into 1906 the application server 240, or to the application 630, using credentials associated with the accessed user name. Using the credentials associated with the accessed user name, the computing device 120 launches 1908 one or more applications associated with the accessed user name. Hence, a private computing device 120 automatically launches 1908 one or more applications when the PDK 102 associated with a user authorized to use the private computing device 120. For example, when the PDK 102 associated with a doctor enters the proximity zone of the Reader 620 associated with a computing device 120 in the doctor's office, the computing device 120 automatically launches one or more applications associated with the doctor.

In addition to automatically launching one or more applications when a PDK 102 associated with a user is within a proximity zone of a reader coupled to a computing device 120, the auto login server 220 and/or the application server 240 allow a user to customize the one or more applications launched by the computing device 120. In some embodiments, the auto login server and/or the application server 240 also modify the one or more launched application responsive to user interaction with previously launched applications.

Figure 20:
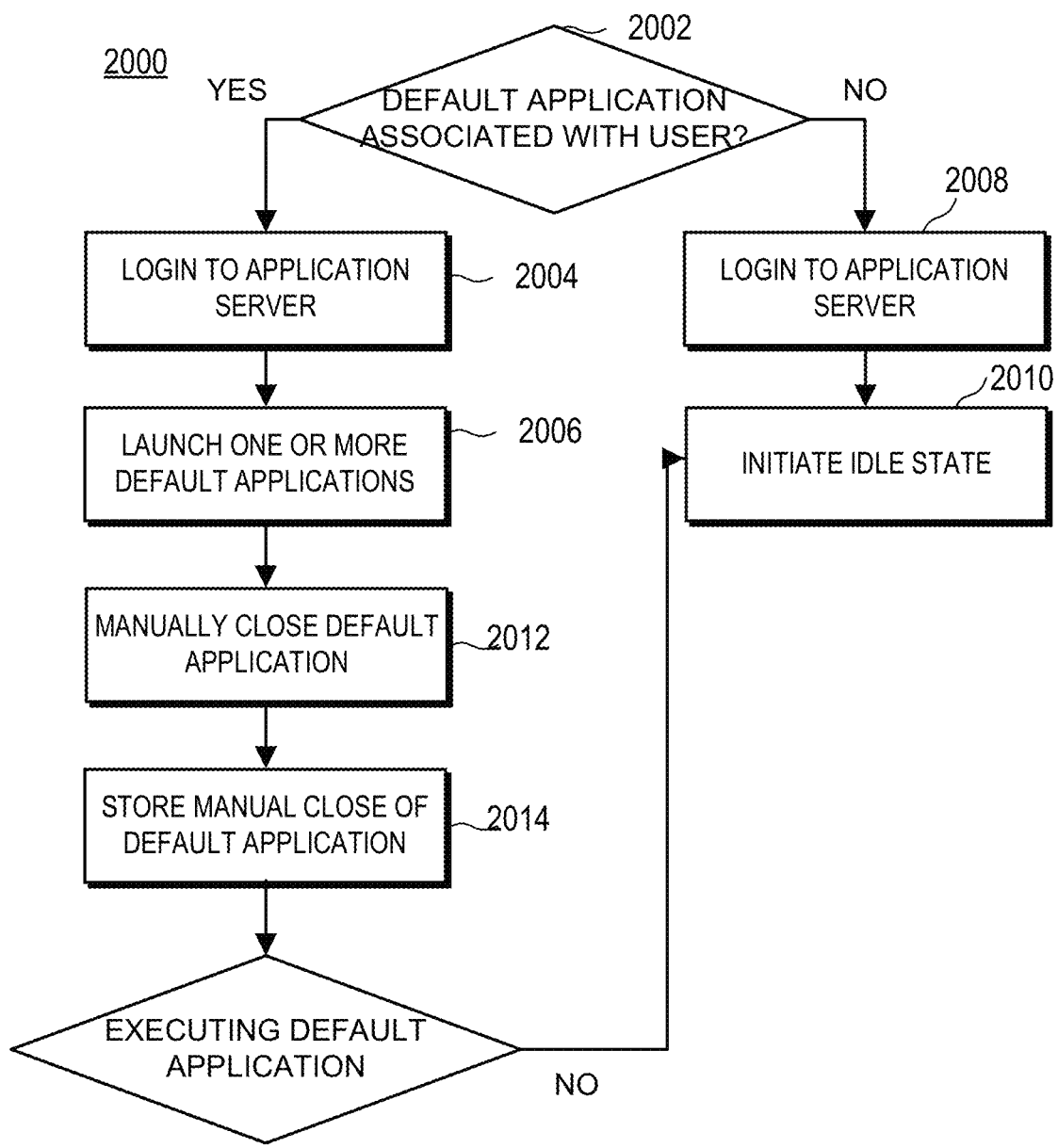
FIG. 20 is a flowchart of a method for identifying one or more applications launched when a user is within the proximity zone of a reader in accordance with the present invention.

FIG. 20 illustrates one embodiment of a method 2000 for identifying one or more applications automatically launched for a user when the user is proximate to a Reader 620. Initially, the auto login server 220 determines whether one or more default applications are associated with a user identified from a PDK 102. A default application is automatically launched when data from a PDK 102 authenticates a user to access a computing device 120. In one embodiment, the auto login server 220 determines 2002 whether one or more default applications are associated with a user and logs in 2004 to the application server 240 using login credentials identified from the data received from the PDK 102. Alternatively, the application server 240 determines 2004 whether one or more default applications are associated with the user.

If one or more default applications are associated with a user, the application server 240 launches 2006 the one or more default applications by communicating data associated with the one or more default applications to a computing device 120 coupled to the Reader 620 from which the auto login server 220 or the application server 240 received data from the PDK 102. In one embodiment, the application server 240 applies application-specific preferences when launching 2006 a default application. For example, the application server 240 associates an application location preference with a user, so that when a default application is launched 2006 the application location preference identifies a specific location within the default application that is initially accessed. For example, the application server 240 identifies a specific text entry region of an application and when the application is launched the specified text entry region is accessed, allowing a user to begin entering text data in the specified text entry region without first selecting the text entry region. While described above in conjunction with default applications, in an embodiment the user's application specific preferences are also applied when a user manually launches an application, allowing the application server 240 to provide increased user-customization to simplify application use.

After a default application is launched 2006, a user may manually close 2012 the default application by interacting with the default application using the computing device 120. When a user manually closes 2012 a default application, the computing device 120 communicates data to the auto login server 220 and/or the application server indicating that the default application has been manually closed. The auto login server 220 or the application server 240 stores 2014 data indicating that a default application has been manually closed. In one embodiment, when a user logs out of the computing device 120 and does not exit the proximity zone of the Reader 620 coupled to the computing device 120 after manually closing the default application, the manually closed default application is not automatically launched 2006 when the user again logs into the computing device 120. For example, if a user logs off of the computing device 120 after manually closing a first default application and does not exit the proximity zone of the Reader 620, when the user again logs in to the computing device 120, based on the stored data, the auto login server 220 or the application server 240 does not automatically launch the first default application. However, once the user leaves the proximity zone of the Reader 620 after manually closing the first default application, once the user re-enters the proximity zone of the Reader 620 and logs into the computing device 120, the auto login server 220 or the application server 240 again automatically launches 2004 the first default application.

If a user manually closes each default application associated with the user, the application server 240 communicates data to the computing device 120 indicating that no applications are executing, causing the computing device 120 to initiate 2210 an idle state where the user is logged into the computing device 120 and to the application server 240, allowing the user to manually launch one or more applications from the computing device 120.

However, if no default applications are associated with a user, the application server 240 communicates with the computing device 120 coupled to the Reader 620 from which the auto login server 220 or the application server 240 received data from the PDK 102 to initiate 2010 an idle state. In one embodiment, the application server 240 communicates data to the computing device 120 indicating that no applications are executing, causing the computing device 120 to initiate 2210 the idle state.

The Reader 620 and PDK 102 may also be used to lock a computing device 120 coupled to the Reader 620 in addition to limiting use of the computing device 120. For example, the Reader 620 and PDK 102 may be used to limit execution of certain applications using the computing device 120 while allowing users to use other applications locally stored on the computing device 120. For example, the PDK 102 and Reader 620 are used to limit the users permitted to execute a set of healthcare applications, such as a patient record editor, while additional users may freely access a web browser included on the computing device 120. However, in some embodiments, it is desirable to further limit use of the computing device 120 so that users are unable to access applications using the computing device 120 unless a valid PDK 102 associated with the user is in the proximity zone of a Reader 620 coupled to the computing device 120.

Figure 21:
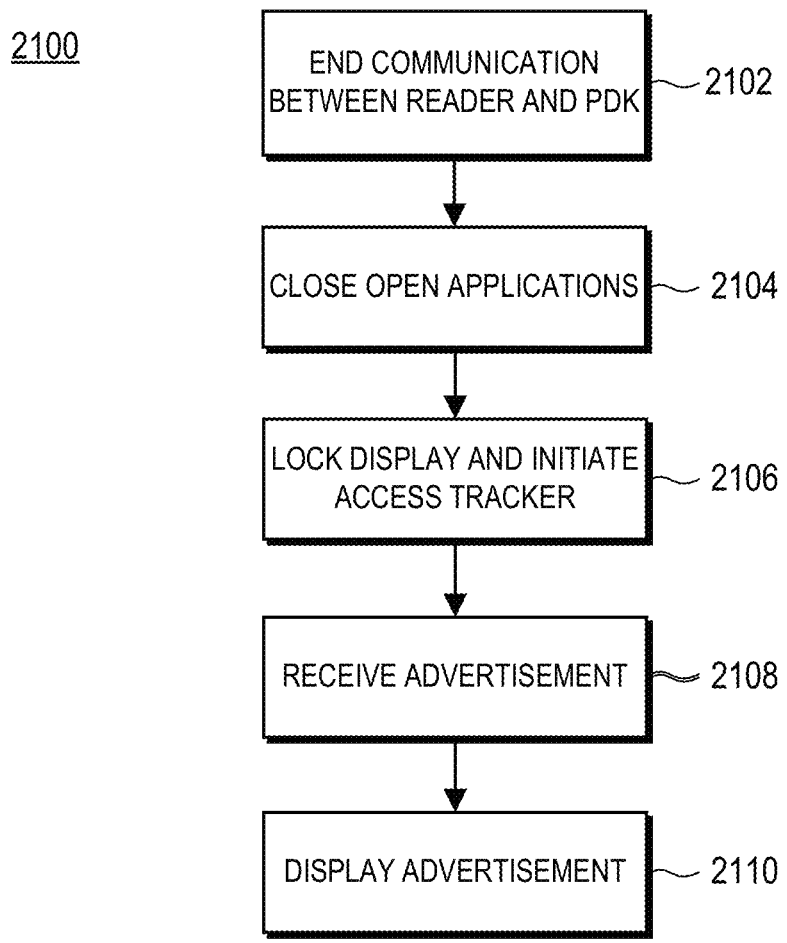
FIG. 21 is a flowchart of a method for locking a computing device coupled to a reader responsive to a PDK exiting the proximity zone of the reader in accordance with the present invention.

FIG. 21 describes one embodiment of a method for locking a computing device 120 using a Reader 620 coupled to the computing device 120 and a PDK 102. Responsive to a PDK 120 leaving the proximity zone associated with a Reader 620, the Reader 620 communicates data to the computing device 120 and to the application server 240 to close 2104 applications currently running on the computing device 120. In one embodiment, the data communicated from the Reader 620 to the application server 240 logs the user associated with the PDK 102 out of the application server 240. By closing 2104 applications executed by the application server 240 and by the computing device 120 when a PDK 102 leaves the proximity zone of the Reader 620, the security of the computing device 120 is increased.

Responsive to data from the Reader 620 indicating the PDK 102 has left the proximity zone of the Reader 620, after closing 2104 open applications, the computing device 120 locks 2106 its display device and initiates an access tracking process. In one embodiment, when the display device 618 is locked 2104, a predefined image is displayed on the display device 618, such as a logo or other image associated with the location where the computing device 120 is located. Alternatively, when the display device 618 is locked 2104, the display device 2104 does not display an image or is a blank screen. The access tracking process is computer-readable data stored in the storage device 608 or the memory 606 of the computing device 120 that, when executed by the processor 602, monitors the keyboard 610, the pointing device 614 or other input/output devices of the computing device 120 for inputs. In one embodiment, the access tracking process unlocks the display device 618 responsive to identifying an input received by an input/output device 120. However, until the access tracking process identifies an input received by an input/output device 120, the display 618 is locked 2104, as further described above.

In one embodiment, the computing device 120 receives 2108 one or more advertisements and displays 2110 the one or more advertisements when the display device 618 is locked rather than displaying a fixed image or blanking the display device 618. For example, the computing device 120 includes one or more advertisements in its storage device 608 and displays 2110 the one or more advertisements when the display device 618 is locked. In one embodiment, the computing device 120 alternates the advertisements displayed 2110 at different time intervals, allowing different advertisements to be displayed 2110 while the display device 618 is locked. In an alternative embodiment, the computing device 120 receives 2108 the one or more advertisements from a third party site 140 or from the application server 240 and displays 2110 one or more of the received advertisements while the display device 618 is locked 2106. In one embodiment, the application server 240 or the third party site 140 receives data from the computing device 120 and modifies the advertisements received 2108 by the computing device 120 responsive to the data received from the computing device 120. For example, the third party site 140 or the application server 240 receives data from the computing device 120 associated with a user or patient whose information has been recently accessed by the computing device 120. The computing device 120 then receives 2108 advertisements from third party site 140 or the application server 240 associated with the user or patient information. This allows the computing device 120 to display 2110 advertisements relevant to the recently accessed user or patient when the display device 618 is locked.

Figure 22:
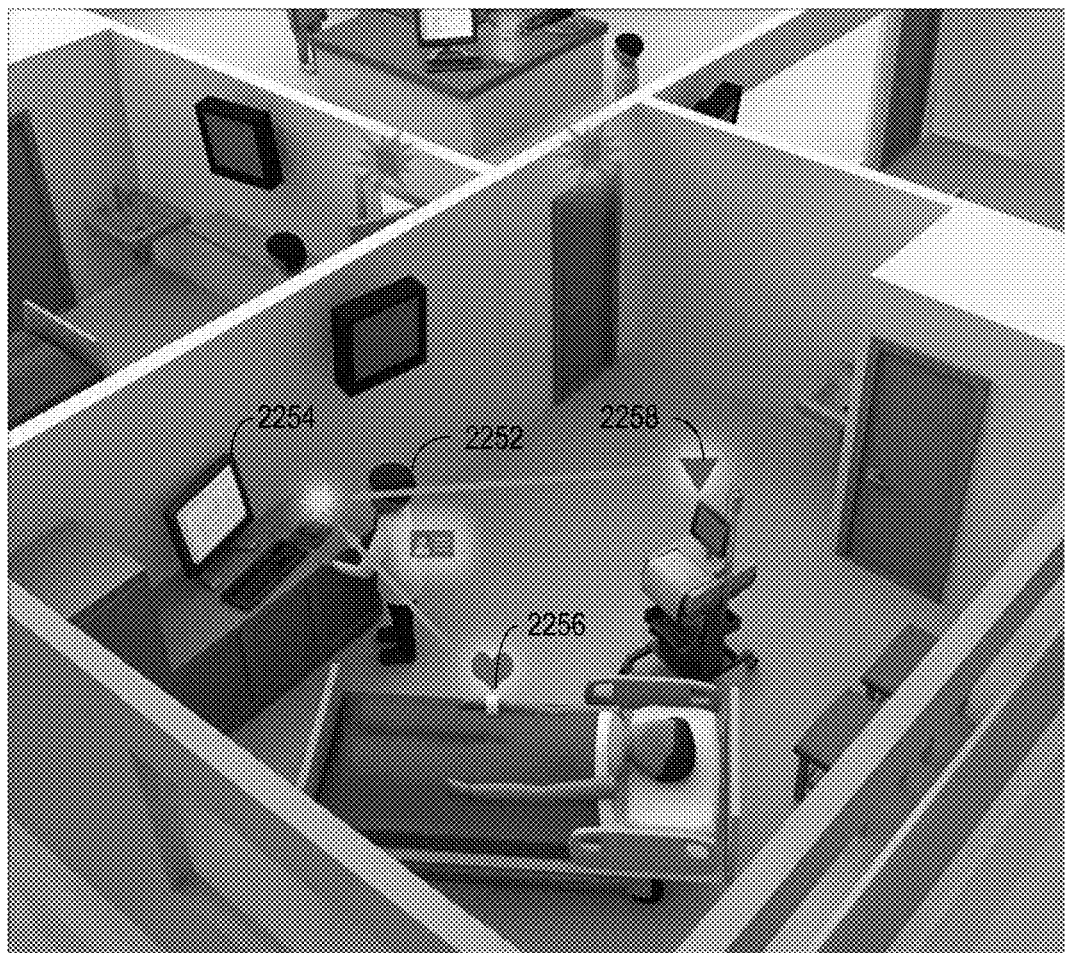
FIG. 22 is a graphical representation of one embodiment of automatic login of users in accordance with the present invention.

FIG. 22 is a graphical representation of one embodiment of automatic login of users. In this illustration, the user is a healthcare provider 2252 with a unique identifying PDK. When the healthcare provider 2252 having its associated PCK enters a patient's room and walks up to a computing device 2254, the reader of the computing device 2154 retrieves information from the provider's 2252 PDK and automatically logs the provider 2252 into the software system.

If PDKs 2256, 2258 are also used to identify the patient and equipment in the patient's room, the reader of the computing device 2254 also retrieves information from those PDKs 2256, 2258. In one embodiment, the computing device displays user names associated with the PDKs 2256, 2258 as well as a user name associated with the healthcare provider 2252 and the healthcare provider 2252 selects the appropriate user name to log in to the computing device. One or more default applications are then launched by the computing device for access by the healthcare provider 2252.

Figure 23:
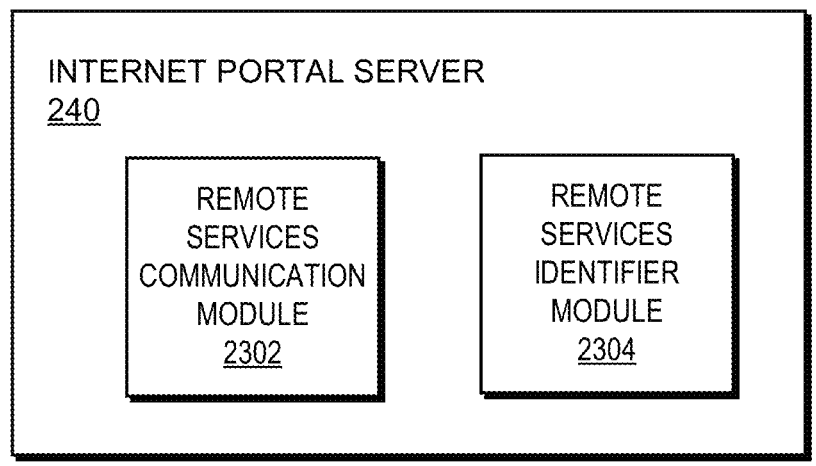
FIG. 23 is a block diagram of a portal server in accordance with the present invention.

FIG. 23 is a block diagram illustrating an embodiment of a portal server 230. The portal 230 provides a consistent interface to the third party site 140. Such services may include receiving advertisement data, accessing a patient's virtual database records or insurance information or sending prescription requests to remote pharmacies. The portal server 240 includes a remote services communication module 2302 and a remote services identifier module 2304.

Figure 24:
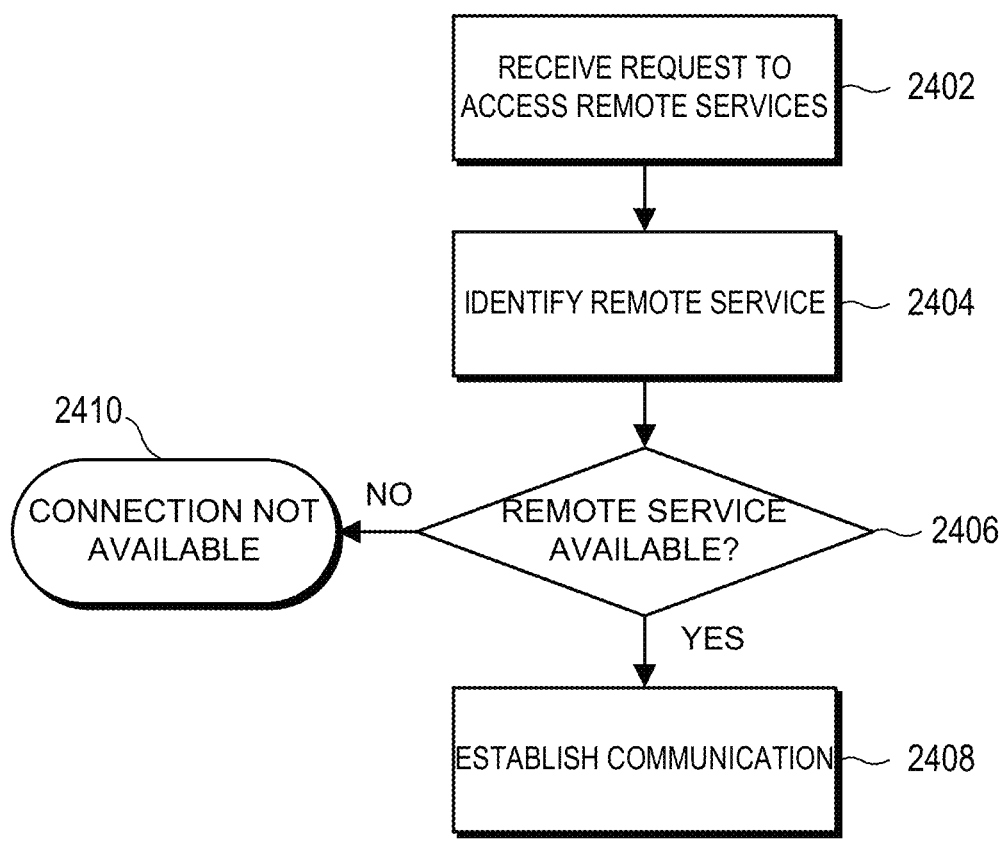
FIG. 24 is a flowchart of a method for communicating with remote services provided by a third party site in accordance with the present invention.

FIG. 24 is a flowchart illustrating one embodiment of a method 2400 for communicating with remote services provided by a third party site 140. The remote services communication module 2302 receives 2402 a request from a computing device 120 to access one or more services, or data, provide by the third party site 140. The remote services identifier module 2304 identifies 2404 which remote service to contact. For example, if the request includes insurance information as well as payment information, the remote services identifier module 2304 determines that the request from the computing device 120 needs to be communicated to a particular third party site 140.

A determination is then made to determine whether the requested remote service or data is available 2406. If the remote service is not available (2406—No), then a connection to the third party site 140 is not established. In some embodiments, an error message is sent to the computing device 120 with a notification of the unavailability of the requested remote service. If the remote service is available (2406—Yes), communication with an appropriate third party site 140 is established.

FIG. 25 is a flow chart of one embodiment of a method 2500 initially storing data on a PDK 102 during an initialization or registration process. In the example of FIG. 25, a PDK 102 is initialized using a computing device 120. Additionally, the initial configuration and data storage of the PDK 102 is witnessed and authenticated by a specialized trusted Notary. In one embodiment, the Notary is associated with a Notary PDK. For example, the computing device 120 includes data identifying PDK IDs associated with one or more notaries.

In one embodiment, the computing device 120 initially identifies 2502 one or more Notaries to witness PDK 102 initialization. For example, a user associated with a master PDK accesses the computing device 120 and identifies one or more PDK identifiers associated with one or more Notaries. Only a user associated with the master PDK 102 is permitted to identify 2102 PDK IDs associated with one or more Notaries. For example, a user associated with a Master PDK 102 identifies one or more PDK IDs associated with Notaries, allowing the computing device 120 to locate Notaries by comparing PDK IDs from a Reader 620 to the Notary PDK IDs identified by the Master PDK.

After a Notary is identified 2502, the computing device 120 establishes 2504 communication with the PDK 102 to be initialized and establishes 2504 communication with a PDK 102 associated with a Notary, as further described above. The computing device 102 receives information from the PDK 102 to be initialized to determine if the PDK 102 to be initialized is authorized for initialization and also receives information from the PDK 102 associated with the Notary to determine if the Notary is authorized to perform the initialization. If both the PDK 102 to be initialized and the PDK 102 associated with the Notary are authorized to perform the initialization, the computing device 120 receives 2508 biometric data from a user associated with the PDK 102 to be initialized. The Notary witnesses the receipt 2508 of biometric data by the computing device 120, either in person or remotely, to ensure that the received biometric data is trustworthy. The computing device 120 then stores 2510 the received biometric data. In one embodiment, the computing device 120 communicates the biometric data to the PDK 102 to be initialized for storage and also locally stores 2510 the biometric data. In another embodiment, the computing device 120 communicates the received biometric data to a central registry 114 or a private registry 116 for storage along with the ID of the PDK 102 to be initialized. For example, the central registry 114 or a private registry 116 includes a PDK ID of the PDK 102 to be initialized, biometric data associated with the PDK ID of the PDK 102 to be initialized and other user data associated with the PDK ID of the PDK 102 to be initialized.

Figure 26:
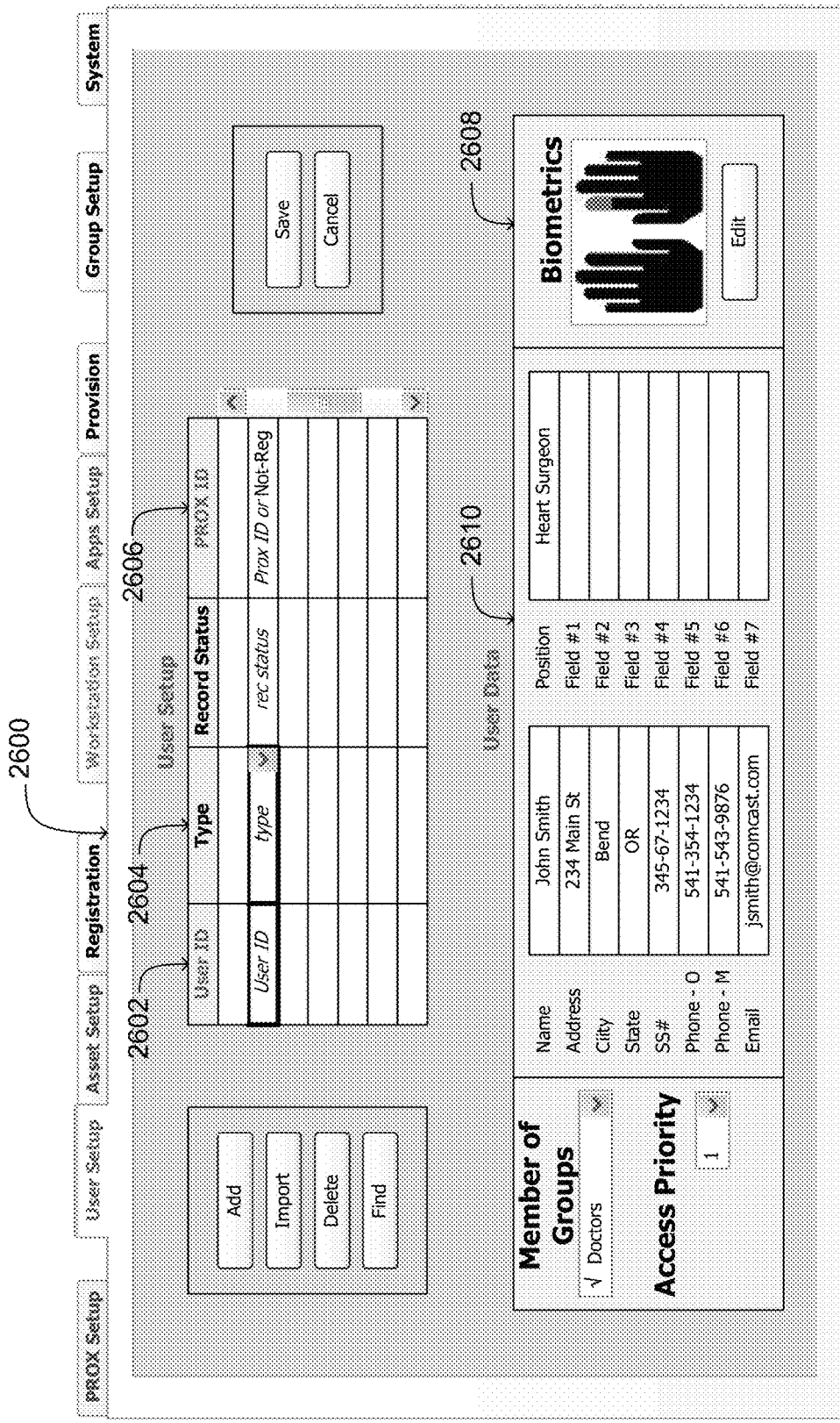
FIG. 26 is an example user interface for configuring user information associated with a PDK in accordance with the present invention.

FIG. 26 shows an example user interface 2600 for configuring user information associated with a PDK 102. In one embodiment, the user interface 2600 is displayed by a computing device 120 that is used to initialize a PDK 102. The user interface 2600 includes a user configuration region having a user identifier editor 2602, a user type editor 2604 and a PDK ID editor 2606. Interacting with the user identifier editor 2602, the user type editor 2604 and the PDK ID editor 2606 allows a user, such as an administrator, to specify a user identifier associated with a PDK ID and to associate a user type with the user name and with the associated PDK ID. In one embodiment, the user type editor 2604 allows a user to select from a predefined listing of user types. For example, the user type editor 2604 allows a user to specify whether a user identifier is associated with a general user, with an administrator or with a Notary. Depending on the user type, the functionality of a user is modified. For example, a user identifier associated with an administrator is able to modify execution of different applications or customize application execution for other users while a user identifier associated with a Notary is authorized to authenticate the accuracy of biometric data received by the computing device 120.

Additionally, the user interface 2600 includes a user data summary 2610 that displays data associated with a user identifier, such as contact information for the user, a job title for the user and a listing of groups to which the user belongs. In one embodiment, a user accesses the user data summary 2610 to identify one or more groups to which the user belongs. A biometric data summary 2608 is also displayed to identify the type of biometric data associated with a user and allowing a Notary to modify the biometric data by interacting with the biometric data summary. For example, a Notary may access the biometric data summary 2608 to obtain a different type of biometric data associated with the user.

Figure 27:
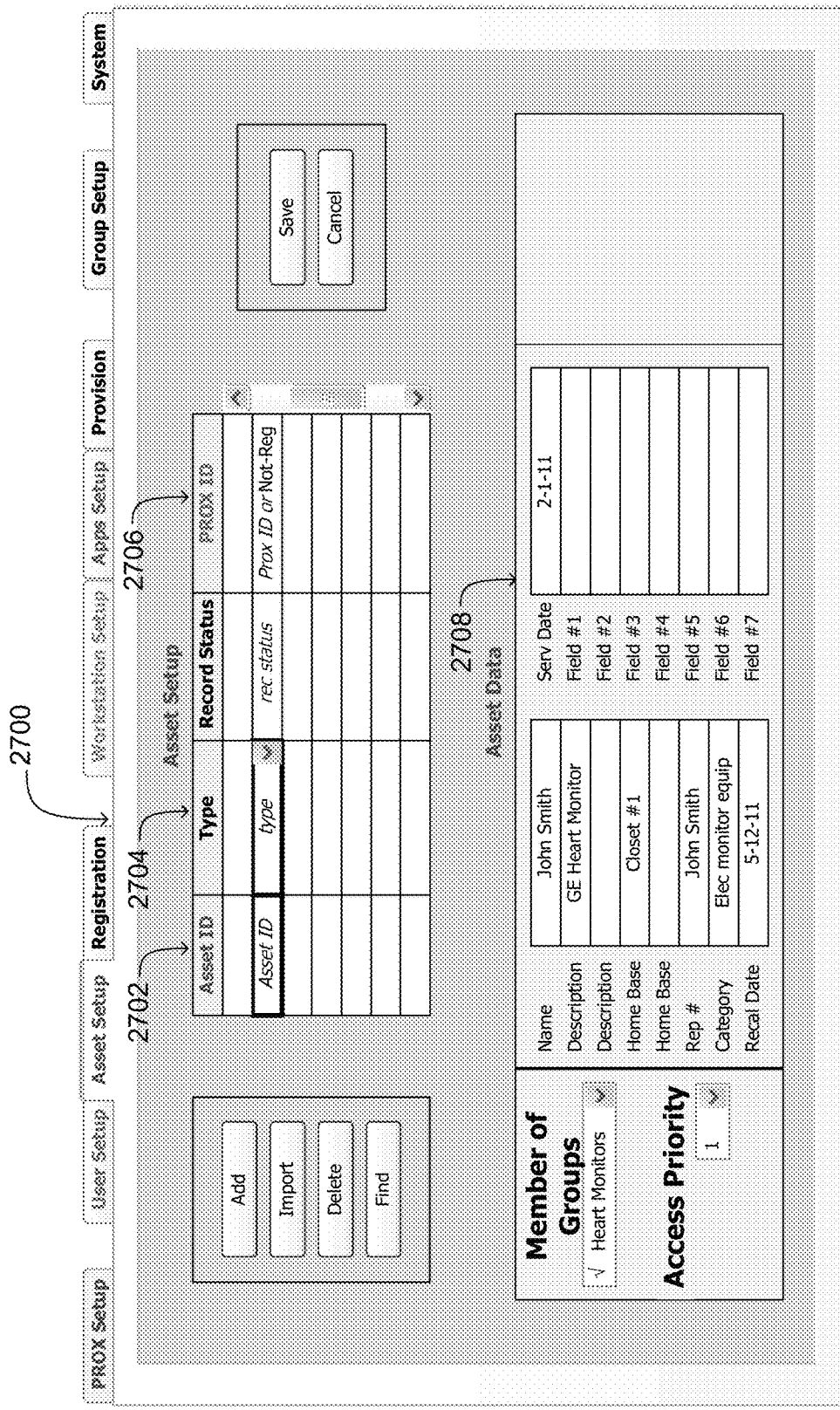
FIG. 27 is an example user interface for configuring asset information associated with a PDK in accordance with the present invention.

FIG. 27 shows an example user interface 2700 for configuring asset information associated with a PDK 102. While FIG. 26 describes configuration of a user, such as an individual, associated with a PDK 102, FIG. 27 describes configuration of information associated with an asset, such as equipment or supplies, associated with a PDK 102. In one embodiment, the user interface 2700 is displayed by a computing device 120 that is used to initialize a PDK 102. The user interface 2700 includes an asset configuration region having an asset identifier editor 2702, an asset type editor 2704 and a PDK ID editor 2706. Interacting with the asset identifier editor 2702, the asset type editor 2704 and the PDK ID editor 2706 allows a user, such as an administrator, to specify a user identifier associated with a PDK ID and to associate a user type with the user name and with the associated PDK ID. In one embodiment, the asset type editor 2704 allows a user to select from a predefined listing of user types. For example, the asset type editor 2704 allows a user to specify whether an asset identifier is associated with a general asset, with an administrator or with a Notary. Depending on the asset type, the functionality of an asset is modified, as described above in conjunction with FIG. 26.

Additionally, the user interface 2700 includes an asset data summary 2708 that displays data associated with an asset identifier, such as an asset name, an asset description, an asset location, an asset category, an asset service data or other data describing attributes of the asset. In one embodiment, a user accesses the asset data summary 2708 to identify one or more groups to which the user belongs.

Figure 28:
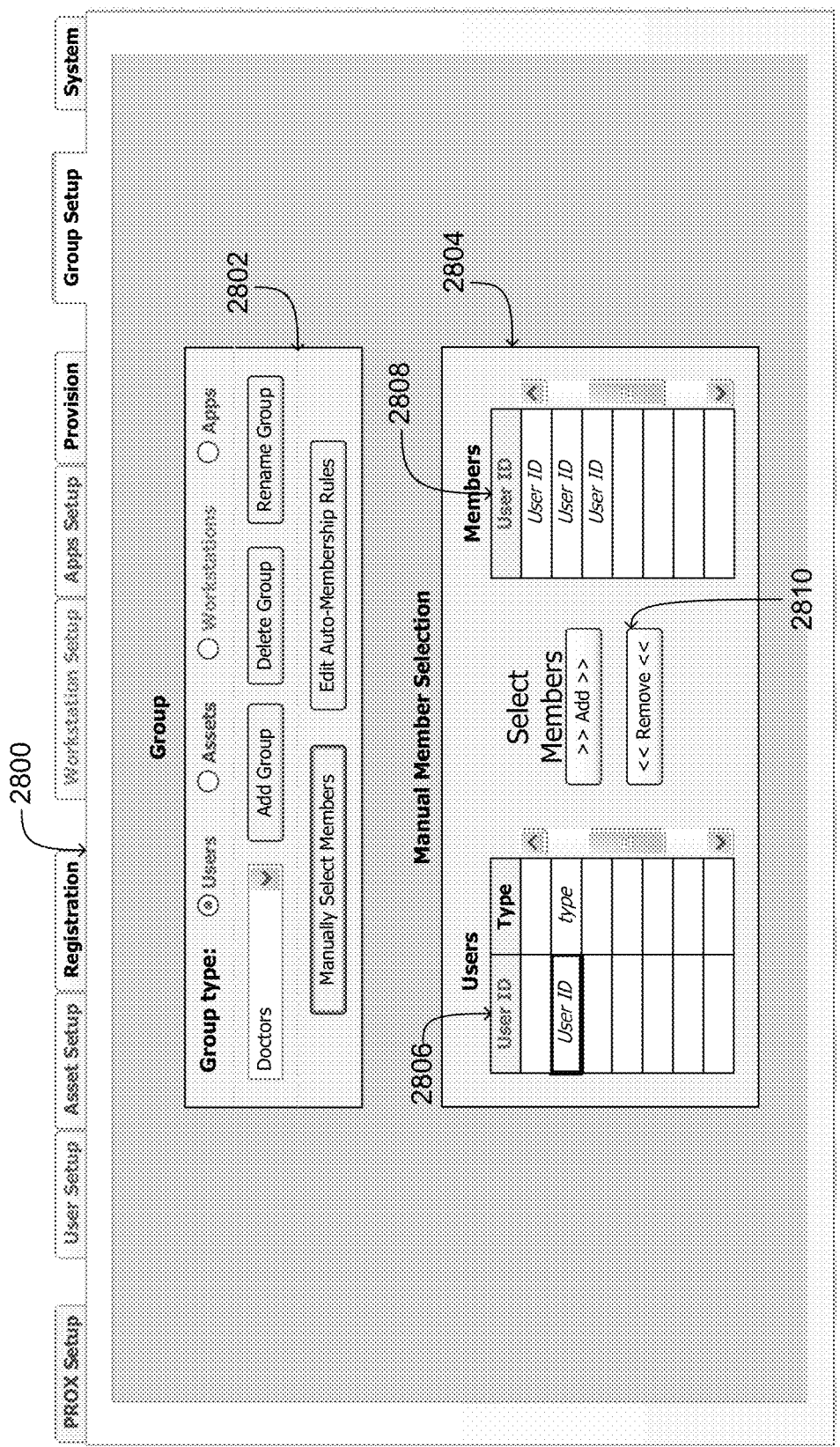
FIG. 28 is an example user interface for manually identifying assets or users included in a group in accordance with the present invention.

In addition to interacting with a user data summary 2610 or an asset data summary 2708 to associate users or assets with a group, one or more user interfaces may be used to automatically or manually associate user identifiers or asset identifiers with one or more groups. FIG. 28 illustrates an example user interface 2800 allowing a user to manually identify members, such as users and/or assets, included in a group. The user interface 2800 includes a group description 2802 allowing a user to identify a group type, specify a group name and to modify the group name or group type.

A member selection region 2804 identifies users and/or assets included in a central registry 114 and/or a private registry 116 using a user listing 2806 and identifies users and/or assets included in the group identified by the group description 2802 using a member listing 2808. In one embodiment, a user selects a user identifier, or an asset identifier, from the user listing 2806 and accesses a group modification region 2810, causing the selected user identifier or asset identifier to be included in the group identified by the group description 2802. Once the group modification region 2810 is accessed, the selected group identifier, or asset identifier, is displayed in the member listing 2808 rather than in the user listing 2806. Similarly, a user selects a user identifier, or an asset identifier, from the member listing 2808 and accesses a group modification region 2810 to remove the selected user identifier, or asset identifier, from the group identified by the group description 2802.

Figure 29:
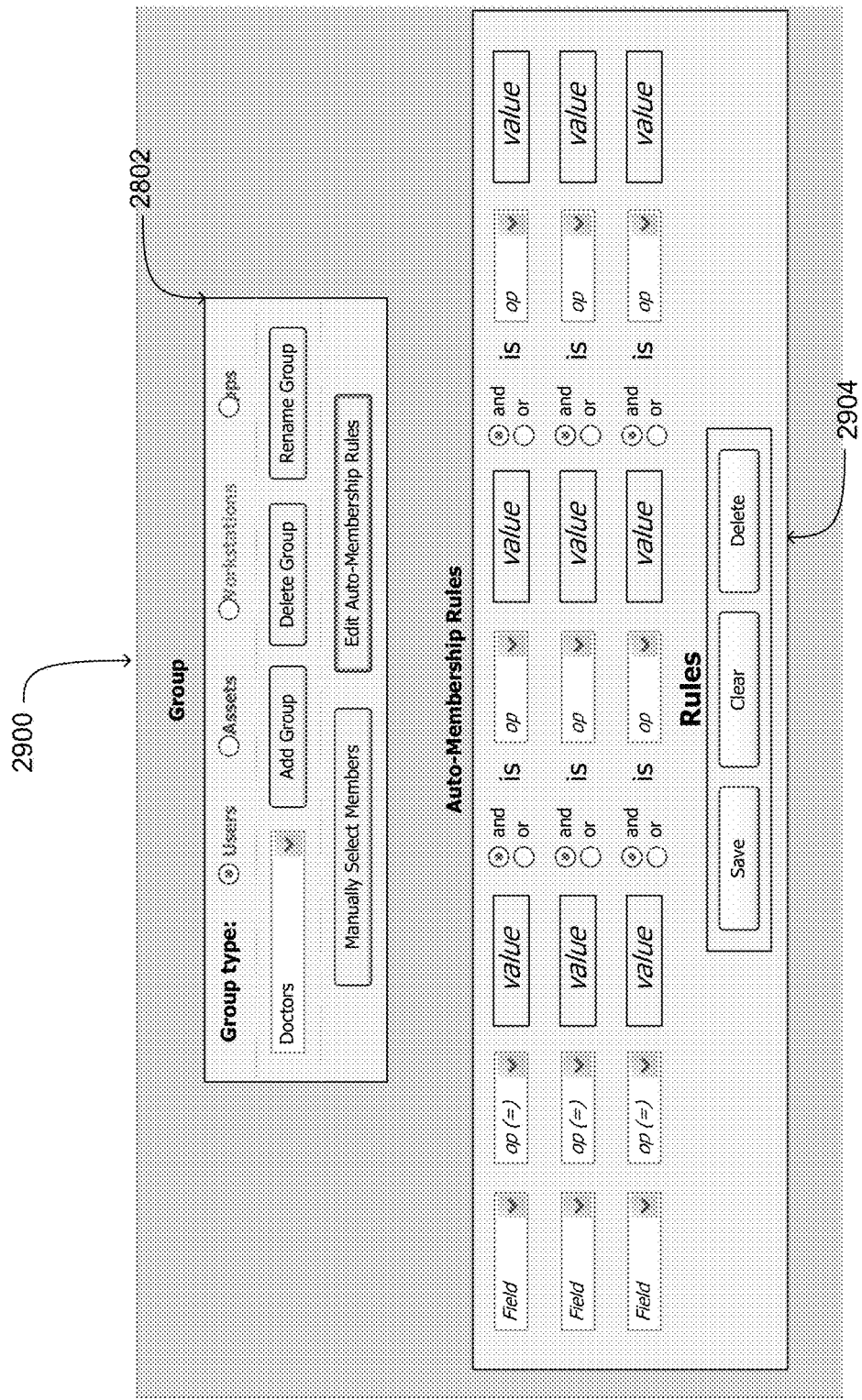
FIG. 29 is an example user interface for automatically identifying assets or users included in a group in accordance with the present invention.

FIG. 29 illustrates an example user interface 2900 allowing a user to automatically include users and/or assets in a group based on one or more criteria. The user interface 2900 includes a group description 2802 allowing a user to identify a group type, specify a group name and to modify the group name or group type.

A rule specification region 2904 receives input identifying one or more rules for identifying users and/or assets for inclusion in a group. For example, the rule specification region 2904 receives rules for including a user or asset in the group identified by the group description 2802. In one embodiment, the rule specification region 2904 receives input identifying values for one or more fields associated with a user, or an asset, and a user or asset including fields matching the values identified by the rules is automatically associated with the group identified in the group description 2802. In the example shown by FIG. 29, the rule specification region 2904 allows a user to specify combinations of fields and values associated with the fields to customize the users or assets included in the group. For example, a rule may include logical operators, such as "AND" or "OR," to describe combinations of values and/or fields.

Figure 30:
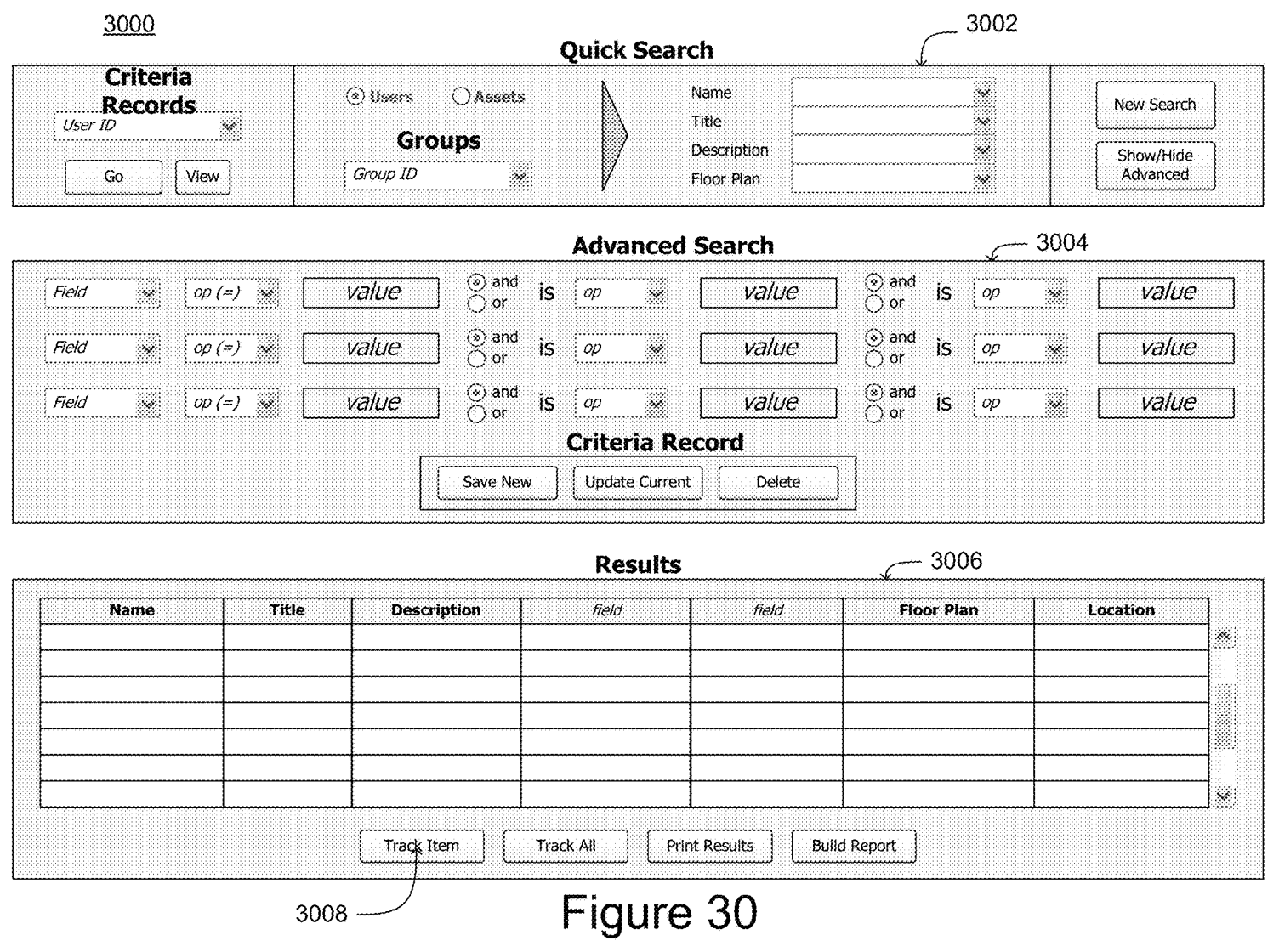

FIG. 30 is an example of a user interface 3000 for tracking a user or asset associated with a PDK 102 from a computing device 120. The user interface 3000 receives input from a user to identify a user or asset to be tracked by the tracking server 210. In the example of FIG. 30, the user interface 3000 includes a quick search interface 3002 and an advanced search interface 3004 as well as a result listing 3006.

The quick search interface 3002 receives input from a user for performing simple searches based on a limited amount of data associated with a user or an asset. For example, the quick search interface 3002 receives input identifying a name, a title, a description or a location of a user or an asset and identifies the user or asset matching the received input. The quick search interface 3002 also allows specification of a group identifier to retrieve assets or users included in the specified group.

The advanced search interface 3004 receives input for performing advanced searches based on multiple data associated with a user or an asset or based on combinations of data associated with a user or an asset. In one embodiment, the advanced search interface 3004 receives input identifying values for one or more fields associated with a user or an asset that are used to identify one or more users or assets including fields having values matching those identified by the values, or combination of values, received by the advanced search interface 3004. In the example shown by FIG. 30, the advanced search interface 3004 allows a user to specify combinations of fields and values associated with the fields to identify assets or values. For example, the advanced search interface 2004 receives input identifying values for multiple fields and logical operators describing a number of values for different fields. For example, the advanced search interface 3004 allows values for fields to be combined using logical operators, such as "AND" or "OR," to describe combinations of values and/or fields.

The result listing 3006 displays data associated with users or assets that match the search criteria received by the quick search interface 3002 or the advanced search interface 3004. For example, the result listing 3006 displays a name, a title, a description, a floor plan and a location associated with different assets or users matching the search criteria. In one embodiment, the result listing 3006 receives input selecting one or more of the search results and a tracking input 3008 causes the tracking server 210 to monitor the location of the assets or users selected via the result listing 3006. In one embodiment, a first input received by the tracking input 3008 causes the tracking server 210 to track the selected assets or users while a second input received by the tracking input 3008 causes the tracking server 210 to track each of the assets or users identified by the result listing 3006.

Figure 31:
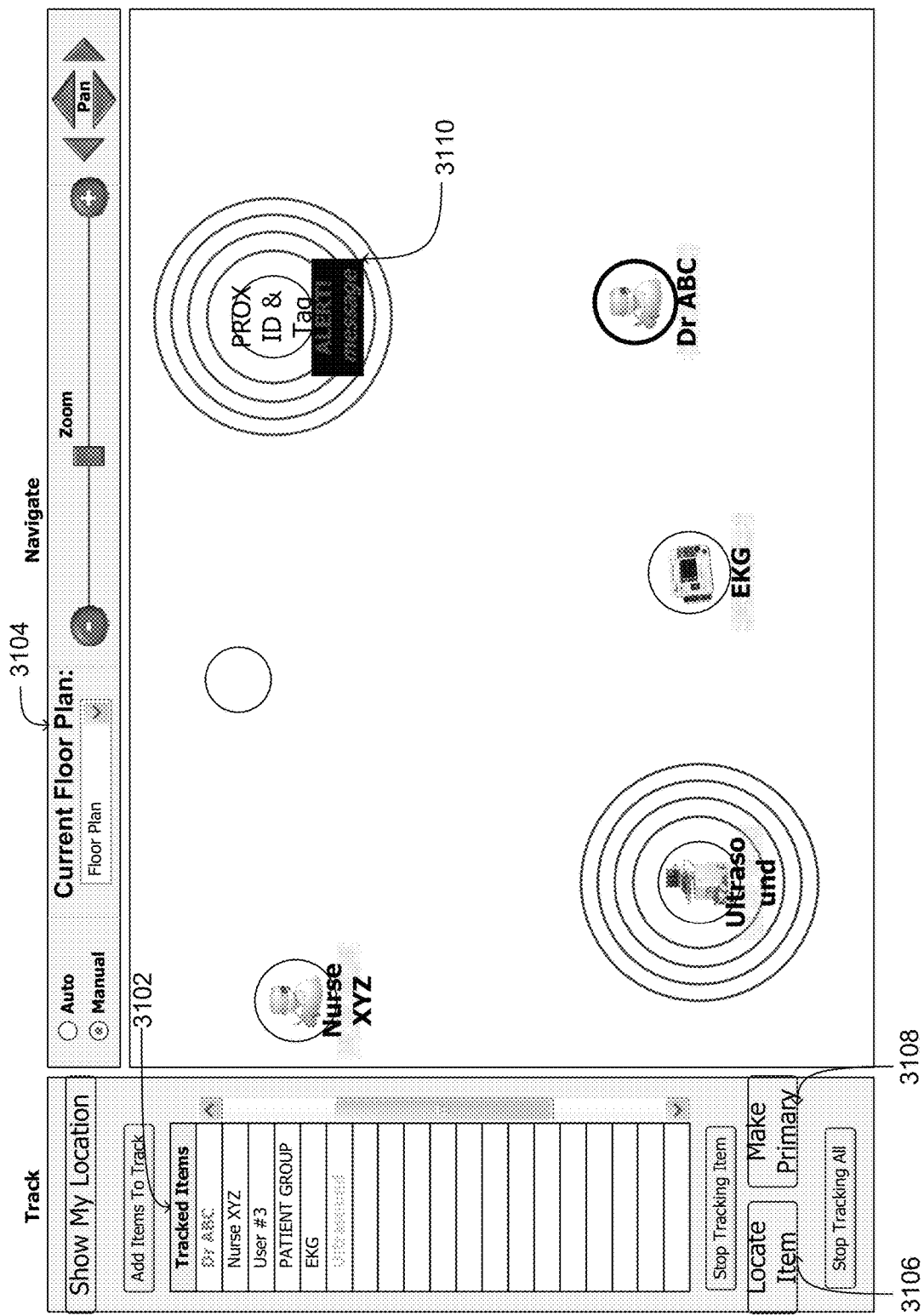
FIG. 31 is an example user interface for identifying the location of a tracked user or asset associated with a PDK in accordance with the present invention.

FIG. 31 is an example of a user interface 3100 for identifying the location of a tracked user or asset associated with a PDK 102 from a computing device 120. The user interface 3100 displays data from the tracking server 210 indicating the location of one or more assets or users tracked by the tracking server 210. In the example of FIG. 30, the user interface 3100 includes a tracked item listing 3102, a navigation interface 3104, an item location selector 3106 and a primary item selector 3108.

The tracked item listing 3102 displays an item identifier associated with users or assets tracked by the tracking server 210. For example, the tracked item listing 3102 displays a user name or asset name associated with the tracked items. In one embodiment, the tracked item listing 3102 receives input selecting a user or asset and a subsequent input received by the item location selector 3106 or the primary item selector 3108 modifies the user interface 310. Items included in the tracked item listing 3102 may be manually identified by user input or may be automatically included based on one or more criteria of a user or an asset.

After selecting a user or asset form the tracked item listing 3102, an input received by the item location selector 3106 causes the user interface 3100 to visually distinguish the location of the selected item in the navigation interface 3104. For example, the navigation interface 3104 visually distinguishes the selected item from other tracked items responsive to the item location selector 3106. In the example of FIG. 31, the navigation interface 3104 modifies the color used to display the selected item and displays rings around the selected item responsive to the item location selector 3106 receiving an input.

After selecting a user or asset form the tracked item listing 3102, an input received by the primary item selector 3108 causes the user interface 3100 to make the selected item the primary item so that the navigation interface 3104 is modified to keep the selected item visible. For example, the navigation interface 3104 scrolls as the primary item moves to keep the primary item visible in the navigation interface 3104. Additionally, the navigation interface 3104 may visually differentiate the primary item from other tracked items by changing the color used to display the primary item or otherwise modifying the presentation of the primary item relative to other tracked items.

The navigation interface 3104 displays the location of the items identified in the tracked item listing 3102 in a graphical representation of the environment including the tracked items. For example, the navigation interface 3104 displays a floor plan of an environment including the tracked items with the location of the tracked items overlaid on the floor plan. In one embodiment, the navigation interface 3104 includes navigation controls allowing a user to zoom in or out of the graphical representation of the environment including the tracked items or to pan across the graphical representation of the environment including the tracked items. The navigation interface 3104 may also include a selector allowing modification of the graphical representation of the environment including the tracked items. For example, the navigation interface 3104 allows modification of the floor plan on which the positions of the tracked items are overlaid.

In one embodiment, the navigation interface 3104 also displays one or more alert notifications 3110 associated with tracked items. An alert notification 3110 is displayed responsive to a tracked item meeting one or more criteria. For example, an alert notification 3110 is displayed when the tracking server 310 receives data from a PDK 102 indicating that the temperature proximate to an asset or a user is within a specified range. The alert notification 3110 visually differentiates the item meeting the criteria from other tracked items. In one embodiment, the alert notification 3110 displays a text message describing the alert. A user interface, such as the one described below in conjunction with FIG. 32, allows customization of the criteria that cause display of an alert notification 3110.

FIG. 32 is an example of a user interface 3200 for specifying generation of an alert for an asset or user tracked by the tracking server 210. The user interface 3200 includes a current alert listing 3202 and an alert editor 3204. In one embodiment, data received by the user interface 3200 is communicated to the alert server 250, which generates alerts responsive to the received data. The current alert listing 3202 identifies alerts which are applied by the alert server 250 to data received from the tracking server 210 and/or from one or more PDKs 102. For example, the current alert listing 3202 displays an alert identifier and a description of the alerts currently being monitored by the alert server 250. The current alert listing 3202 also receives input stopping the alert server 250 from applying an alert to received data. Also, the current alert listing 3202 receives input for creating a new alert for application by the alert server 250.

The alert editor 3204 receives input for specifying a new alert or for modifying attributes of an existing alert. For example, the alert editor 3204 receives data identifying the source of data for which the alert server 250 applies the alert, such as from the tracking server 210, from a PDK 102 or from a Reader 108 or other sensor. The alert editor 3204 also receives data specifying the criteria causing an alert to be generated. For example, the alert editor 3204 receives data specifying a temperature range so that an alert is generated when the alert server 250 receives data from a source indicating the temperature is within the specified range.

The alert editor 3204 also receives data specifying how the alert server 250 notifies a user that an alert is generated. In one embodiment, the alert editor 3204 receives data identifying one or more communication protocols and contact information used to communicate an alert notification to a user. For example, the alert editor 3204 receives a user telephone number and e-mail address associated with a user, allowing the user to receive notification of an alert via a telephone call, a text message and/or an e-mail. In one embodiment, the alert editor 3204 associates a priority level to be associated with different communication protocols to allow a user to specify how the user is notified when an alert is generated. For example, the alert editor 3204 associates a first communication protocol with a first priority level and if the tracking server 210 does not receive a response within a specified time interval after notifying a user of an alert, a second communication protocol having a second priority level is used to again notify the user of the alert.

FIG. 33 is an example of a user interface 3300 for describing reports generated by data received from the tracking server 210 describing movement of assets or users. The user interface 3300 includes a current report listing 3302 and a report editor 3304. The current report listing 3302 identifies reports which are generated by the tracking server 210 based on data received from PDKs 102 or other sources. For example, the current report listing 3302 displays a report identifier and a description of the reports being generated by the tracking server 210. The current report listing 3302 also receives input stopping the generation of a report by the tracking server 210 from received data. Also, the current report listing 3302 receives input for creating a new report for generation by the tracking server 210 or for editing a report generated by the tracking server 210.

The report editor 3304 receives input for specifying a new report for generation or for modifying a currently generated report. For example, the report editor 3304 receives data identifying a type of report, a PDK 102 from which data for the report is received, one or more locations from which data included in the report is received, a time interval associated with the report and a description of data included in the generated report. For example, the report editor 3304 receives data indicating that the report includes the number of PDKs 102 visiting a location, the total number of locations visited by a PDK 102, the length of time a PDK 102 was in a location or other suitable data. In one embodiment, the report editor 3304 also receives data describing how the content included in the report is presented.

The foregoing description of the embodiments of the present embodiment of invention has been presented for the purposes of illustration and description. It is not intended to be exhaustive or to limit the present embodiment of invention to the precise form disclosed. Many modifications and variations are possible in light of the above teaching. It is intended that the scope of the present embodiment of invention be limited not by this detailed description, but rather by the claims of this application. As will be understood by those familiar with the art, the present embodiment of invention may be embodied in other specific forms without departing from the spirit or essential characteristics thereof. Likewise, the particular naming and division of the modules, routines, features, attributes, methodologies and other aspects are not mandatory or significant, and the mechanisms that implement the present embodiment of invention or its features may have different names, divisions and/or formats. Furthermore, as will be apparent to one of ordinary skill in the relevant art, the modules, routines, features, attributes, methodologies and other aspects of the present embodiment of invention can be implemented as software, hardware, firmware or any combination of the three. Also, wherever a component, an example of which is a module, of the present embodiment of invention is implemented as software, the component can be implemented as a standalone program, as part of a larger program, as a plurality of separate programs, as a statically or dynamically linked library, as a kernel loadable module, as a device driver, and/or in every and any other way known now or in the future to those of ordinary skill in the art of computer programming. Additionally, the present embodiment of invention is in no way limited to implementation in any specific programming language, or for any specific operating system or environment. Accordingly, the disclosure of the present embodiment of invention is intended to be illustrative, but not limiting, of the scope of the present embodiment of invention, which is set forth in the following claims.

What is claimed is:

1. A system comprising:
one or more processors; and
a memory including instructions that, when executed by the one or more processors, causes the system to:
determine one or more prerequisites for accessing a physically shared computing device, the physically shared computing device having at least one prerequisite for access that differs from a computing device that is not physically shared, wherein the one or more prerequisites for accessing the physically shared computing device include biometric authentication and selection of a user name
subsequent to biometric authentication of a first user, identify a first user name;
subsequent to biometric authentication of a second user, identify a second user name;
receive the first user name as a selected user name from a group including the first user name and the second user name; and
subsequent to receiving the selected user name and subsequent to biometric authentication of the first user, launch one or more applications based on the selected user name, wherein the biometric authentication and selection of the user name satisfy the prerequisites for accessing the physically shared computing device.

2. The system of claim 1, wherein the biometric authentication of the first user and the first user name are based on a first profile stored on a first personal digital key (PDK) physically located within a wireless proximity zone associated with the computing device and the biometric authentication of the second user and the second user name are based on a second profile stored on a second PDK physically located within a wireless proximity zone associated with the computing device.

3. The system of claim 2, wherein the instructions, when executed, by the one or more processors, further cause the system to request the first profile subsequent to detection of the first PDK entering the wireless proximity zone.

4. The system of claim 1, wherein the biometric authentication includes obtaining, from a user, a physical or behavioral characteristics identifying the user using a biometric reader included in the PDK or associated with the computing device and authenticating the user based on the physical or behavioral characteristic.

5. The system of claim 4, wherein the biometric reader is at least one of a fingerprint scanner, a retinal scanner, an iris scanner, a face scanner, a palm scanner, a DNA analyzer, a signature analyzer or a voice analyzer.

6. The system of claim 1, wherein determining the one or more applications for launch includes determining a default scenario defining the one or more applications, wherein the one or more applications launched are launched automatically subsequent to the completion of the one or more prerequisites and without additional user action.

7. The system of claim 1, wherein determining the one or more applications for launch includes determining a default scenario defining the one or more applications, wherein the one or more applications launched are launched automatically subsequent to the completion of the one or more prerequisites and without additional user action, and wherein a user manually closing an application defined by the default scenario causes that application to no longer automatically launch as part of the default scenario.

8. The system of claim 1, wherein determining the one or more applications for launch includes determining a default scenario defining the one or more applications, wherein the one or more applications launched are launched automatically subsequent to the completion of the one or more prerequisites and without additional user action, and wherein a user manually closing an application defined by the default scenario causes that application to no longer automatically launch unless a PDK associated with the selected user name and that default scenario exits and re-enters the wireless proximity zone.

9. The system of claim 1, wherein the instructions, when executed, by the one or more processors, further cause the system to automatically navigate to one or more of a specific user interface of a launched application and a specific location within a user interface of the launched application based on a location preference, the launched application being one of the one or more applications launched based on a profile stored on a PDK physically located within a wireless proximity zone associated with the computing device.

10. The system of claim 9, wherein the specific location within a user interface of the launched application based on a location preference is a text entry region.

11. The system of claim 1, wherein at least one of the one or more applications is an application whose execution is limited to one or more permitted users.

12. The system of claim 1, wherein the wireless proximity zone is asymmetric in a first direction.

13. The system of claim 1, wherein the instructions, when executed, by the one or more processors, further cause the system to lock a display device of the physically shared computing device responsive to receiving a signal that the a PDK associated with the selected user name is outside of a wireless proximity zone associated with the computing device.

14. The system of claim 13, wherein the instructions, when executed, by the one or more processors, further cause the system to display advertisements received from a third party site, the advertisements displayed using the display device when the display device is locked.

15. The system of claim 14, wherein the third party site identifies the one or more advertisements based on data received from the computing device.

16. A method comprising:
   determining one or more prerequisites for accessing a physically shared computing device, physically shared computing device having at least one prerequisite for access that differings from a computing device that is not physically shared, wherein the one or more prerequisites for accessing the physically shared computing device include biometric authentication and selection of a user name;
   subsequent to biometric authentication of a first user, identifying a first user name;
   subsequent to biometric authentication of the second user, identifying a second user name;
   receiving the first user name as a selected user name from a group including the first user name and the second user name; and
   subsequent to receiving the selected user name and subsequent to biometric authentication of the first user, launching one or more applications based on the selected user name, wherein the biometric authentication and selection of the user name satisfy the prerequisites for accessing the physically shared computing device.

17. The method of claim 16, wherein the biometric authentication of the first user and the first user name are based on a first profile stored on a first personal digital key (PDK) physically located within a wireless proximity zone associated with the computing device and the biometric authentication of the second user and the second user name are based on a second profile stored on a second PDK physically located within a wireless proximity zone associated with the computing device.

18. The method of claim 16, wherein the biometric authentication includes using biometric data received from at least one of a fingerprint scanner, a retinal scanner, an iris scanner, a face scanner, a palm scanner, a DNA analyzer, a signature analyzer or a voice analyzer.

19. The method of claim 16, wherein the biometric authentication includes obtaining, from a user, a physical or behavioral characteristics identifying the user using a biometric reader included in the PDK or associated with the computing device and authenticating the user based on the physical or behavioral characteristic.

20. The method of claim 16, wherein determining the one or more applications for launch includes determining a default scenario defining the one or more applications, wherein the one or more applications launched are launched automatically subsequent to the completion of the one or more prerequisites and without additional user action.

* * * * *

UNITED STATES PATENT AND TRADEMARK OFFICE
CERTIFICATE OF CORRECTION

PATENT NO. : 9,807,091 B2
APPLICATION NO. : 15/207313
DATED : October 31, 2017
INVENTOR(S) : John J. Giobbi Page 1 of 1

It is certified that error appears in the above-identified patent and that said Letters Patent is hereby corrected as shown below:

In the Claims

In Column 44, Line 25, please replace "differings" with --differs--

Signed and Sealed this
Twenty-sixth Day of December, 2017

Joseph Matal
*Performing the Functions and Duties of the
Under Secretary of Commerce for Intellectual Property and
Director of the United States Patent and Trademark Office*